United States Patent
Miyagi et al.

(10) Patent No.: US 12,291,506 B2
(45) Date of Patent: May 6, 2025

(54) METHOD FOR PRODUCING AMIDATE COMPOUND, AND AMIDATE COMPOUND

(71) Applicant: KOEI CHEMICAL COMPANY, LIMITED, Chiba (JP)

(72) Inventors: Motoyoshi Miyagi, Chiba (JP); Mitsuki Onoda, Chiba (JP); Shingo Nitta, Chiba (JP)

(73) Assignee: KOEI CHEMICAL COMPANY, LIMITED, Chiba (JP)

( * ) Notice: Subject to any disclaimer, the term of this patent is extended or adjusted under 35 U.S.C. 154(b) by 1050 days.

(21) Appl. No.: 17/276,642

(22) PCT Filed: Sep. 27, 2019

(86) PCT No.: PCT/JP2019/038180
§ 371 (c)(1),
(2) Date: Mar. 16, 2021

(87) PCT Pub. No.: WO2020/067431
PCT Pub. Date: Apr. 2, 2020

(65) Prior Publication Data
US 2022/0048864 A1 Feb. 17, 2022

(30) Foreign Application Priority Data

Sep. 28, 2018 (JP) .................. 2018-183232

(51) Int. Cl.
*C07D 233/58* (2006.01)
*C08G 18/20* (2006.01)
*C08G 18/80* (2006.01)

(52) U.S. Cl.
CPC ....... *C07D 233/58* (2013.01); *C08G 18/2027* (2013.01); *C08G 18/80* (2013.01)

(58) Field of Classification Search
CPC ... C07D 233/58; C08G 18/2027; C08G 18/80
See application file for complete search history.

(56) References Cited

U.S. PATENT DOCUMENTS

| | | | |
|---|---|---|---|
| 4,200,725 | A | 4/1980 | Gras et al. |
| 9,688,641 | B2 | 6/2017 | Mauduit et al. |
| 10,689,478 | B2 | 6/2020 | Miyagi et al. |
| 10,913,724 | B2 | 2/2021 | Tsuboi et al. |
| 2003/0078450 | A1 | 4/2003 | Kocher et al. |
| 2006/0247341 | A1 | 11/2006 | Hsieh et al. |
| 2007/0035634 | A1 | 2/2007 | Edgar |
| 2012/0302782 | A1 | 11/2012 | Yamamoto et al. |
| 2015/0329494 | A1 | 11/2015 | Mauduit et al. |
| 2019/0177464 | A1 | 6/2019 | Miyagi et al. |
| 2020/0024237 | A1 | 1/2020 | Tsuboi et al. |
| 2020/0216600 | A1 | 7/2020 | Miyagi et al. |
| 2020/0248009 | A1 | 8/2020 | Matsunaga et al. |

FOREIGN PATENT DOCUMENTS

| | | |
|---|---|---|
| CN | 101165048 | 4/2008 |
| CN | 104450811 | 3/2015 |
| DE | 27 29 704 | 1/1979 |
| JP | 2016-501891 | 1/2016 |
| JP | 2018-172352 | 11/2018 |
| WO | 2018/110670 | 6/2018 |
| WO | 2018/025970 | 8/2018 |
| WO | 2018/181753 | 10/2018 |
| WO | 2019/065953 | 4/2019 |
| WO | 2019/066029 | 4/2019 |

OTHER PUBLICATIONS

Li, Chemistry—An Asian Journal, 2011, 6(6), 1520-1524. (Year: 2011).*
Temprado, Structural Chemistry, 2013, 24(6), 2059-2068. (Year: 2013).*
Winkler, J Organometallic Chem, 2015, 775, 164-168. (Year: 2015).*
Schoessler, Chemische Berichte, 1974, 107(6), 1931-1948. (Year: 1974).*
Temprado, Struct Chem, 2013, vol. 24, 2059-2068. (Year: 2013).*
"STN Search Report", CA, CAPLUS, pp. 1-3, dated Jun. 29, 2023, citing CAS Reg. No. 1344705-14-1.
International Search Report issued Dec. 17, 2019 in International (PCT) Application No. PCT/JP2019/038180.
Coutelier et al., "N-Heterocyclic Carbene-catalyzed synthesis of Polyurethanes", Polymer Preprints, 2011, vol. 52, No. 2, pp. 290-291.
Li et al., "Amine-Linked N-Heterocyclic Carbenes: The Importance of an Pendant Free-Amine Auxiliary in Assisting the Catalytic Reaction", Chemistry an Asian Journal, 2011, vol. 6, No. 6, pp. 1520-1524.
Temprado et al., "Synthesis, structure, and thermochemistry of adduct formation between N-heterocyclic carbenes and isocyanates or mesity lnitrile oxide", Structural Chemistry, 2013, vol. 24, No. 6, pp. 2059-2068.
Winkler et al., "Preparation and reactivity of an isolable N-heterocyclic carbene-borane", Journal of Organometallic Chemistry, 2015, vol. 775, pp. 164-168.
Schoessler et al., "Stable Dipoles from the Reaction of 1,1', 3,3'-Tetraphenyl-2,2'-biimidazolidinylidenes with Acyl Isocyanates or Acyl Isothiocyanates", Chemische Berichte, 1974, vol. 107, No. 6, pp. 1931-1948.
Wang et al., "High-Spin Iron(II) Alkynyl Complexes with N-Heterocyclic Carbene Ligation: Synthesis, Characterization, and Reactivity Study", Organometallics, 2015, vol. 34, No. 12, pp. 2775-2782.
Han et al., "Reactivities of zero-valent group 10 complexes toward organic isocyanate: synthesis of metallacycles containing dimeric isocyanate units, isocyanate cyclotrimerization, and computational Chemistry", New Journal of Chemistry, 2019, vol. 43, No. 39, pp. 15614-15625.

(Continued)

*Primary Examiner* — D Margaret M Seaman
(74) *Attorney, Agent, or Firm* — Wenderoth, Lind & Ponack, L.L.P.

(57) ABSTRACT

A method for producing an amidate compound represented by Formula (4), comprising reacting an iminium salt represented by Formula (1) and an organic compound represented by Formula (3), wherein Formulas (1), (3), and (4) are as defined in the description.

10 Claims, No Drawings

(56) References Cited

OTHER PUBLICATIONS

Indian Office Action dated Nov. 2, 2022 in corresponding Indian Patent Application No. 202117011355, with English translation.
Olivier Coutelier et al., "N-Heterocyclic carbene-catalysed synthesis of polyurethanes", Polymer Chemistry, (2012), vol. 3, pp. 605-608.

* cited by examiner

METHOD FOR PRODUCING AMIDATE COMPOUND, AND AMIDATE COMPOUND

TECHNICAL FIELD

The present invention relates to a method for producing an amidate compound, and an amidate compound.

BACKGROUND ART

Known conventional methods for producing amidate compounds include (1) a method comprising reacting alkylimidazole with dimethyl carbonate to form a $CO_2$ adduct, and then reacting the $CO_2$ adduct with an isocyanate compound (Patent Literature (PTL) 1); and (2) a method for reacting dialkylimidazolium carbene with an isocyanate compound (Non-patent Literature (NPL) 1).

It is also disclosed that the amidate compound of PTL 1 can be used as a catalyst for urethane polymerization. The amidate compound of PTL 1 has a methyl group in which at least one of the substituents on the nitrogen atom in the heterocyclic skeleton is always a primary carbon atom.

CITATION LIST

Patent Literature

PTL 1: WO2018/025970

Non-Patent Literature

NPL 1: Struct. Chem., 2013, Vol. 24, pp. 2059-206

SUMMARY OF INVENTION

Technical Problem

However, in the method (1) of PTL 1, a reaction temperature above the boiling point of dimethyl carbonate is always needed, which requires pressure reaction equipment. On the other hand, the method (2) of NPL 1 requires the production of NHC carbene; however, carbene is a compound that is generally unstable to oxygen or water, and thus needs to be handled in special equipment such as a glove box. Accordingly, the method (2) is not satisfactory from a practical standpoint. Further, it is difficult to isolate carbene unless the carbene is a highly stable NHC carbene in which the substituent on the nitrogen atom of the heterocyclic framework is an isopropyl group; accordingly, the substituent on the nitrogen atom of the heterocyclic framework is consequently limited in the method (2). For amidate compounds that can be produced, producing amidate compounds other than the specific compound is difficult.

Additionally, the present inventors found that the use of 1-methyl-3-octylimidazolium-2-N-phenylamidate (OMIm-PI), which is the amidate compound of PTL 1, as a catalyst for urethane polymerization of thermosetting resin (blocked dissociation catalyst), does not give satisfactory results in view of the compatibility of OMIm-PI with a mixture of a blocked isocyanate, which is a thermosetting composition raw material, and a compound having an isocyanate-reactive group; and that improvements in this regard can be made (see Reference Example 1 below).

The present invention was made in light of the above background art. An object of the present invention is to provide (I) a method for producing an amidate compound that does not require special equipment, such as pressure reaction equipment or a glove box; and (II) a novel amidate compound that has improved compatibility with a thermosetting composition raw material.

Solution to Problem

The present inventors conducted extensive research to solve the above problems, and found that (I) a corresponding amidate compound can be produced from an iminium salt into which various substituents can be easily introduced on the nitrogen atom, without the need for special equipment; and that (II) an amidate compound (4) that can be produced by the production method of the present invention, in particular, an amidate compound (4) in which $R^1$ and $R^4$ of the nitrogen-containing organic group represented by Formula (2) have 2 to 30 carbon atoms, has improved compatibility with a thermosetting composition raw material. The present invention was thus accomplished.

Specifically, the present invention includes the following [1] to [14].

[1] A method for producing an amidate compound represented by Formula (4), comprising reacting an iminium salt represented by the following Formula (1) and an organic compound represented by the following Formula (3):

Formula (1):

$$D\text{-}H\ G^- \tag{1}$$

wherein $G^-$ is an anion, and D is a nitrogen-containing organic group represented by Formula (2):

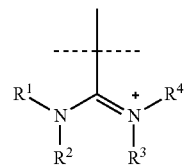

(2)

wherein $R^1$, $R^2$, $R^3$, and $R^4$ are the same or different, and are each a hydrocarbon group that may contain a heteroatom; and some or all of $R^1$, $R^2$, $R^3$, and $R^4$ may be bonded together to form a ring structure;

Formula (3):

$$A\text{-}(Q)_n \tag{3}$$

wherein A is a substituted or unsubstituted hydrocarbon group, n is an integer of 1 or more, Q is an —NCO group or an —$NHCO_2R^7$ group, and $R^7$ is a substituted or unsubstituted hydrocarbon group;

Formula (4):

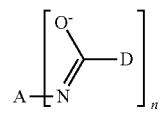

(4)

wherein A, D, and n are as defined above.

[2] The method for producing an amidate compound according to [1], wherein the nitrogen-containing organic group represented by Formula (2) is a nitrogen-containing organic group represented by the following Formula (2-1), (2-2), or (2-3):

Formula (2-1):

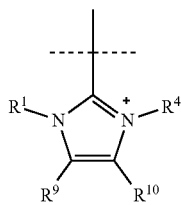

(2-1)

wherein $R^1$ and $R^4$ are as defined above, and $R^9$ and $R^{10}$ are the same or different, and are each a hydrogen atom or a $C_1$-$C_6$ hydrocarbon group that may contain a heteroatom;

Formula (2-2):

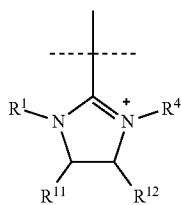

(2-2)

wherein $R^1$ and $R^4$ are as defined above, and $R^{11}$ and $R^{12}$ are the same or different, and are each a hydrogen atom or a $C_1$-$C_6$ hydrocarbon group that may contain a heteroatom; or Formula (2-3):

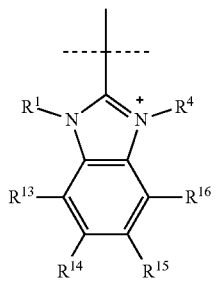

(2-3)

wherein $R^1$ and $R^4$ are as defined above, and $R^{13}$, $R^{14}$, $R^{15}$, and $R^{16}$ are the same or different, and are each a hydrogen atom or a $C_1$-$C_6$ hydrocarbon group that may contain a heteroatom.

[3] The method for producing an amidate compound according to [1] or [2], wherein the organic compound represented by Formula (3) is represented by the following Formula (3-1), (3-2), or (3-3):

Formula (3-1):

$R^5$-Q  (3-1)

wherein Q is as defined above, and $R^5$ is a substituted or unsubstituted hydrocarbon group;

Formula (3-2):

Q-$R^6$-Q  (3-2)

wherein Q is as defined above, and $R^6$ is a substituted or unsubstituted hydrocarbon group; or Formula (3-3):

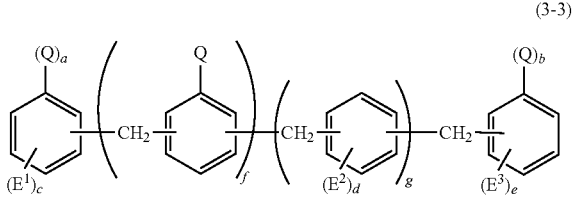

(3-3)

wherein Q is as defined above; $E^1$, $E^2$, and $E^3$ are each independently a substituted or unsubstituted hydrocarbon group, a halogen atom, an alkylamino group, a dialkylamino group, an alkoxy group, an aryloxy group, a nitro group, a cyano group, a sulfonyl group, an (alkylamino)carbonylamino group, a (dialkylamino)carbonylamino group, or an isocyanate group; f and g are each independently an integer of 0 to 4; a and b are 0 or 1; and c, d, and e are each independently an integer of 0 to 4; provided that when f is 0, at least one of a or b is 1.

[4] The method for producing an amidate compound according to [1] to [3], wherein Q is an —NHCO$_2$R$^7$ group.

[5] The method for producing an amidate compound according to [1] to [4], wherein G⁻ is a carboxylate ion represented by the following Formula (5):

Formula (5):

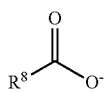

(5)

wherein $R^8$ is a hydrogen atom, a hydroxyl group, an alkoxy group, an fluoroalkyl group, or a hydrocarbon group that may contain a heteroatom.

[6] The method for producing an amidate compound according to [1] to [5], wherein A is an unsubstituted hydrocarbon group or a hydrocarbon group having at least one substituent selected from a halogen atom, an alkylamino group, a dialkylamino group, an alkoxy group, an aryloxy group, a nitro group, a cyano group, a sulfonyl group, an (alkylamino) carbonylamino group, a (dialkylamino)carbonylamino group, and an isocyanate group.

[7] The method for producing an amidate compound according to [1] to [6], wherein n is an integer of 1 to 6.

[8] An amidate compound represented by Formula (4), provided that 4,5-dimethyl-1,3-diisopropylimidazolium-2-N-(p-isopropylphenyl) amidate, 1,3-bis(2,6-diisopropylphenyl) imidazolium-2-N-(1-adamantyl) amidate, and 1,3-bis (2,6-diisopropylphenyl)imidazolium-2-N-phenylamidate are excluded:

Formula (4):

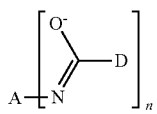

(4)

wherein A is a substituted or unsubstituted hydrocarbon group, n is an integer of 1 or more, and D is a nitrogen-containing organic group represented by Formula (2):

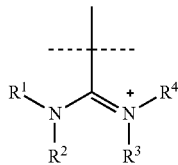

(2)

wherein $R^1$ and $R^4$ are the same or different, and are each a $C_2$-$C_{30}$ hydrocarbon group that may contain a heteroatom; $R^2$ and $R^3$ are as defined above; and some or all of $R^1$, $R^2$, $R^3$, and $R^4$ may be bonded together to form a ring structure.

[9] The amidate compound according to [8], wherein A is an unsubstituted hydrocarbon group or a hydrocarbon group having at least one substituent selected from a halogen atom, an alkylamino group, a dialkylamino group, an alkoxy group, an aryloxy group, a nitro group, a cyano group, a sulfonyl group, an (alkylamino)carbonylamino group, a (dialkylamino)carbonylamino group, and an isocyanate group.

[10] The amidate compound according to [8] or [9], wherein n is an integer of 1 to 6.

[11] The amidate compound according to [8], wherein the amidate compound represented by Formula (4) is represented by the following Formula (4-1), (4-2), or (4-3):

Formula (4-1):

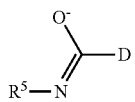

(4-1)

wherein $R^5$ is a substituted or unsubstituted hydrocarbon group, and D is as defined above;

Formula (4-2):

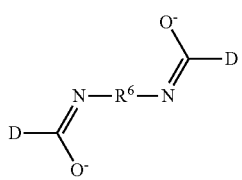

(4-2)

wherein $R^6$ is a substituted or unsubstituted hydrocarbon group, and D is as defined above; or Formula (4-3):

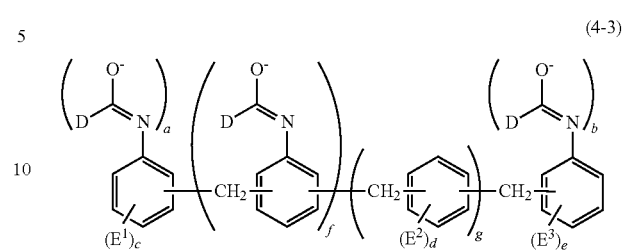

(4-3)

wherein D is as defined above; $E^1$, $E^2$, and $E^3$ are each independently a substituted or unsubstituted hydrocarbon group, a halogen atom, an alkylamino group, a dialkylamino group, an alkoxy group, an aryloxy group, a nitro group, a cyano group, a sulfonyl group, an (alkylamino)carbonylamino group, a (dialkylamino)carbonylamino group, or an isocyanate group; f and g are each independently an integer of 0 to 4; a and b are 0 or 1; and c, d, and e are each independently an integer of 0 to 4; provided that when f is 0, at least one of a or b is 1.

[12] The amidate compound according to [8] to [11], wherein the nitrogen-containing organic group represented by Formula (2) is a nitrogen-containing organic group represented by the following Formula (2-1), (2-2), or (2-3):

Formula (2-1):

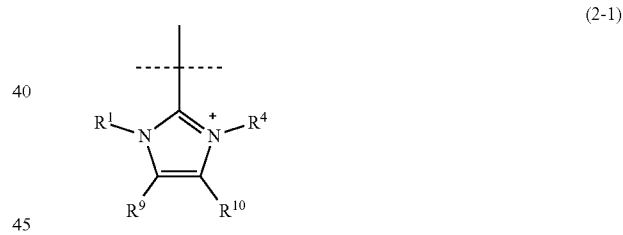

(2-1)

wherein $R^1$ and $R^4$ are as defined above, and $R^9$ and $R^{10}$ are the same or different, and are each a hydrogen atom or a $C_1$-$C_6$ hydrocarbon group that may contain a heteroatom;

Formula (2-2):

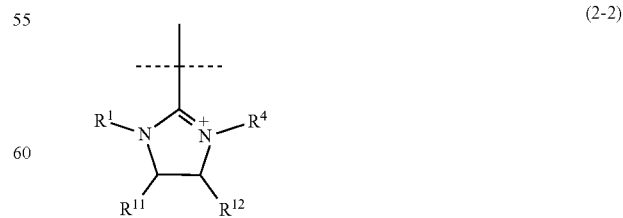

(2-2)

wherein $R^1$ and $R^4$ are as defined above, and $R^{11}$ and $R^{12}$ are the same or different, and are each a hydrogen atom or a $C_1$-$C_6$ hydrocarbon group that may contain a heteroatom; or Formula (2-3):

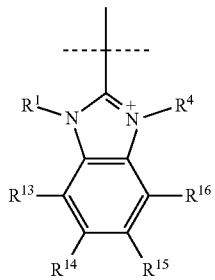

wherein $R^1$ and $R^4$ are as defined above, and $R^{13}$, $R^{14}$, $R^{15}$, and $R^{16}$ are the same or different, and are each a hydrogen atom or a $C_1$-$C_6$ hydrocarbon group that may contain a heteroatom.

[13] A blocking agent dissociation catalyst for blocked isocyanates comprising an amidate compound represented by Formula (4):

Formula (4):

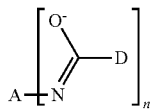

wherein A is a substituted or unsubstituted hydrocarbon group, n is an integer of 1 or more, and D is a nitrogen-containing organic group represented by Formula (2):

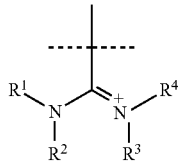

wherein $R^1$ and $R^4$ are the same or different, and are each a $C_2$-$C_{30}$ hydrocarbon group that may contain a heteroatom; $R^2$ and $R^3$ are the same or different, and are each a hydrocarbon group that may contain a heteroatom; and some or all of $R^1$, $R^2$, $R^3$, and $R^4$ may be bonded together to form a ring structure.

[14] A thermosetting composition comprising the blocking agent dissociation catalyst for blocked isocyanates according to [13], a blocked isocyanate, and a compound having an isocyanate-reactive group.

Advantageous Effects of Invention

The present invention can provide (I) a method for producing an amidate compound that does not require special equipment such as pressure reaction equipment or a glove box, in which a compound having various substituents on the nitrogen atom of the heterocyclic framework of the amidate compound can be produced; and (II) a novel amidate compound having improved compatibility with a thermosetting composition raw material.

DESCRIPTION OF EMBODIMENTS

Embodiments for carrying out the present invention are described in detail below.

Method for Producing Amidate Compound

First, an iminium salt represented by Formula (1) (hereinafter referred to as "the iminium salt (1)") is explained.

In Formula (1), $G^-$ is an anion. D is a nitrogen-containing organic group represented by Formula (2). The anion is not particularly limited, as long as it can form a salt with the iminium cation represented by Formula (2). Examples include carboxylate ions, halogen ions, sulfonate ions, phosphate ions, and the like; and preferably a carboxylate ion represented by the following Formula (5):

Formula (5):

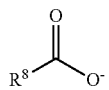

wherein $R^8$ is a hydrogen atom, a hydroxyl group, an alkoxy group, an fluoroalkyl group, or a hydrocarbon group that may contain a heteroatom.

In Formula (5), $R^8$ is a hydrogen atom, a hydroxyl group, an alkoxy group, an fluoroalkyl group, or a hydrocarbon group that may contain a heteroatom. $R^8$ is preferably a hydroxyl group or a hydrocarbon group that may contain a heteroatom, and more preferably a hydrocarbon group that may contain a heteroatom. The alkoxy group is preferably a $C_1$-$C_4$ alkoxy group, and particularly preferably a $C_1$ or $C_2$ alkoxy group. The fluoroalkyl group is preferably a $C_1$-$C_6$ fluoroalkyl group, and particularly preferably a $C_1$-$C_4$ fluoroalkyl group. The hydrocarbon group that may contain a heteroatom (that is, a heteroatom is contained or is not contained) is preferably a $C_1$-$C_6$ hydrocarbon group, and particularly preferably a $C_1$-$C_6$ hydrocarbon group that does not contain a heteroatom.

In the present specification, examples of heteroatoms include nitrogen, oxygen, and sulfur atoms.

Examples of the carboxylate ion represented by Formula (5) include carboxylate ions, such as formate ion, acetate ion, propionate ion, butyrate ion, methoxyacetate ion, ethoxyacetate ion, propoxyacetate ion, 2-(2-methoxyethoxy)acetate ion, 2-(2-ethoxyethoxy)acetate ion, 2-(2-propoxyethoxy)acetate ion, 3-methoxypropanoate ion, 3-ethoxypropanoate ion, 3-(2-methoxyethoxy)propanoate ion, 3-(2-ethoxyethoxy)propanoate ion, 3-(2-propoxyethoxy)propanoate ion, 3-(3-methoxypropoxy)propanoate ion, 3-(3-ethoxypropoxy)propanoate ion, 3-(3-propoxypropoxy)propanoate ion, oleate ion, linoleate ion, sorbate ion, benzoate ion, phthalate ion, isophthalate ion, terephthalate ion, lactate ion, salicylate ion, and trifluoroacetate; alkyl carbonate ions, such as methyl carbonate ion and ethyl carbonate ion; hydrogen carbonate ions; and the like.

Examples of halogen ions include chlorine ion, bromine ion, iodine ion, and the like; and preferably chlorine ion.

Examples of sulfonate ions include methanesulfonate ion, trifluoromethanesulfonate ion, nonafluorobutanesulfonate ion, benzenesulfonate ion, p-toluenesulfonate ion, and the like; and preferably methanesulfonate ion.

Examples of phosphate ions include dimethylphosphate ion, diethylphosphate ion, dibutylphosphate ion, and the like; and preferably dimethylphosphate ion.

The nitrogen-containing organic group represented by Formula (2) (hereinafter referred to as "the nitrogen-containing organic group (2)") is explained.

In Formula (2), $R^1$, $R^2$, $R^3$, and $R^4$ are each a hydrocarbon group that may contain a heteroatom, preferably a $C_1$-$C_{30}$ hydrocarbon group that may contain a heteroatom, more preferably a $C_1$-$C_{20}$ hydrocarbon group that may contain a heteroatom, and particularly preferably a $C_1$-$C_9$ hydrocarbon group that may contain a heteroatom. Some or all of $R^1$, $R^2$, $R^3$, and $R^4$ may be bonded together to form a ring structure. For example, $R^1$ and $R^2$, $R^2$ and $R^3$, $R^3$ and $R^4$, $R^2$, $R^3$, and $R^4$, or $R^1$, $R^2$, $R^3$, and $R^4$, may be bonded together to form a ring structure. Examples of the hydrocarbon group that may contain a heteroatom include methyl, ethyl, propyl, isopropyl, butyl, sec-butyl, tert-butyl, pentyl, hexyl, octyl, 2-ethylhexyl, decyl, dodecyl, tetradecyl, hexadecyl, octadecyl, allyl, benzyl, cyclohexyl, adamantyl, phenyl, 2,6-diisopropylphenyl, 2,4,6-trimethylphenyl, 2-methoxyethyl, 2-ethoxyethyl, 2-(dimethylamino)ethyl, and the like; preferably methyl, ethyl, propyl, isopropyl, butyl, octyl, dodecyl, octadecyl, cyclopentyl, cyclohexyl, 2-ethylhexyl, benzyl, phenyl, and 2,4,6-trimethylphenyl; and particularly preferably methyl, ethyl, butyl, octyl, 2-ethylhexyl, and benzyl.

In another embodiment of the present invention, $R^1$ and $R^4$ are the same or different, and are each a $C_2$-$C_{30}$ hydrocarbon group that may contain a heteroatom, preferably a $C_7$-$C_{30}$ hydrocarbon group, and more preferably a $C_7$-$C_{20}$ hydrocarbon group. $R^2$ and $R^3$ are the same or different, and are each a hydrocarbon group that may contain a heteroatom. Some or all of $R^1$, $R^2$, $R^3$, and $R^4$ may be bonded together to form a ring structure.

In the present invention, $R^2$ and $R^3$ in the nitrogen-containing organic group (2) are preferably bonded together to form a ring structure. The nitrogen-containing organic group (2) wherein a ring is formed is preferably a nitrogen-containing organic group represented by Formula (2-1), (2-2), or (2-3), and particularly preferably a nitrogen-containing organic group represented by Formula (2-1).

In Formula (2-1), $R^1$ and $R^4$ are as defined above. $R^9$ and $R^{10}$ are hydrogen atoms or $C_1$-$C_6$ hydrocarbon groups that may contain a heteroatom, and preferably hydrogen atoms. Examples of the $C_1$-$C_6$ hydrocarbon group that may contain a heteroatom include a methyl group, an ethyl group, a propyl group, an isopropyl group, a butyl group, a sec-butyl group, a tert-butyl group, a hexyl group, a cyclohexyl group, a phenyl group, a 2-methoxyethyl group, a 2-ethoxyethyl group, a 2-(dimethylamino)ethyl group, and the like; and preferably a methyl group.

In the present specification, the terms propyl, butyl, pentyl, hexyl, heptyl, octyl, nonyl, dodecyl, tetradecyl, hexadecyl, octadecyl, etc., refer to linear alkyl groups, such as n-propyl, n-butyl, n-pentyl, n-hexyl, n-heptyl, n-octyl, n-nonyl, n-dodecyl, n-tetradecyl, n-hexadecyl, and n-octadecyl, respectively, unless otherwise specified.

Specific examples of the nitrogen-containing organic group (2-1) include a 1,3-dimethylimidazolium group, a 1-ethyl-3-methylimidazolium group, a 1-methyl-3-propylimidazolium group, a 1-methyl-3-isopropylimidazolium group, a 1-butyl-3-methylimidazolium group, a 1-tert-butyl-3-methylimidazolium group, a 1-hexyl-3-methylimidazolium group, a 1-cyclohexyl-3-methylimidazolium group, a 1-methyl-3-octylimidazolium group, a 1-methyl-3-(2-ethylhexyl)imidazolium group, a 1-dodecyl-3-methylimidazolium group, a 1-methyl-3-tetradecylimidazolium group, a 1-hexadecyl-3-methylimidazolium group, a 1-methyl-3-octadecylimidazolium group, a 1-allyl-3-methylimidazolium group, a 1-benzyl-3-methylimidazolium group, a 1-methyl-3-phenylimidazolium group, a 1-methyl-3-(2,6-diisopropylphenyl)imidazolium group, a 1-mesityl-3-methylimidazolium group, a 1,3-diethylimidazolium group, a 1-ethyl-3-propylimidazolium group, a 1-ethyl-3-isopropylimidazolium group, a 1-butyl-3-ethylimidazolium group, a 1-ethyl-3-tert-butylimidazolium group, a 1-ethyl-3-hexylmethylimidazolium group, a 1-ethyl-3-cyclohexylmethylimidazolium group, a 1-ethyl-3-octylimidazolium group, a 1-ethyl-3-(2-ethylhexyl)imidazolium group, a 1-ethyl-3-dodecylimidazolium group, a 1-ethyl-3-tetradecylimidazolium group, a 1-ethyl-3-hexadecylimidazolium group, a 1-ethyl-3-octadecylimidazolium group, a 1-allyl-3-ethylimidazolium group, a 1-benzyl-3-ethylimidazolium group, a 1-ethyl-3-phenylimidazolium group, a 1-ethyl-3-(2,6-diisopropylphenyl)imidazolium group, a 1-ethyl-3-mesitylimidazolium group, a 1,3-dipropylimidazolium group, a 1-propyl-3-isopropylimidazolium group, a 1-butyl-3-propylimidazolium group, a 1-tert-butyl-3-propylimidazolium group, a 1-hexyl-3-propylimidazolium group, a 1-cyclohexyl-3-propylimidazolium group, a 1-octyl-3-propylimidazolium group, a 1-(2-ethylhexyl)-3-propylimidazolium group, a 1-dodecyl-3-propylimidazolium group, a 1-propyl-3-tetradecylimidazolium group, a 1-hexadecyl-3-propylimidazolium group, a 1-octadecyl-3-propylimidazolium group, a 1-allyl-3-propylimidazolium group, a 1-benzyl-3-propylimidazolium group, a 1-phenyl-3-propylimidazolium group, a 1-propyl-3-(2,6-diisopropylphenyl)imidazolium group, a 1-mesityl-3-propylimidazolium group, a 1,3-diisopropylimidazolium group, a 1-butyl-3-isopropylimidazolium group, a 1-tert-butyl-3-isopropylimidazolium group, a 1-hexyl-3-isopropylimidazolium group, a 1-cyclohexyl-3-isopropylimidazolium group, a 1-octyl-3-isopropylimidazolium group, a 1-(2-ethylhexyl)-3-isopropylimidazolium group, a 1-dodecyl-3-isopropylimidazolium group, a 1-isopropyl-3-tetradecylimidazolium group, a 1-hexadecyl-3-isopropylimidazolium group, a 1-octadecyl-3-isopropylimidazolium group, a 1-allyl-3-isopropylimidazolium group, a 1-benzyl-3-isopropylimidazolium group, a 1-phenyl-3-isopropylimidazolium group, a 1-isopropyl-3-(2,6-diisopropylphenyl)imidazolium group, a 1-mesityl-3-isopropylimidazolium group, a 1,3-dibutylimidazolium group, a 1-butyl-3-tert-butylimidazolium group, a 1-butyl-3-hexylmethylimidazolium group, a 1-butyl-3-octylimidazolium group, a 1-butyl-3-(2-ethylhexyl)imidazolium group, a 1-butyl-3-dodecylimidazolium group, a 1-butyl-3-tetradecylimidazolium group, a 1-butyl-3-hexadecylimidazolium group, a 1-butyl-3-cyclohexadecylimidazolium group, a 1-butyl-3-octadecylimidazolium group, a 1-allyl-3-butylimidazolium group, a 1-benzyl-3-butylimidazolium group, a 1-butyl-3-phenylimidazolium group, a 1-butyl-3-(2,6-diisopropylphenyl)imidazolium group, a 1-butyl-3-mesitylimidazolium group, a 1,3-di-tert-butylimidazolium group, a 1-tert-butyl-3-hexylmethylimidazolium group, a 1-tert-butyl-3-cyclohexylmethylimidazolium group, a 1-tert-butyl-3-octylimidazolium group, a 1-tert-butyl-3-(2-ethylhexyl)imidazolium group, a 1-tert-butyl-3-dodecylimidazolium group, a 1-tert-butyl-3-tetradecylimidazolium group, a 1-tert-butyl-3-hexadecylimidazolium group, a 1-tert-butyl-3-octadecylimidazolium group, a 1-allyl-3-tert-butylimidazolium group, a 1-benzyl-3-tert-butylimidazolium group, a 1-tert-butyl-3- phenylimidazolium group, a 1-tert-butyl-3-(2,6-diisopropylphenyl)imidazolium group, a 1-tert-butyl-3-mesitylimidazolium group, a 1,3-dihexylimidazolium group, a 1-hexyl-3-cyclohexylimidazolium group, a 1-(2-ethylhexyl)-3-hexylimidazolium group, a 1-dodecyl-3-hexylimidazolium group, a 1-hexyl-3-tetradecylimidazolium group, a 1-hexadecyl-3-hexylimidazolium group, a 1-hexyl-3-octadecylimidazolium group, a 1-allyl-3-hexylimidazolium group, a 1-benzyl-3-hexylimidazolium group, a 1-hexyl-3-phenylimidazolium group, a 1-hexyl-3-(2,6-diisopropylphenyl)imidazolium group, a 1-hexyl-3-mesitylimidazolium group, a 1,3-dicyclohexylimidazolium group, a 1-(2-ethylhexyl)-3-cyclohexylimidazolium group, a 1-dodecyl-3-cyclohexylimidazolium group, a 1-cyclohexyl-3-tetradecylimidazolium group, a 1-hexadecyl-3-cyclohexylimidazolium group, a 1-cyclohexyl-3-octadecylimidazolium group, a 1-allyl-3-cyclohexylimidazolium group, a 1-benzyl-3-cyclohexylimidazolium group, a 1-cyclohexyl-3-phenylimidazolium group, a 1-cyclohexyl-3-(2,6-diisopropylphenyl) imidazolium group, a 1-cyclohexyl-3-mesitylimidazolium group, a 1,3-dioctylimidazolium group, a 1-(2-ethylhexyl)-3-octylimidazolium group, a 1-dodecyl-3-octylimidazolium group, a 1-octyl-3-tetradecylimidazolium group, a 1-hexadecyl-3-octylimidazolium group, a 1-octadecyl-3-octylimidazolium group, a 1-allyl-3-octylimidazolium group, a 1-benzyl-3-octylimidazolium group, a 1-phenyl-3-octylimidazolium group, a 1-octyl-3-(2,6-diisopropylphenyl)imidazolium group, a 1-mesityl-3-octylimidazolium group, a 1,3-bis(2-ethylhexyl)imidazolium group, a 1-(2-ethylhexyl)-3-dodecylimidazolium group, a 1-(2-ethylhexyl)-3-tetradecylimidazolium group, a 1-(2-ethylhexyl)-3-hexadecylimidazolium group, a 1-(2-ethylhexyl)-3-octadecylimidazolium group, a 1-allyl-3-(2-ethylhexyl)imidazolium group, a 1-benzyl-3-(2-ethylhexyl)imidazolium group, a 1-(2-ethylhexyl)-3-phenylimidazolium group, a 1-(2-ethylhexyl)-3-(2,6-diisopropylphenyl)imidazolium group, a 1-(2-ethylhexyl)-3-mesitylimidazolium group, a 1,3-didodecylimidazolium group, a 1-dodecyl-3-tetradecylimidazolium group, a 1-dodecyl-3-hexadecylimidazolium group, a 1-dodecyl-3-octadecylimidazolium group, a 1-allyl-3-dodecylimidazolium group, a 1-benzyl-3-dodecylimidazolium group, a 1-dodecyl-3-phenylimidazolium group, a 1-dodecyl-3-(2,6-diisopropylphenyl)imidazolium group, a 1-dodecyl-3-mesitylimidazolium group, a 1,3-ditetradecylimidazolium group, a 1-hexadecyl-3-tetradecylinidazolium group, a 1-octadecyl-3-tetradecylimidazolium group, a 1-allyl-3-tetradecylimidazolium group, a 1-benzyl-3-tetradecylimidazolium group, a 1-phenyl-3-tetradecylimidazolium group, a 1-(2,6-diisopropylphenyl)-3-tetradecylimidazolium group, a 1-mesityl-3-tetradecylimidazolium group, a 1,3-dihexadecylimidazolium group, a 1-hexadecyl-3-octadecylimidazolium group, a 1-allyl-3-hexadecylimidazolium group, a 1-benzyl-3-hexadecylimidazolium group, a 1-hexadecyl-3-phenylimidazolium group, a 1-hexadecyl-3-(2,6-diisopropylphenyl)imidazolium group, a 1-hexadecyl-3-mesitylimidazolium group, a 1,3-dioctadecylimidazolium group, a 1-allyl-3-octadecylimidazolium group, a 1-benzyl-3-octadecylimidazolium group, a 1-phenyl-3-octadecylimidazolium group, a 1-(2,6-diisopropylphenyl)-3-octadecylimidazolium group, a 1-mesityl-3-octadecylimidazolium group, a 1,3-diallylimidazolium group, a 1-allyl-3-benzylimidazolium group, a 1-allyl-3-phenylimidazolium group, a 1-allyl-3-(2,6-diisopropylphenyl)imidazolium group, a 1-allyl-3-mesitylimidazolium group, a 1,3-dibenzylimidazolium group, a 1-benzyl-3-phenylimidazolium group, a 1-benzyl-3-(2,6-diisopropylphenyl)imidazolium group, a 1-benzyl-3-mesitylimidazolium group, a 1,3-diphenylimidazolium group, a 1-phenyl-3-(2,6-diisopropylphenyl)imidazolium group, a 1-mesityl-3-phenylimidazolium group, a 1,3-bis(2,6-diisopropylphenyl)imidazolium group, a 1-phenyl-3-(2,6-diisopropylphenyl)imidazolium group, a 1,3-dimesitylimidazolium group, a 1,3,4,5-tetramethylimidazolium group, and the like; preferably a 1,3-dimethylimidazolium group, a 1-ethyl-3-methylimidazolium group, a 1-butyl-3-methylimidazolium group, a 1-methyl-3-octylimidazolium group, a 1-methyl-3-(2-ethylhexyl)imidazolium group, a 1-dodecyl-3-methylimidazolium group, a 1-methyl-3-octadecylimidazolium group, a 1-benzyl-3-methylimidazolium group, a 1,3-dibutylimidazolium group, a 1-butyl-3-ethylimidazolium group, a 1-butyl-3-octylimidazolium group, a 1-butyl-3-(2-ethylhexyl)imidazolium group, a 1-butyl-3-dodecyl-3-butylimidazolium group, a 1-butyl-3-octadecylimidazolium group, a 1-benzyl-3-butylimidazolium group, a 1,3-dioctylimidazolium group, a 1-ethyl-3-octylimidazolium group, a 1-octyl-3-(2-ethylhexyl)imidazolium group, a 1-dodecyl-3-octylimidazolium group, a 1-octyl-3-octadecylimidazolium group, a 1-benzyl-3-octylimidazolium group, a 1,3-bis(2-ethylhexyl)imidazolium group, a 1-ethyl-3-(2-ethylhexyl)imidazolium group, a 1-(2-ethylhexyl)-3-dodecylimidazolium group, a 1-(2-ethylhexyl)-3-octadecylimidazolium group, a 1-benzyl-3-(2-ethylhexyl)imidazolium group, a 1,3-didodecylimidazolium group, a 1-dodecyl-3-octadecylimidazolium group, a 1-benzyl-3-dodecylimidazolium group, a 1,3-dioctadecylimidazolium group, a 1-benzyl-3-octadecylimidazolium group, and 1,3-dibenzylimidazolium group; and particularly preferably a 1-ethyl-3-methylimidazolium group, a 1,3-dibutylimidazolium group, a 1,3-dioctylimidazolium group, a 1,3-bis(2-ethylhexyl)imidazolium group, a 1,3-didodecylimidazolium group, and a 1,3-dibenzylimidazolium group.

In Formula (2-2), $R^1$ and $R^4$ are as defined above. $R^{11}$ and $R^{12}$ are hydrogen atoms or $C_1$-$C_6$ hydrocarbon groups that may contain a heteroatom, and preferably hydrogen atoms. Examples of the $C_1$-$C_6$ hydrocarbon group that may contain a heteroatom include a methyl group, an ethyl group, a propyl group, an isopropyl group, a butyl group, a sec-butyl group, a tert-butyl group, a pentyl group, a hexyl group, a cyclohexyl group, a phenyl group, a 2-methoxyethyl group, a 2-ethoxyethyl group, a 2-(dimethylamino)ethyl group, and the like; and preferably a methyl group.

Specific examples include a 1,3-dimethylimidazolinium group, a 1-ethyl-3-methylimidazolinium group, a 1-methyl-3-propylimidazolinium group, a 1-butyl-3-methylimidazolinium group, a 1-hexyl-3-methylimidazolinium group, a 1-methyl-3-octylimidazolinium group, a 1-dodecyl-3-methylimidazolinium group, a 1-allyl-3-methylimidazolinium group, a 1-benzyl-3-methylimidazolinium group, a 1-methyl-3-phenylimidazolinium group, a 1-methyl-3-(2,6-diisopropylphenyl)imidazolinium group, a 1-mesityl-3-methylimidazolinium group, a 1,3-diethylimidazolinium group, a 1,3-dipropylimidazolinium group, a 1,3-diisopropylimidazolinium group, a 1,3-dibutylimidazolinium group, a 1,3-di-tert-butylimidazolinium group, a 1,3-dioctylimidazolinium group, a 1,3-diphenylimidazolinium group, a 1,3-bis(2,6-diisopropylphenyl)imidazolinium group, a 1,3-dimesitylimidazolinium group, a 1,3,4,5-tetramethylimidazolinium group, a 1,3,4,5-tetramethylimidazolinium group, and the like; preferably a 1,3-dimethylimidazolinium group, a 1-ethyl-3-methylimidazolinium group, a 1-methyl-3-propylimidazolinium group, a 1-butyl-3-methylimidazolinium group, and a 1-methyl-3-octylimidazolinium group; and particularly preferably a 1,3-dimethylimidazolinium group, a 1-butyl-3-methylimidazolinium group, and a 1-methyl-3-octylimidazolinium group.

In Formula (2-3), $R^1$ and $R^4$ are as defined above. $R^{13}$, $R^{14}$, $R^{15}$, and $R^{16}$ are hydrogen atoms or $C_1$-$C_6$ hydrocarbon groups that may contain a heteroatom, and preferably hydrogen atoms. Examples of the $C_1$-$C_6$ hydrocarbon group that may contain a heteroatom include a methyl group, an ethyl group, a propyl group, an isopropyl group, a butyl group, a sec-butyl group, a tert-butyl group, a pentyl group, a hexyl group, a cyclohexyl group, a phenyl group, a 2-methoxyethyl group, a 2-ethoxyethyl group, a 2-(dimethylamino) ethyl group, and the like; and preferably a methyl group.

Specific examples include a 1,3-dimethylbenzimidazolium group, a 1-ethyl-3-methylbenzimidazolium group, a 1-methyl-3-propylbenzimidazolium group, a 1-methyl-3-isopropylbenzimidazolium group, a 1-butyl-3-methylbenzimidazolium group, a 1-tert-butyl-3-methylbenzimidazolium group, a 1-hexyl-3-methylbenzimidazolium group, a 1-methyl-3-octylbenzimidazolium group, a 1-dodecyl-3-methylbenzimidazolium group, a 1-allyl-3-methylbenzimidazolium group, a 1-benzyl-3-methylbenzimidazolium group, a 1,3-diethylbenzimidazolium group, a 1,3-dipropylbenzimidazolium group, a 1,3-diisopropylbenzimidazolium group, a 1,3-dibutylbenzimidazolium group, a 1,3-di-tert-butylbenzimidazolium group, a 1,3-dioctylbenzimidazolium group, a 1,3-diphenylbenzimidazolium group, a 1,3-bis(2,6-diisopropylphenyl)benzimidazolium group, a 1,3-dimesitylbenzimidazolium group, a 1,3,6-trimethylbenzimidazolium group, a 1-acetyl-3,6-dimethylbenzimidazolium group, a 1,3,6,7-tetramethylbenzimidazolium group, a 1,3-dibenzyl-6,7-dimethylbenzimidazolium group, and the like; preferably a 1,3-dimethylbenzimidazolium group, a 1-ethyl-3-methylbenzimidazolium group, a 1-methyl-3-propylbenzimidazolium group, and a 1-butyl-3-methylbenzimidazolium group; and particularly preferably a 1,3-dimethylbenzimidazolium group.

Examples of the iminium salt (1) include 1,3-dimethylimidazolium formate, 1-ethyl-3-methylimidazolium formate, 1-butyl-3-methylimidazolium formate, 1-methyl-3-octylimidazolium formate, 1-methyl-3-(2-ethylhexyl) imidazolium formate, 1-dodecyl-3-methylimidazolium formate, 1-methyl-3-octadecylimidazolium formate, 1-benzyl-3-methylimidazolium formate, 1,3-dibutylimidazolium formate, 1-butyl-3-ethylimidazolium formate, 1-butyl-3-octylimidazolium formate, 1-butyl-3-(2-ethylhexyl)imidazolium formate, 1-butyl-3-dodecylimidazolium formate, 1-butyl-3-octadecylimidazolium formate, 1-benzyl-3-butylimidazolium formate, 1,3-dioctylimidazolium formate, 1-ethyl-3-octylimidazolium formate, 1-octyl-3-(2-ethylhexyl)imidazolium formate, 1-dodecyl-3-octylimidazolium formate, 1-octyl-3-octadecylimidazolium formate, 1-benzyl-3-octylimidazolium formate, 1,3-bis(2-ethylhexyl)imidazolium formate, 1-ethyl-3-(2-ethylhexyl)imidazolium formate, 1-(2-ethylhexyl)-3-dodecylimidazolium formate, 1-(2-ethylhexyl)-3-octadecylimidazolium formate, 1-benzyl-3-(2-ethylhexyl)imidazolium formate, 1,3-didodecylimidazolium formate, 1-dodecyl-3-octadecylimidazolium formate, 1-benzyl-3-dodecylimidazolium formate, 1,3-dioctadecylimidazolium formate, 1-benzyl-3-octadecylimidazolium formate, 1,3-dibenzylimidazolium formate, 1,3-dimethylimidazolium acetate, 1-ethyl-3-methylimidazolium acetate, 1-butyl-3-methylimidazolium acetate, 1-methyl-3-octylimidazolium acetate, 1-methyl-3-(2-ethylhexyl)imidazolium acetate, 1-dodecyl-3-methylimidazolium acetate, 1-methyl-3-octadecylimidazolium acetate, 1-benzyl-3-methylimidazolium acetate, 1,3-dibutylimidazolium acetate, 1-butyl-3-ethylimidazolium acetate, 1-butyl-3-octylimidazolium acetate, 1-butyl-3-(2-ethylhexyl)imidazolium acetate, 1-butyl-3-dodecylimidazolium acetate, 1-butyl-3-octadecylimidazclium acetate, 1-benzyl-3-butylimidazolium acetate, 1,3-dioctylimidazolium acetate, 1-ethyl-3-octylimidazolium acetate, 1-octyl-3-(2-ethylhexyl)imidazolium acetate, 1-dodecyl-3-octylimidazolium acetate, 1-octyl-3-octadecylimidazolium acetate, 1-benzyl-3-octylimidazolium acetate, 1,3-bis(2-ethylhexyl)imidazolium acetate, 1-ethyl-3-(2-ethylhexyl)imidazolium acetate, 1-(2-ethylhexyl)-3-dodecylimidazolium acetate, 1-(2-ethylhexyl)-3-octadecylimidazolium acetate, 1-benzyl-3-(2-ethylhexyl)imidazolium acetate, 1,3-didodecylimidazolium acetate, 1-dodecyl-3-octadecylimidazolium acetate, 1-benzyl-3-dodecylimidazolium acetate, 1,3-dioctadecylimidazolium acetate, 1-benzyl-3-octadecylimidazolium acetate, 1,3-dibenzylimidazolium acetate, 1,3-dimethylimidazolium lactate, 1-ethyl-3-methylimidazolium lactate, 1-butyl-3-methylimidazolium lactate, 1-methyl-3-octylimidazolium lactate, 1-methyl-3-(2-ethylhexyl)imidazolium lactate, 1-dodecyl-3-methylimidazolium lactate, 1-methyl-3-octadecylimidazolium lactate, 1-benzyl-3-methylimidazolium lactate, 1,3-dibutylimidazolium lactate, 1-butyl-3-ethylimidazolium lactate, 1-butyl-3-octylimidazolium lactate, 1-butyl-3-(2-ethylhexyl)imidazolium lactate, 1-butyl-3-dodecylimidazolium lactate, 1-butyl-3-octadecylimidazolium lactate, 1-benzyl-3-butylimidazolium lactate, 1,3-dioctylimidazolium lactate, 1-ethyl-3-octylimidazolium lactate, 1-octyl-3-(2-ethylhexyl)imidazolium lactate, 1-dodecyl-3-octylimidazolium lactate, 1-octyl-3-octadecylimidazolium lactate, 1-benzyl-3-octylimidazolium lactate, 1,3-bis(2-ethylhexyl)imidazolium lactate, 1-ethyl-3-(2-ethylhexyl)imidazolium lactate, 1-(2-ethylhexyl)-3-dodecylimidazolium lactate, 1-(2-ethylhexyl)-3-octadecylimidazolium lactate, 1-benzyl-3-(2-ethylhexyl)imidazolium lactate, 1,3-didodecylimidazolium lactate, 1-dodecyl-3-octadecylimidazolium lactate, 1-benzyl-3-dodecylimidazolium lactate, 1,3-dioctadecylimidazolium lactate, 1-benzyl-3-octadecylimidazolium lactate, 1,3-dibenzylimidazolium lactate, 1,3-dimethylimidazolium hydrogen carbonate, 1-ethyl-3-methylimidazolium hydrogen carbonate, 1-butyl-3-methylimidazolium hydrogen carbonate, 1-methyl-3-octylimidazolium hydrogen carbonate, 1-methyl-3-(2-ethylhexyl) imidazolium hydrogen carbonate, 1-dodecyl-3-methylimidazolium hydrogen carbonate, 1-methyl-3-octadecylimidazolium hydrogen carbonate, 1-benzyl-3-methylimidazolium hydrogen carbonate, 1,3-dibutylimidazolium hydrogen carbonate, 1-butyl-3-ethylimidazolium hydrogen carbonate, 1-butyl-3-octylimidazolium hydrogen carbonate, 1-butyl-3-(2-ethylhexyl)imidazolium hydrogen carbonate, 1-butyl-3-dodecylimidazolium hydrogen carbonate, 1-butyl-3-octadecylimidazolium hydrogen carbonate, 1-benzyl-3-butylimidazolium hydrogen carbonate, 1,3-dioctylimidazolium hydrogen carbonate, 1-ethyl-3-octylimidazolium hydrogen carbonate, 1-octyl-3-(2-ethylhexyl)imidazolium hydrogen carbonate, 1-dodecyl-3- octylimidazolium hydrogen carbonate, 1-octyl-3-octadecylimidazolium hydrogen carbonate, 1-benzyl-3-octylimidazolium hydrogen carbonate, 1,3-bis(2-ethylhexyl)imidazolium hydrogen carbonate, 1-ethyl-3-(2-ethylhexyl)imidazolium hydrogen carbonate, 1-(2-ethylhexyl)-3-dodecylimidazolium hydrogen carbonate, 1-(2-ethylhexyl)-3-octadecylimidazolium hydrogen carbonate, 1-benzyl-3-(2-ethylhexyl)imidazolium hydrogen carbonate, 1,3-didodecylimidazolium hydrogen carbonate, 1-dodecyl-3-octadecylimidazolium hydrogen carbonate, 1-benzyl-3-dodecylimidazolium hydrogen carbonate, 1,3-dioctadecylimidazolium hydrogen carbonate, 1-benzyl-3-octadecylimidazolium hydrogen carbonate, 1,3-dibenzylimidazolium hydrogen carbonate,
1,3-dimethylimidazolium chloride, 1-ethyl-3-methylimidazolium chloride, 1-butyl-3-methylimidazolium chloride, 1-methyl-3-octylimidazolium chloride, 1-methyl-3-(2-ethylhexyl)imidazolium chloride, 1-dodecyl-3-methylimidazolium chloride, 1-methyl-3-octadecylimidazolium chloride, 1-benzyl-3-methylimidazolium chloride, 1,3-dibutylimidazolium chloride, 1-butyl-3-ethylimidazolium chloride, 1-butyl-3-octylimidazolium chloride, 1-butyl-3-(2-ethylhexyl)imidazolium chloride, 1-butyl-3-dodecylimidazolium chloride, 1-butyl-3-octadecylimidazolium chloride, 1-benzyl-3-butylimidazolium chloride, 1,3-dioctylimidazolium chloride, 1-ethyl-3-octylimidazolium chloride, 1-octyl-3-(2-ethylhexyl)imidazolium chloride, 1-dodecyl-3-octylimidazolium chloride, 1-octyl-3-octadecylimidazolium chloride, 1-benzyl-3-octylimidazolium chloride, 1,3-bis(2-ethylhexyl)imidazolium chloride, 1-ethyl-3-(2-ethylhexyl)imidazolium chloride, 1-(2-ethylhexyl)-3-dodecylimidazolium chloride, 1-(2-ethylhexyl)-3-octadecylimidazolium chloride, 1-benzyl-3-(2-ethylhexyl)imidazolium chloride, 1,3-didodecylimidazolium chloride, 1-dodecyl-3-octadecylimidazolium chloride, 1-benzyl-3-dodecylimidazolium chloride, 1,3-dioctadecylimidazolium chloride, 1-benzyl-3-octadecylimidazolium chloride, 1,3-dibenzylimidazolium chloride,
1,3-dimethylimidazolinium formate, 1,3-dimethylimidazolinium acetate, 1,3-dimethylimidazolinium lactate, 1,3-dimethylimidazolinium hydrogen carbonate, 1,3-dimethylimidazolinium chloride, 1-butyl-3-methylimidazolinium formate, 1-butyl-3-methylimidazolinium acetate, 1-butyl-3-methylimidazolinium lactate, 1-butyl-3-methylimidazolinium hydrogen carbonate, 1-butyl-3-methylimidazolinium chloride, 1-methyl-3-octylimidazolinium formate, 1-methyl-3-octylimidazolinium acetate, 1-methyl-3-octylimidazolinium lactate, 1-methyl-3-octylimidazolinium hydrogen carbonate, 1-methyl-3-octylimidazolinium chloride,
1,3-dimethylbenzimidazolium formate, 1,3-dimethylbenzimidazolium acetate, 1,3-dimethylbenzimidazolium lactate, 1,3-dimethylbenzimidazolium hydrogen carbonate, 1,3-dimethylbenzimidazolium chloride, and the like.

Preferable are 1,3-dimethylimidazolium acetate, 1-ethyl-3-methylimidazolium acetate, 1-butyl-3-methylimidazolium acetate, 1-methyl-3-octylimidazolium acetate, 1-methyl-3-(2-ethylhexyl)imidazolium acetate, 1-dodecyl-3-methylimidazolium acetate, 1-methyl-3-octadecylimidazolium acetate, 1-benzyl-3-methylimidazolium acetate, 1,3-dibutylimidazolium acetate, 1-butyl-3-ethylimidazolium acetate, 1-butyl-3-octylimidazolium acetate, 1-butyl-3-(2-ethylhexyl)imidazolium acetate, 1-butyl-3-dodecylimidazolium acetate, 1-butyl-3-octadecylimidazolium acetate, 1-benzyl-3-butylimidazolium acetate, 1,3-dioctylimidazolium acetate, 1-ethyl-3-octylimidazolium acetate, 1-octyl-3-(2-ethylhexyl)imidazolium acetate, 1-dodecyl-3-octylimidazolium acetate, 1-octyl-3-octadecylimidazolium acetate, 1-benzyl-3-octylimidazolium acetate, 1,3-bis(2-ethylhexyl)imidazolium acetate, 1-ethyl-3-(2-ethylhexyl)imidazolium acetate, 1-(2-ethylhexyl)-3-dodecylimidazolium acetate, 1-(2-ethylhexyl)-3-octadecylimidazolium acetate, 1-benzyl-3-(2-ethylhexyl)imidazolium acetate, 1,3-didodecylimidazolium acetate, 1-dodecyl-3-octadecylimidazolium acetate, 1-benzyl-3-dodecylimidazolium acetate, 1,3-dioctadecylimidazolium acetate, 1-benzyl-3-octadecylimidazolium acetate, and 1,3-dibenzylimidazolium acetate.

The iminium salt (1) may be a commercial product. The iminium salt (1) may be a salt obtained by a known method or a salt produced by a method explained below.

For example, when D in the iminium salt (1) is a nitrogen-containing organic group represented by Formula (2-1), this salt is preferably produced by a method explained below.

A dicarbonyl compound represented by the following Formula (6), primary amine compounds represented by the following Formulas (7a) and (7b), formaldehyde, and an acid represented by the following Formula (8) are allowed to react.

Formula (6):

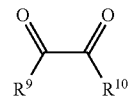

(6)

wherein $R^9$ and $R^{10}$ are as defined above.

Formula (7a):

$R^1-NH_2$ (7a)

wherein $R^1$ is as defined above.

Formula (7b):

$R^4-NH_2$ (7b)

wherein $R^4$ is as defined above.

Formula (8):

$G^-H^+$ (8)

wherein $G^-$ is as defined above.

In Formula (6), $R^9$ and $R^{10}$ are as defined above.

Examples of the dicarbonyl compound represented by Formula (6) (hereinafter referred to as "the dicarbonyl compound (6)") include glyoxal, diacetyl, 3,4-hexanedione, 2,3-pentanedione, 2,3-heptanedione, 5-methyl-2,3-hexanedione, 3-methyl-2,3-cyclopentanedione, 1,2-cyclohexanedione, 1-phenyl-1,2-propanedione, and dibenzoyl; preferably glyoxal and diacetyl; and more preferably glyoxal.

In Formula (7a), $R^1$ is as defined above.

In Formula (7b), $R^4$ is as defined above.

The primary amine compound represented by Formula (7a) (hereinafter referred to as "the primary amine compound (7a)") and the primary amine compound represented by Formula (7b) (hereinafter referred to as "the primary amine compound (7b)") are at least one primary amine compound selected from the group consisting of methylamine, ethylamine, propylamine, isopropylamine, butylamine, tert-butylamine, hexylamine, octylamine, 2-ethylhexylamine, dodecylamine, tetradecylamine, hexadecylamine, octadecylamine, allylamine, benzylamine, aniline, 2,6-diisopropylaniline, and 2,4,6-trimethylaniline; preferably methylamine, ethylamine, butylamine, hexylamine, octylamine, 2-ethylhexylamine, dodecylamine, octadecylamine, and benzylamine; and more preferably butylamine, octylamine, 2-ethylhexylamine, and benzylamine.

In Formula (8), $G^-$ is as defined above.

Examples of the acid represented by Formula (8) (hereinafter referred to as "the acid (8)") include carboxylic acids, such as formic acid, acetic acid, propionic acid, butyric acid, ethoxyacetic acid, propoxyacetic acid, 2-(2-methoxyethoxy) acetic acid, 2-(2-ethoxyethoxy)acetic acid, 2-(2-propoxyethoxy)acetic acid, 3-methoxypropanoic acid, 3-ethoxypropanoic acid, 3-(2-methoxyethoxy)propanoic acid, 3-(2-ethoxyethoxy)propanoic acid, 3-(2-propoxyethoxy) propanoic acid, 3-(3-methoxypropoxy)propanoic acid, 3-(3-ethoxypropoxy)propanoic acid, 3-(3-propoxypropoxy) propanoic acid, oleic acid, linoleic acid, sorbic acid, benzoic acid, phthalic acid, isophthalic acid, terephthalic acid, lactic acid, salicylic acid, and trifluoroacetic acid; hydrogen halides, such as hydrogen chloride, hydrogen bromide, and hydrogen iodide; sulfonic acids, such as methanesulfonic acid, trifluoromethanesulfonic acid, nonafluorobutanesulfonic acid, benzenesulfonic acid, and p-toluenesulfonic acid; phosphoric acids, such as dimethylphosphoric acid, diethylphosphoric acid, and dibutylphosphoric acid. Preferable are carboxylic acids, and more preferable is acetic acid.

As the dicarbonyl compound (6), an aqueous solution or an alcohol solution, such as methanol or butanol, may be used as it is.

The amounts of the primary amine compounds (7a) and (7b) used are generally such that the total amount of the primary amine compounds (7a) and (7b) is 0.1 to 10 mol, and preferably 0.5 to 3 mol, per mol of the dicarbonyl compound (6).

The ratio of the primary amine compound (7a) to the primary amine compound (7b) is not particularly limited, and is such that primary amine compound (7a):primary amine compound (7b)=0:100 to 100:0.

As the formaldehyde, an aqueous solution or an alcohol solution, such as methanol or butanol, may be used as it is. The amount of formaldehyde used is generally 0.1 to 10 mol, and preferably 0.5 to 5.0 mol, per mol of the dicarbonyl compound (6).

The amount of the acid (8) used is generally 0.1 to 10 mol, and preferably 0.5 to 2 mol, per mol of the dicarbonyl compound (6).

The optimal reaction temperature varies depending on the raw materials, solvents, etc., used, but is generally −10° C. or higher, and preferably 0° C. to 100° C.

A solvent may or may not be used. When a solvent is used, the solvent used is not particularly limited, as long as it does not affect the reaction. Specific examples of solvents include aromatic hydrocarbon solvents, such as toluene, benzene, and xylene; hydrocarbon solvents, such as methylcyclohexane, cyclohexane, hexane, heptane, and octane; halogenated hydrocarbon solvents, such as dichloromethane and chloroform; ether solvents, such as diethyl ether, tetrahydrofuran, and 1,4-dioxane; alcohol solvents, such as methanol and ethanol; N,N-dimethylformamide, acetonitrile, water, and the like. Preferred among these are aromatic hydrocarbon solvents, alcohol solvents, and water solvents; and particularly preferred are toluene and water. The solvents can be used as a mixture of two or more, if necessary.

The amount of solvent used is generally 50 parts by weight or less, and preferably 0.1 to 10 parts by weight, per part by weight of the dicarbonyl compound (6).

The reaction may be performed, if necessary, in an inert gas atmosphere, such as nitrogen, argon, or helium, which do not affect the reaction.

After completion of the reaction, the iminium salt (1) can be isolated, for example, by removing impurities (e.g., unreacted raw materials) by washing with an organic solvent, or concentrating the reaction liquid, and may be purified by recrystallization, etc., if necessary.

When $G^-$ of the iminium salt (1) obtained by the reaction is not the target anion, the desired anion may be obtained by an ion exchange reaction, if necessary.

The organic compound represented by Formula (3) (hereinafter referred to as "the organic compound (3)") is explained.

In Formula (3), A is a substituted or unsubstituted hydrocarbon group, preferably a substituted or unsubstituted $C_1$-$C_{100}$ hydrocarbon group, more preferably a substituted or unsubstituted $C_1$-$C_{50}$ hydrocarbon group, and particularly preferably a substituted or unsubstituted $C_1$-$C_{30}$ hydrocarbon group.

When A is a substituted hydrocarbon group, examples of substituents include halogen atoms, such as fluorine, chlorine, bromine, and iodine; alkylamino groups, such as methylamino; dialkylamino groups, such as dimethylamino; alkoxy groups, such as methoxy and ethoxy; aryloxy groups, such as benzyloxy; halogenated alkyl groups, such as trifluoromethyl; nitro groups, cyano groups, sulfonyl groups, (alkylamino)carbonylamino groups, (dialkylamino)carbonylamino groups, isocyanate groups, and the like. Moreover, the hydrocarbon group A may be substituted with a heteroatom, such as oxygen, nitrogen, or sulfur. When the hydrocarbon group A is substituted with a heteroatom, such as oxygen, nitrogen, or sulfur, the hydrocarbon group has a group, such as —O—, —NH—, or —S—, and the hydrocarbon chain is interrupted by such a group.

Examples of the alkyl moiety of the above alkylamino groups, dialkylamino groups, alkoxy groups, halogenated alkyl groups, (alkylamino)carbonylamino groups, and (dialkylamino)carbonylamino groups include linear or branched $C_1$-$C_6$ alkyl groups, such as methyl, ethyl, propyl, isopropyl, n-butyl, isobutyl, sec-butyl, tert-butyl, and pentyl. The number of carbon atoms in the alkyl group is preferably 1 to 3, and more preferably 1 or 2.

Examples of the aryl moiety of the above aryloxy groups include $C_6$-$C_{10}$ aryl groups. Specific examples include a phenyl group, a naphthyl group, and the like.

The number of substituents is 1 to 5, preferably 1 to 3, and more preferably 1 or 2.

In Formula (3), n is an integer of 1 or more, preferably 1 to 6, more preferably 1 to 4, and particularly preferably 1 or 2.

In Formula (3), Q is an —NCO group or an —NHCO$_2$R$^7$ group. R$^7$ is a hydrocarbon group that may contain a heteroatom, preferably a $C_1$-$C_{50}$ hydrocarbon group that may contain a heteroatom, more preferably a $C_1$-$C_{30}$ hydrocarbon group, and particularly preferably a $C_1$-$C_8$ hydrocarbon group. Examples of the hydrocarbon group that may contain a heteroatom include methyl, ethyl, propyl, isopropyl, butyl, sec-butyl, tert-butyl, pentyl, hexyl, octyl, decyl, dodecyl, allyl, benzyl, cyclohexyl, adamantyl, phenyl, 2,6-diisopropylphenyl, 2,4,6-trimethylphenyl, 2-methoxyethyl, 2-ethoxyethyl, 2-(dimethylamino)ethyl, and the like; preferably methyl, ethyl, propyl, isopropyl, tert-butyl, octyl, cyclopentyl, cyclohexyl, and 2,4,6-trimethylphenyl; more preferably methyl, ethyl, isopropyl, tert-butyl, octyl, and phenyl; and particularly preferably methyl, isopropyl, tert-butyl, octyl, and phenyl.

In the present invention, the organic compound (3) is preferably an organic compound represented by Formula (3-1), (3-2), or (3-3), and particularly preferably an organic compound represented by Formula (3-1).

Formula (3-1):

$$R^5\text{-}Q \qquad (3\text{-}1)$$

wherein Q is as defined above, and $R^5$ is a substituted or unsubstituted hydrocarbon group.

Formula (3-2):

$$Q\text{-}R^6\text{-}Q \qquad (3\text{-}2)$$

wherein Q is as defined above, and $R^6$ is a substituted or unsubstituted hydrocarbon group.

Formula (3-3):

(3-3)

[Chemical structure with (Q)$_a$, Q, (Q)$_b$, CH$_2$ linkages, $(E^1)_c$, $(E^2)_d$, $(E^3)_e$, f, g subscripts]

wherein Q is as defined above; $E^1$, $E^2$, and $E^3$ are each independently a substituted or unsubstituted hydrocarbon group, a halogen atom, an alkylamino group, a dialkylamino group, an alkoxy group, an aryloxy group, a nitro group, a cyano group, a sulfonyl group, an (alkylamino)carbonylamino group, a (dialkylamino)carbonylamino group, or an isocyanate group; f and g are each independently an integer of 0 to 4; a and b are 0 or 1; and c, d, and e are each independently an integer of 0 to 4; provided that when f is 0, at least one of a or b is 1.

When Q is an —NCO group, the organic compound (3) is an isocyanate compound represented by the following Formula (3a) (hereinafter referred to as "the isocyanate compound (3a)"). When Q is an —NHCO$_2$R$^7$ group, the organic compound (3) is a urethane compound represented by the following Formula (3b) (hereinafter referred to as "the urethane compound (3b)").

Formula (3a):

$$A\text{-}[\text{NCO}]_n \qquad (3a)$$

wherein A and n are as defined above.

Formula (3b):

(3b)

$$A\text{-}\left[\text{NH}\overset{\overset{O}{\|}}{\text{C}}\text{-}O\text{-}R^7\right]_n$$

wherein A, n, and $R^7$ are as defined above.

In Formulas (3-1), (3-2), and (3-3), when Q is an —NCO group, the organic compounds represented by Formulas (3-1), (3-2), and (3-3) have structures represented by Formulas (3a-1), (3a-2), and (3a-3), respectively.

Formula (3a-1):

$$R^5\text{—NCO} \qquad (3a\text{-}1)$$

wherein $R^5$ is as defined above.

Formula (3a-2):

$$\text{OCN—}R^6\text{—NCO} \qquad (3a\text{-}2)$$

wherein $R^6$ is as defined above.

Formula (3a-3):

(3a-3)

[Chemical structure with (NCO)$_a$, NCO, (NCO)$_b$, CH$_2$ linkages, $(E^1)_c$, $(E^2)_d$, $(E^3)_e$, f, g subscripts]

wherein $E^1$, $E^2$, $E^3$, a, b, c, d, e, f, and g are as defined above.

In the present invention, a polymer such as polymethylene polyphenyl polyisocyanate (polymeric MDI) can also be used as the isocyanate compound (3a).

In Formula (3a-1), $R^5$ is a substituted or unsubstituted hydrocarbon group, preferably a substituted or unsubstituted $C_1$-$C_{50}$ hydrocarbon group, more preferably a substituted or unsubstituted $C_1$-$C_{30}$ hydrocarbon group, and particularly preferably a substituted or unsubstituted $C_1$-$C_{12}$ hydrocarbon group. Specific examples include a methyl group, an ethyl group, a propyl group, an isopropyl group, a butyl group, a sec-butyl group, a tert-butyl group, a pentyl group, a hexyl group, a heptyl group, a decyl group, a dodecyl group, an octadecyl group, a cyclopropyl group, a cyclopentyl group, a cyclohexyl group, a phenyl group, a naphthyl group, a benzyl group, a phenethyl group, a tolyl group, an allyl group, and the like; and preferably a benzyl group and a phenyl group.

When $R^5$ is substituted, examples of substituents include halogen atoms, such as fluorine, chlorine, bromine, and iodine; alkylamino groups, such as methylamino; dialkylamino groups, such as dimethylamino; alkoxy groups, such as methoxy and ethoxy; aryloxy groups, such as benzyloxy; halogenated alkyl groups, such as trifluoromethyl; nitro groups, cyano groups, sulfonyl groups, (alkylamino)carbonylamino groups, (dialkylamino)carbonylamino groups, isocyanate groups, and the like. Moreover, the hydrocarbon group $R^5$ may be substituted with a heteroatom, such as oxygen, nitrogen, or sulfur. When the hydrocarbon group is substituted with a heteroatom, such as oxygen, nitrogen, or sulfur, the hydrocarbon group has a group, such as —O—, —NH—, or —S—, and the hydrocarbon chain is interrupted by such a group.

Examples of the alkyl moiety of the above alkylamino groups, dialkylamino groups, alkoxy groups, halogenated alkyl groups, (alkylamino)carbonylamino groups, and (dialkylamino)carbonylamino groups include linear or branched $C_1$-$C_6$ alkyl groups, such as methyl, ethyl, propyl, isopropyl, butyl, sec-butyl, tert-butyl, and pentyl. The number of carbon atoms in the alkyl group is preferably 1 to 3, and more preferably 1 or 2.

Examples of the aryl moiety of the above aryloxy groups include $C_6$-$C_{10}$ aryl groups. Specific examples include a phenyl group, a naphthyl group, and the like.

The number of substituents is 1 to 5, preferably 1 to 3, and more preferably 1 or 2.

In Formula (3a-2), $R^6$ is a substituted or unsubstituted hydrocarbon group, preferably a substituted or unsubstituted $C_1$-$C_{100}$ hydrocarbon group, more preferably a substituted or unsubstituted $C_1$-$C_{50}$ hydrocarbon group, and particularly preferably a substituted or unsubstituted $C_1$-$C_{30}$ hydrocarbon group. Specific examples include alkylene groups, such as a methylene group, a dimethylmethylene group, an ethylene group, an n-propylene group, an n-butylene group, an n-pentylene group, an n-hexylene group, an n-heptylene group, an n-octylene group, an n-nonylene group, an n-decylene group, an n-dodecylene group, an n-octadecylene group, and a cyclohexylene group; allylene groups, such as a phenylene group, a 2-methylphenylene group, a 2,6-dimethylphenylene group, a 2,4-dimethylphenylene group, a 2,3-dimethylphenylene group, and a naphthylene group; arylalkylene groups, such as a phenylmethylene group, a phenylethylene group, a 1-phenylpropylene group, a 2-phenylpropylene group, a 1-phenylbutylene group, 2-phenylbutylene group, a naphthylmethylene group, and a naphthylethylene group; arylenealkylene groups obtained by suitably combining the above alkylene groups and allylene groups; and the like. These divalent hydrocarbon groups may be repeated or combined to constitute one divalent hydrocarbon group.

When $R^6$ is substituted, examples of substituents include halogen atoms, such as fluorine, chlorine, bromine, and iodine; alkylamino groups, such as methylamino; dialkylamino groups, such as dimethylamino; alkoxy groups, such as methoxy and ethoxy; aryloxy groups, such as benzyloxy; halogenated alkyl groups, such as trifluoromethyl; nitro groups, cyano groups, sulfonyl groups, (alkylamino)carbonylamino groups, (dialkylamino)carbonylamino groups, isocyanate groups, and the like. Moreover, the hydrocarbon group $R^5$ may be substituted with a heteroatom, such as oxygen, nitrogen, or sulfur. When the hydrocarbon group is substituted with a heteroatom, such as oxygen, nitrogen, or sulfur, the hydrocarbon group has a group, such as —O—, —NH—, or —S—, and the hydrocarbon chain is interrupted by such a group.

Examples of the alkyl moiety of the above alkylamino groups, dialkylamino groups, alkoxy groups, halogenated alkyl groups, (alkylamino)carbonylamino groups, and (dialkylamino)carbonylamino groups include linear or branched $C_1$-$C_6$ alkyl groups, such as methyl, ethyl, propyl, isopropyl, butyl, sec-butyl, tert-butyl, and pentyl. The number of carbon atoms in the alkyl group is preferably 1 to 3, and more preferably 1 or 2.

Examples of the aryl moiety of the above aryloxy groups include $C_6$-$C_{10}$ aryl groups. Specific examples include a phenyl group, a naphthyl group, and the like.

The number of substituents is 1 to 5, preferably 1 to 3, and more preferably 1 or 2.

In Formula (3a-3), $E^1$, $E^2$, and $E^3$ are each independently a substituted or unsubstituted hydrocarbon group, a halogen atom, an alkylamino group, a dialkylamino group, an alkoxy group, an aryloxy group, a nitro group, a cyano group, a sulfonyl group, an (alkylamino)carbonylamino group, a (dialkylamino)carbonylamino group, or an isocyanate group; preferably a substituted or unsubstituted hydrocarbon group, an (alkylamino)carbonylamino group, a (dialkylamino)carbonylamino group, or an isocyanate group; and more preferably an (alkylamino)carbonylamino group or a (dialkylamino)carbonylamino group.

f and g are each independently an integer of 0 to 4. a and b are 0 or 1, and c, d, and e are each independently an integer of 0 to 4, provided that when f is 0, at least one of a or b is 1.

When a compound represented by Formula (3a-1) or (3a-2), wherein $R^5$ or $R^6$ is a hydrocarbon group having an (alkylamino)carbonylamino group or a (dialkylamino)carbonylamino group, is used as the isocyanate compound (3a), for example, some of the isocyanate groups in the isocyanate compound having a plurality of isocyanate groups represented by Formula (3a-2) or (3a-3) are reacted with a primary amine compound, a secondary amine compound, or the like to form an (alkylamino)carbonylamino group or a (dialkylamino)carbonylamino group, which can be used as the isocyanate compound (3a).

In Formula (3a-3), when $E^1$, $E^2$, and $E^3$ are each an (alkylamino)carbonylamino group or a (dialkylamino)carbonylamino group, for example, some of the isocyanate groups in the polymer, such as polymethylene polyphenyl polyisocyanate, are reacted with a primary amine compound or a secondary amine compound to form an (alkylamino)carbonylamino group or a (dialkylamino)carbonylamino group, which can be used as the isocyanate compound (3a).

Examples of primary amine compounds include methylamine, ethylamine, propylamine, isopropylamine, butylamine, sec-butylamine, tert-butylamine, pentylamine, hexylamine, octylamine, decylamine, dodecylamine, 2-ethylhexylamine, and the like; and preferably butylamine and 2-ethylhexylamine. Examples of secondary amine compounds include dimethylamine, diethylamine, dipropylamine, diisopropylamine, dibutylamine, di(sec-butyl)amine, di(tert-butyl)amine, dipentylamine, dihexylamine, dioctylamine, didecylamine, methylethylamine, didodecylamine, di(2-ethylhexyl)amine, and the like; and preferably dibutylamine and di(2-ethylhexyl)amine.

Specific examples of the isocyanate compound (3a) are shown below. However, the present invention is not limited thereto. In the following specific examples, Et represents an ethyl group, Pr represents an n-propyl group, and Bu represents an n-butyl group.

R—NCO

| R = | CH₃ | (3a-1-1) |
|---|---|---|
| | CH₂CH₃ | (3a-1-2) |
| | (CH₂)₃CH₂ | (3a-1-3) |
| | CH(CH₂)₂ | (3a-1-4) |
| | (CH₂)₃CH₃ | (3a-1-5) |
| | C(CH₃)₂ | (3a-1-6) |
| | (CH₂)₇CH₂ | (3a-1-7) |
| | (CH₂)₈CH₂ | (3a-1-8) |
| | (CH₂)₉CH₂ | (3a-1-9) |
| | (CH₂)₁₀CH₂ | (3a-1-10) |
| | (CH₂)₁₁CH₂ | (3a-1-11) |

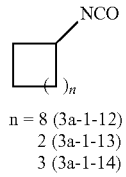

n = 8 (3a-1-12)
  2 (3a-1-13)
  3 (3a-1-14)

-continued
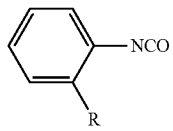
| R = H | (3a-1-15) |
| --- | --- |
| CH₃ | (3a-1-16) |
| (CH₂)₂CH₃ | (3a-1-17) |
| (CH₂)₃CH₃ | (3a-1-18) |
| OCH₂ | (3a-1-19) |
| F | (3a-1-20) |
| Cl | (3a-1-21) |
| Br | (3a-1-22) |
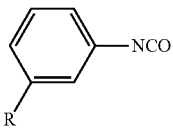
| R = CH₃ | (3a-1-23) |
| --- | --- |
| (CH₂)₂CH₃ | (3a-1-24) |
| (CH₂)₃CH₃ | (3a-1-25) |
| OCH₂ | (3a-1-26) |
| F | (3a-1-27) |
| Cl | (3a-1-28) |
| Br | (3a-1-29) |
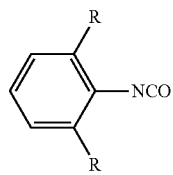
| R = CH₃ | (3a-1-40) |
| --- | --- |
| (CH₂)₃CH₃ | (3a-1-41) |
| (CH₂)₇CH₃ | (3a-1-42) |
| CH(CH₂)₃ | (3a-1-43) |
| C(CH₂)₃ | (3a-1-44) |
| F | (3a-1-45) |
| Cl | (3a-1-46) |
| Br | (3a-1-47) |
| R = CH₃ | (3a-1-30) |
| --- | --- |
| (CH₂)₃CH₃ | (3a-1-31) |
| (CH₂)₇CH₃ | (3a-1-32) |
| OCH₂ | (3a-1-33) |
| CH(CH₂)₃ | (3a-1-34) |
| C(CH₂)₃ | (3a-1-35) |
| N(CH₂)₂ | (3a-1-36) |
| F | (3a-1-37) |
| Cl | (3a-1-38) |
| Br | (3a-1-39) |
(3a-1-56)
| R = CH₃ | (3a-1-48) |
| --- | --- |
| (CH₂)₃CH₃ | (3a-1-49) |
| (CH₂)₇CH₃ | (3a-1-50) |
| CH(CH₂)₃ | (3a-1-51) |
| C(CH₂)₃ | (3a-1-52) |
| F | (3a-1-53) |
| Cl | (3a-1-54) |
| Br | (3a-1-55) |
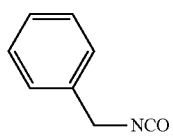
(3a-1-57)
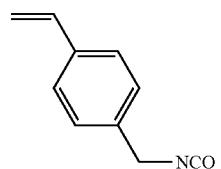
(3a-1-58)
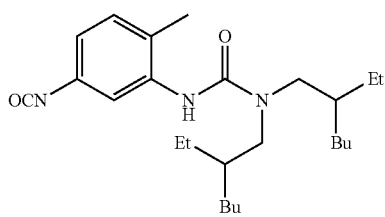
(3a-1-58)
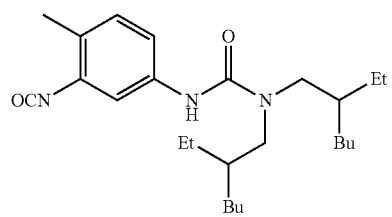
(3a-1-59)
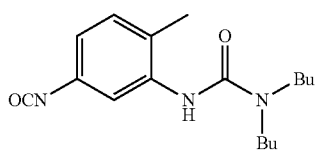
(3a-1-60)
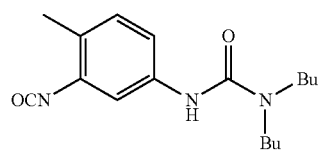
(3a-1-61)

(3a-1-62)
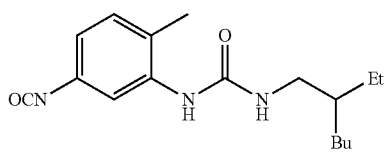
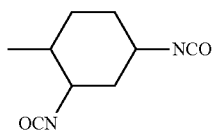
R = —CH₂CH₂— (3a-2-1)
—CH₂(CH₂)₂CH₂— (3a-2-2)
—CH₂(CH₂)₄CH₂— (3a-2-3)
—CH₂(CH₂)₆CH₂— (3a-2-4)
—CH₂(CH₂)₈CH₂— (3a-2-5)
—CH₂(CH₂)₁₀CH₂— (3a-2-6)
(3a-2-9)
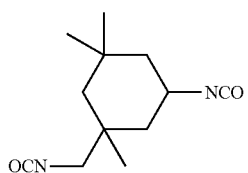
(3a-2-12)
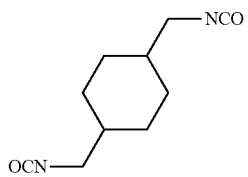
(3a-2-15)
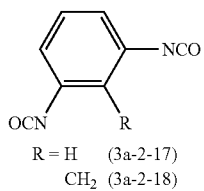
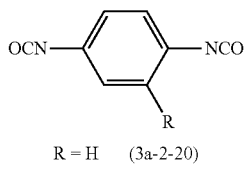
R = H (3a-2-17)
CH₂ (3a-2-18)
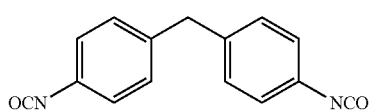
R = H (3a-2-20)
CH₂ (3a-2-21)
-continued
(3a-1-63)
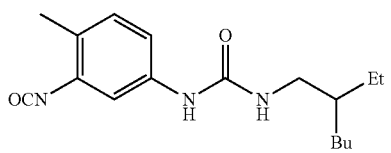
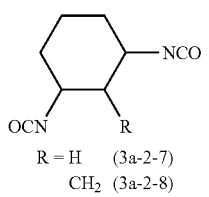
R = H (3a-2-7)
CH₂ (3a-2-8)
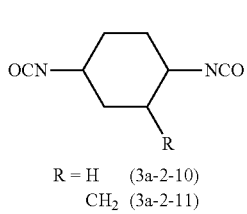
R = H (3a-2-10)
CH₂ (3a-2-11)
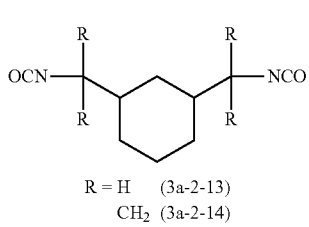
R = H (3a-2-13)
CH₂ (3a-2-14)
(3a-2-16)
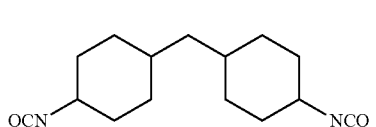
(3a-2-19)
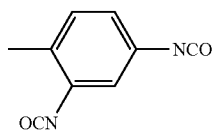
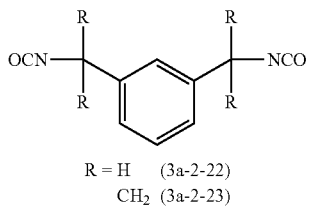
R = H (3a-2-22)
CH₂ (3a-2-23)
(3a-2-24)

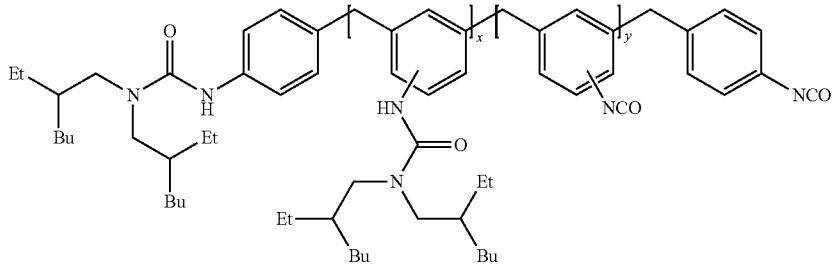

(3a-3-1)

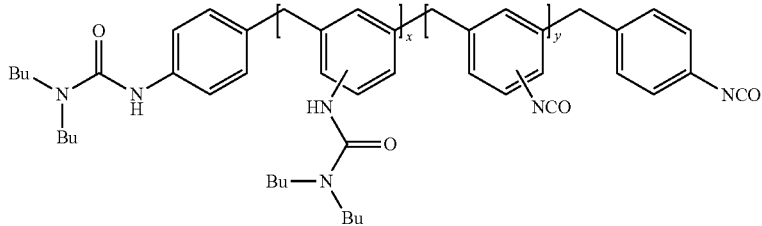

(3a-3-2)

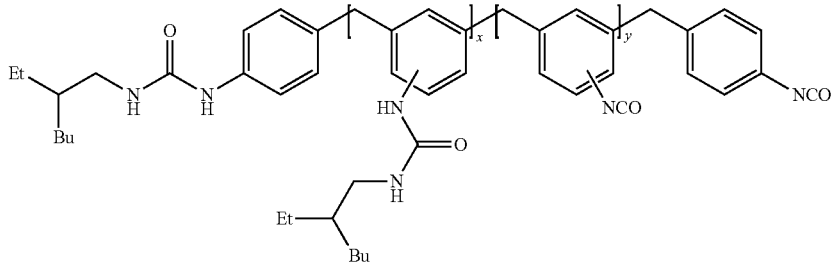

(3a-3-3)

The isocyanate compound (3a) is preferably a compound represented by Formula (3a-1-5), (3a-1-15), (3a-1-38), or (3a-2-19); and particularly preferably a compound represented by Formula (3a-1-15).

The isocyanate compounds (3a) may be used singly or as a mixture of two or more.

In Formulas (3-1), (3-2), and (3-3), when Q is an —NHCO$_2$R$^7$ group, the organic compounds represented by Formulas (3-1), (3-2), and (3-3) have structures represented by Formulas (3b-1), (3b-2), and (3b-3), respectively.

Formula (3b-1):

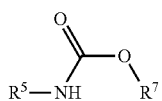

(3b-1)

wherein R$^5$ and R$^7$ are as defined above.

Formula (3b-2):

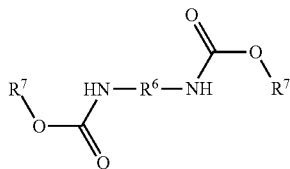

(3b-2)

wherein R$^6$ and R$^7$ are as defined above.

Formula (3b-3):

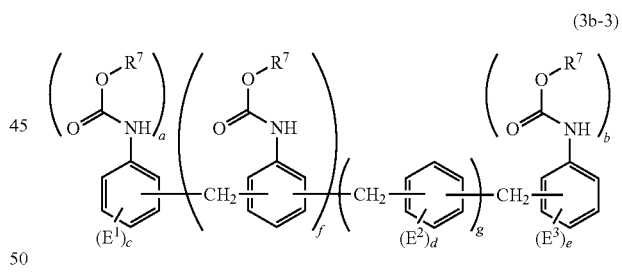

(3b-3)

wherein R$^7$, E$^1$, E$^2$, E$^3$, a, b, c, d, e, f, and g are as defined above.

In Formula (3b-1), R$^5$ and R$^7$ are as defined above.

In Formula (3b-2), R$^6$ and R$^7$ are as defined above.

In Formula (3b-3), R$^7$, E$^1$, E$^2$, E$^3$, a, b, c, d, e, f, and g are as defined above.

Specific examples of the urethane compound (3b) are shown below. However, the present invention is not limited thereto. In the following specific examples, Et represents an ethyl group, Pr represents an n-propyl group, and Bu represents an n-butyl group.

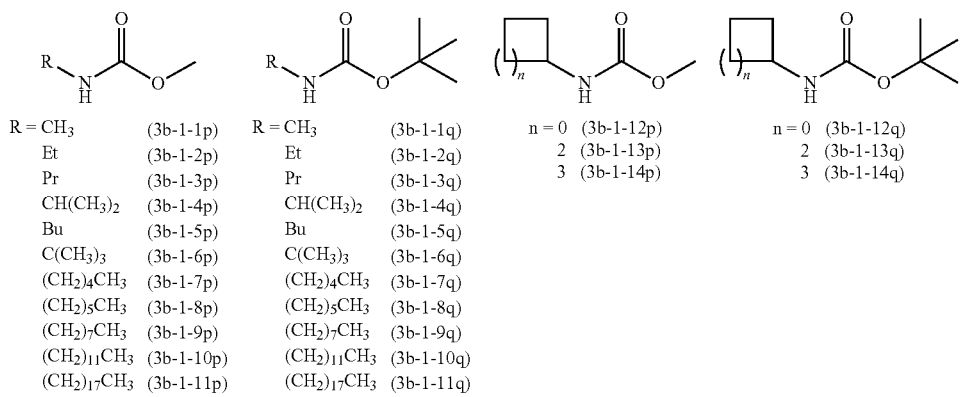

| R = CH₃ | (3b-1-1p) | R = CH₃ | (3b-1-1q) | n = 0 | (3b-1-12p) | n = 0 | (3b-1-12q) |
| Et | (3b-1-2p) | Et | (3b-1-2q) | 2 | (3b-1-13p) | 2 | (3b-1-13q) |
| Pr | (3b-1-3p) | Pr | (3b-1-3q) | 3 | (3b-1-14p) | 3 | (3b-1-14q) |
| CH(CH₃)₂ | (3b-1-4p) | CH(CH₃)₂ | (3b-1-4q) | | | | |
| Bu | (3b-1-5p) | Bu | (3b-1-5q) | | | | |
| C(CH₃)₃ | (3b-1-6p) | C(CH₃)₃ | (3b-1-6q) | | | | |
| (CH₂)₄CH₃ | (3b-1-7p) | (CH₂)₄CH₃ | (3b-1-7q) | | | | |
| (CH₂)₅CH₃ | (3b-1-8p) | (CH₂)₅CH₃ | (3b-1-8q) | | | | |
| (CH₂)₇CH₃ | (3b-1-9p) | (CH₂)₇CH₃ | (3b-1-9q) | | | | |
| (CH₂)₁₁CH₃ | (3b-1-10p) | (CH₂)₁₁CH₃ | (3b-1-10q) | | | | |
| (CH₂)₁₇CH₃ | (3b-1-11p) | (CH₂)₁₇CH₃ | (3b-1-11q) | | | | |

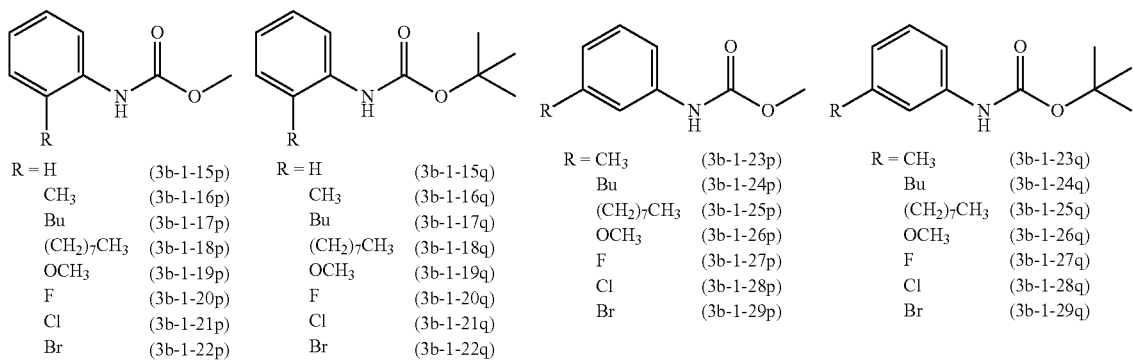

| R = H | (3b-1-15p) | R = H | (3b-1-15q) | R = CH₃ | (3b-1-23p) | R = CH₃ | (3b-1-23q) |
| CH₃ | (3b-1-16p) | CH₃ | (3b-1-16q) | Bu | (3b-1-24p) | Bu | (3b-1-24q) |
| Bu | (3b-1-17p) | Bu | (3b-1-17q) | (CH₂)₇CH₃ | (3b-1-25p) | (CH₂)₇CH₃ | (3b-1-25q) |
| (CH₂)₇CH₃ | (3b-1-18p) | (CH₂)₇CH₃ | (3b-1-18q) | OCH₃ | (3b-1-26p) | OCH₃ | (3b-1-26q) |
| OCH₃ | (3b-1-19p) | OCH₃ | (3b-1-19q) | F | (3b-1-27p) | F | (3b-1-27q) |
| F | (3b-1-20p) | F | (3b-1-20q) | Cl | (3b-1-28p) | Cl | (3b-1-28q) |
| Cl | (3b-1-21p) | Cl | (3b-1-21q) | Br | (3b-1-29p) | Br | (3b-1-29q) |
| Br | (3b-1-22p) | Br | (3b-1-22q) | | | | |

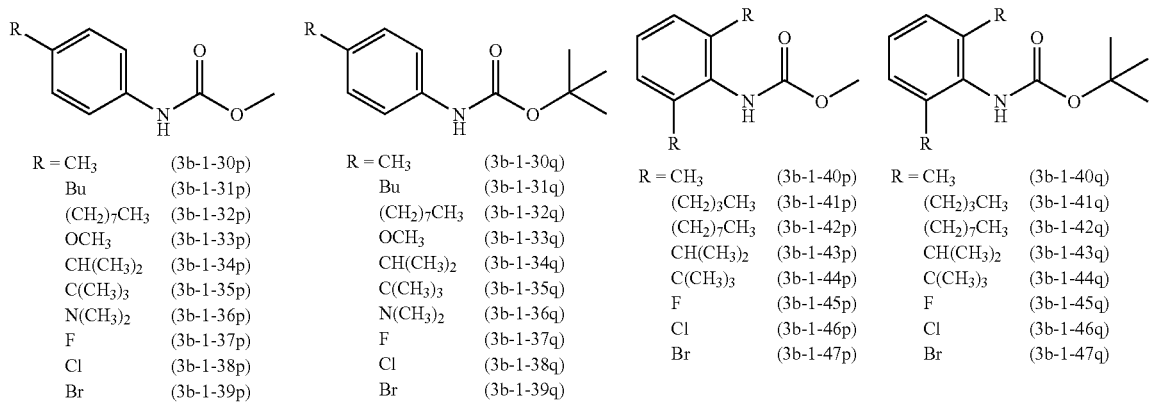

| R = CH₃ | (3b-1-30p) | R = CH₃ | (3b-1-30q) | R = CH₃ | (3b-1-40p) | R = CH₃ | (3b-1-40q) |
| Bu | (3b-1-31p) | Bu | (3b-1-31q) | (CH₂)₃CH₃ | (3b-1-41p) | (CH₂)₃CH₃ | (3b-1-41q) |
| (CH₂)₇CH₃ | (3b-1-32p) | (CH₂)₇CH₃ | (3b-1-32q) | (CH₂)₇CH₃ | (3b-1-42p) | (CH₂)₇CH₃ | (3b-1-42q) |
| OCH₃ | (3b-1-33p) | OCH₃ | (3b-1-33q) | CH(CH₃)₂ | (3b-1-43p) | CH(CH₃)₂ | (3b-1-43q) |
| CH(CH₃)₂ | (3b-1-34p) | CH(CH₃)₂ | (3b-1-34q) | C(CH₃)₃ | (3b-1-44p) | C(CH₃)₃ | (3b-1-44q) |
| C(CH₃)₃ | (3b-1-35p) | C(CH₃)₃ | (3b-1-35q) | F | (3b-1-45p) | F | (3b-1-45q) |
| N(CH₃)₂ | (3b-1-36p) | N(CH₃)₂ | (3b-1-36q) | Cl | (3b-1-46p) | Cl | (3b-1-46q) |
| F | (3b-1-37p) | F | (3b-1-37q) | Br | (3b-1-47p) | Br | (3b-1-47q) |
| Cl | (3b-1-38p) | Cl | (3b-1-38q) | | | | |
| Br | (3b-1-39p) | Br | (3b-1-39q) | | | | |

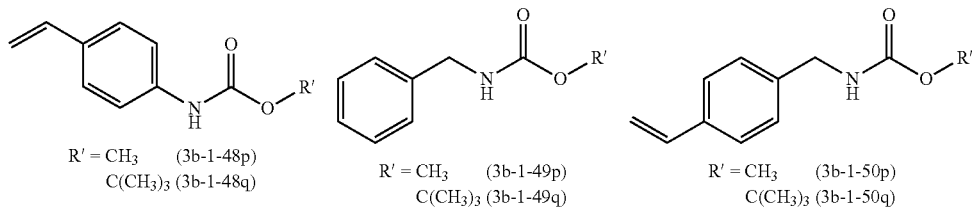

| R' = CH₃ | (3b-1-48p) | R' = CH₃ | (3b-1-49p) | R' = CH₃ | (3b-1-50p) |
| C(CH₃)₃ | (3b-1-48q) | C(CH₃)₃ | (3b-1-49q) | C(CH₃)₃ | (3b-1-50q) |

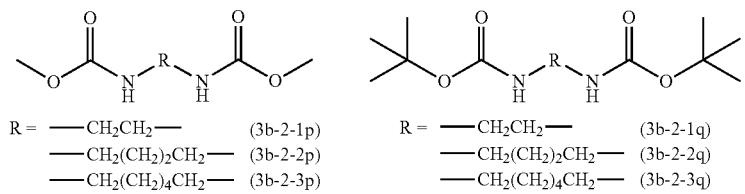

| R = —CH₂CH₂— | (3b-2-1p) | R = —CH₂CH₂— | (3b-2-1q) |
| —CH₂(CH₂)₂CH₂— | (3b-2-2p) | —CH₂(CH₂)₂CH₂— | (3b-2-2q) |
| —CH₂(CH₂)₄CH₂— | (3b-2-3p) | —CH₂(CH₂)₄CH₂— | (3b-2-3q) |

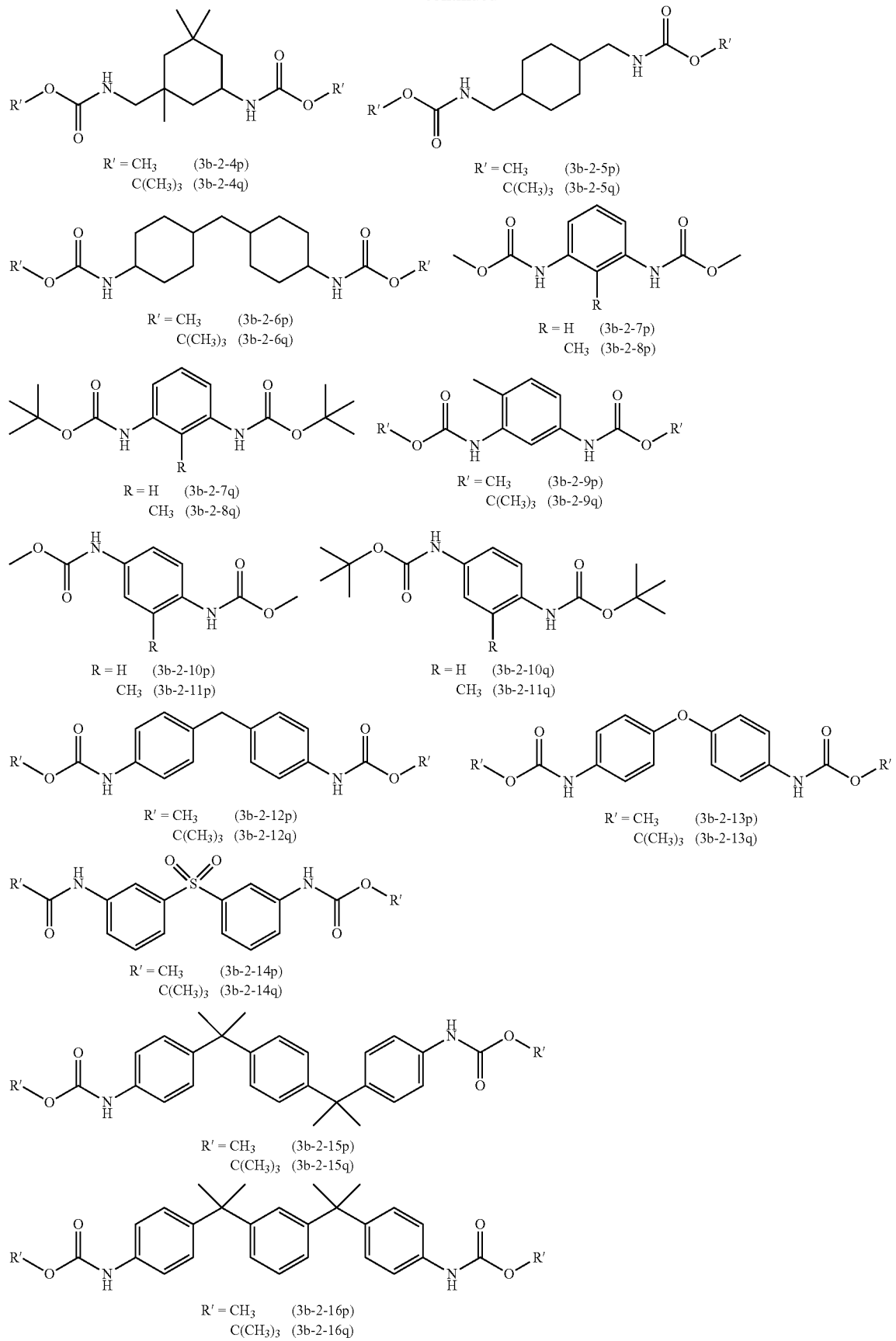

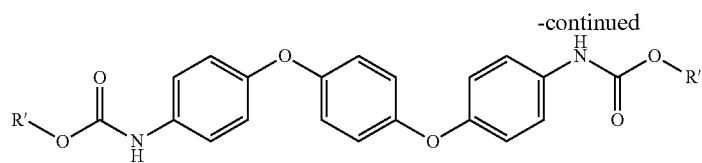

R' = CH₃ (3b-2-17p)
C(CH₃)₃ (3b-2-17q)

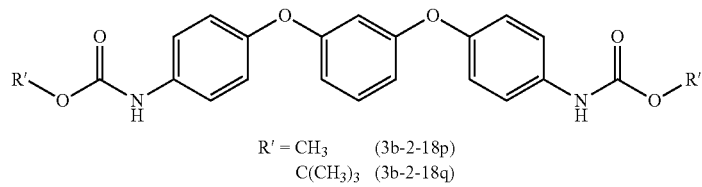

R' = CH₃ (3b-2-18p)
C(CH₃)₃ (3b-2-18q)

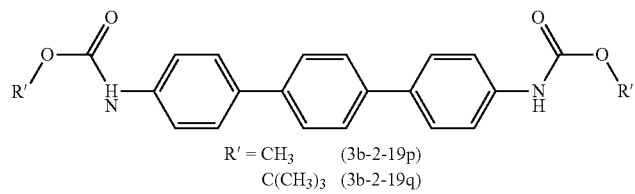

R' = CH₃ (3b-2-19p)
C(CH₃)₃ (3b-2-19q)

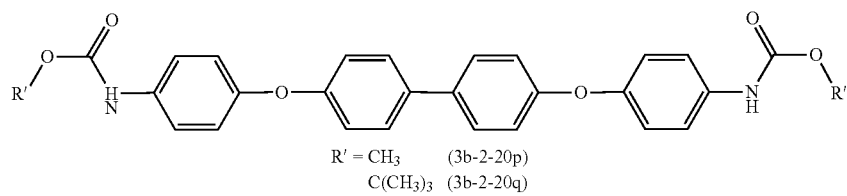

R' = CH₃ (3b-2-20p)
C(CH₃)₃ (3b-2-20q)

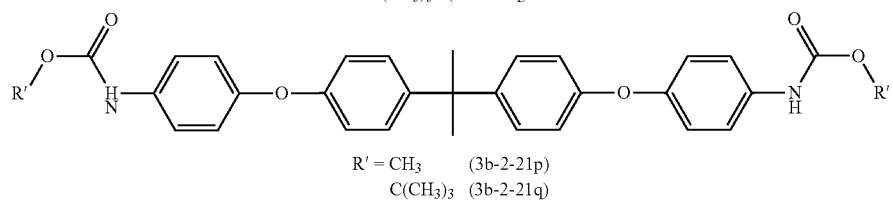

R' = CH₃ (3b-2-21p)
C(CH₃)₃ (3b-2-21q)

Preferable examples of the urethane compound (3b) include compounds represented by Formulas (3b-1-15p), (3b-1-15q), (3b-1-21p), (3b-1-21q), (3b-1-28p), (3b-1-28q), (3b-1-32p), (3b-1-32q), (3b-1-33p), (3b-1-33q), (3b-1-34p), (3b-1-34q), (3b-1-38p), (3b-1-38q), (3b-1-43p), (3b-1-43q), (3b-1-48p), (3b-1-48q), (3b-1-49p), (3b-1-49q), (3b-1-50p), (3b-1-50q), (3b-2-12p), (3b-2-12q), (3b-2-14p), (3b-2-14q), (3b-2-15p), (3b-2-15q), (3b-2-16p), (3b-2-16q), (3b-2-18p), and (3b-2-18q); and particularly preferably a compound represented by Formula (3b-1-15p).

The urethane compound (3b) used as a raw material may be a commercial product, or may be produced by a known method.

The amidate compound represented by Formula (4) (hereinafter referred to as "the amidate compound (4)") is explained.

In Formula (4), A, D, and, n are as defined above.

The amidate compound (4) is preferably an amidate compound represented by Formula (4-1), (4-2), or (4-3), and particularly preferably an amidate compound represented by Formula (4-1).

Formula (4-1):

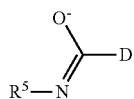

(4-1)

wherein $R^5$ and D are as defined above.

Formula (4-2):

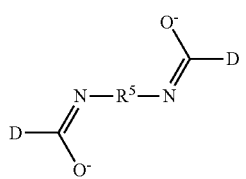

(4-2)

wherein $R^6$ and D are as defined above.

Formula (4-3):

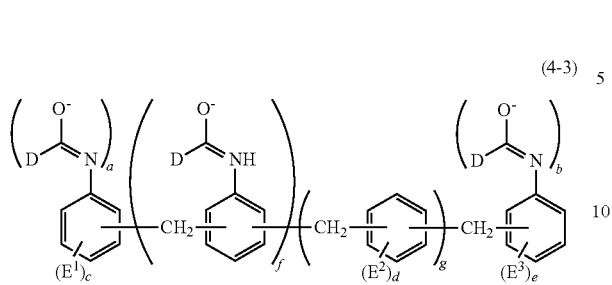

wherein D, $E^1$, $E^2$, $E^3$, a, b, c, d, e, f, and g are as defined above.

In Formula (4-1), $R^5$ and D are as defined above.

In Formula (4-2), $R^6$ and D are as defined above.

In Formula (4-3), D, $E^1$, $E^2$, $E^3$, a, b, c, d, e, f, and g are as defined above.

Next, specific examples of the amidate compound (4) are shown below. However, the present invention is not limited thereto. In the following specific examples, Et represents an ethyl group, Pr represents an n-propyl group, and Bu represents an n-butyl group.

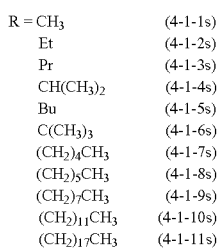

| R = | | |
|---|---|---|
| CH₃ | | (4-1-1s) |
| Et | | (4-1-2s) |
| Pr | | (4-1-3s) |
| CH(CH₃)₂ | | (4-1-4s) |
| Bu | | (4-1-5s) |
| C(CH₃)₃ | | (4-1-6s) |
| (CH₂)₄CH₃ | | (4-1-7s) |
| (CH₂)₅CH₃ | | (4-1-8s) |
| (CH₂)₇CH₃ | | (4-1-9s) |
| (CH₂)₁₁CH₃ | | (4-1-10s) |
| (CH₂)₁₇CH₃ | | (4-1-11s) |

 (4-1-12s)

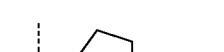 (4-1-13s)

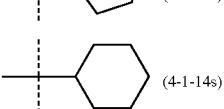 (4-1-14s)

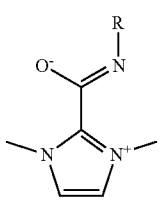

| R = CH₃ | (4-1-1r) |
|---|---|
| Et | (4-1-2r) |
| Pr | (4-1-3r) |
| CH(CH₃)₂ | (4-1-4r) |
| Bu | (4-1-5r) |
| C(CH₃)₃ | (4-1-6r) |
| (CH₂)₄CH₃ | (4-1-7r) |
| (CH₂)₅CH₃ | (4-1-8r) |
| (CH₂)₇CH₃ | (4-1-9r) |
| (CH₂)₁₁CH₃ | (4-1-10r) |
| (CH₂)₁₇CH₃ | (4-1-11r) |

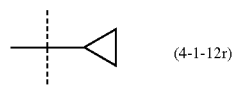 (4-1-12r)

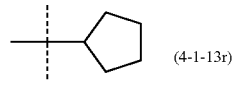 (4-1-13r)

 (4-1-14r)

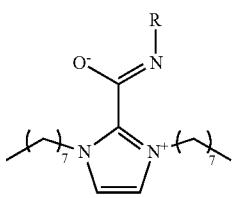

| R = CH₃ | (4-1-1t) |
|---|---|
| Et | (4-1-2t) |
| Pr | (4-1-3t) |
| CH(CH₃)₂ | (4-1-4t) |
| Bu | (4-1-5t) |
| C(CH₃)₃ | (4-1-6t) |
| (CH₂)₄CH₃ | (4-1-7t) |
| (CH₂)₅CH₃ | (4-1-8t) |
| (CH₂)₇CH₃ | (4-1-9t) |
| (CH₂)₁₁CH₃ | (4-1-10t) |
| (CH₂)₁₇CH₃ | (4-1-11t) |

 (4-1-12t)

 (4-1-13t)

 (4-1-14t)

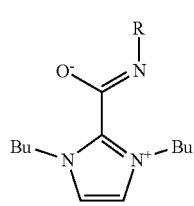

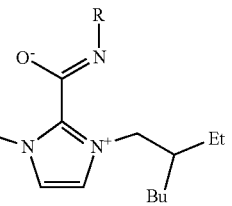

| R = | | |
|---|---|---|
| CH₃ | | (4-1-1u) |
| Et | | (4-1-2u) |
| Pr | | (4-1-3u) |
| CH(CH₃)₂ | | (4-1-4u) |
| Bu | | (4-1-5u) |
| C(CH₃)₃ | | (4-1-6u) |
| (CH₂)₄CH₃ | | (4-1-7u) |
| (CH₂)₅CH₃ | | (4-1-8u) |
| (CH₂)₇CH₃ | | (4-1-9u) |
| (CH₂)₁₁CH₃ | | (4-1-10u) |
| (CH₂)₁₇CH₃ | | (4-1-11u) |

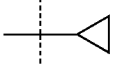 (4-1-12u)

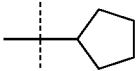 (4-1-13u)

 (4-1-14u)

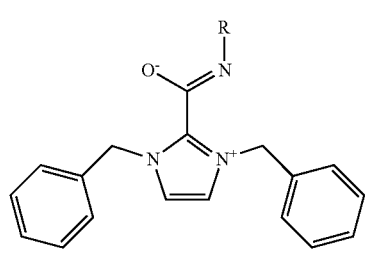

| R = | | |
|---|---|---|
| CH₃ | | (4-1-1v) |
| Et | | (4-1-2v) |
| Pr | | (4-1-3v) |
| CH(CH₃)₂ | | (4-1-4v) |
| Bu | | (4-1-5v) |
| C(CH₃)₃ | | (4-1-6v) |
| (CH₂)₄CH₃ | | (4-1-7v) |
| (CH₂)₅CH₃ | | (4-1-8v) |
| (CH₂)₇CH₃ | | (4-1-9v) |
| (CH₂)₁₁CH₃ | | (4-1-10v) |
| (CH₂)₁₇CH₃ | | (4-1-11v) |

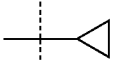 (4-1-12v)

 (4-1-13v)

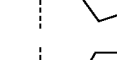 (4-1-14v)

| R' | R'' | |
|---|---|---|
| CH₃ | CH₃ | (4-1-15r) |
| CH₃ | Et | (4-1-15ab) |
| CH₃ | Pr | (4-1-15ac) |
| CH₃ | CH(CH₃)₂ | (4-1-15ad) |
| CH₃ | Bu | (4-1-15ae) |
| CH₃ | C(CH₃)₃ | (4-1-15af) |
| CH₃ | (CH₂)₅CH₃ | (4-1-15ah) |
| CH₃ | (CH₂)₇CH₃ | (4-1-15ai) |
| CH₃ | CH₂CH(Et)Bu | (4-1-15aj) |
| CH₃ | (CH₂)₁₁CH₃ | (4-1-15ak) |
| CH₃ | (CH₂)₁₇CH₃ | (4-1-15al) |
| CH₃ | CH₂Ph | (4-1-15am) |
| CH₃ | Ph | (4-1-15an) |
| Et | Et | (4-1-15bb) |
| Et | Pr | (4-1-15bc) |
| Et | CH(CH₃)₂ | (4-1-15bd) |
| Et | Bu | (4-1-15be) |
| Et | C(CH₃)₃ | (4-1-15bf) |
| Et | (CH₂)₅CH₃ | (4-1-15bh) |
| Et | (CH₂)₇CH₃ | (4-1-15bi) |
| Et | CH₂CH(Et)Bu | (4-1-15bj) |
| Et | (CH₂)₁₁CH₃ | (4-1-15bk) |
| Et | (CH₂)₁₇CH₃ | (4-1-15bl) |
| Et | CH₂Ph | (4-1-15bm) |
| Et | Ph | (4-1-15bn) |
| Pr | Pr | (4-1-15cc) |
| Pr | CH(CH₃)₂ | (4-1-15cd) |
| Pr | Bu | (4-1-15ce) |
| Pr | C(CH₃)₃ | (4-1-15cf) |
| Pr | (CH₂)₅CH₃ | (4-1-15ch) |
| Pr | (CH₂)₇CH₃ | (4-1-15ci) |
| Pr | CH₂CH(Et)Bu | (4-1-15cj) |
| Pr | (CH₂)₁₁CH₃ | (4-1-15ck) |
| Pr | (CH₂)₁₇CH₃ | (4-1-15cl) |
| Pr | CH₂Ph | (4-1-15cm) |
| Pr | Ph | (4-1-15cn) |
| Bu | CH(CH₃)₂ | (4-1-15ed) |
| Bu | Bu | (4-1-15s) |
| Bu | C(CH₃)₃ | (4-1-15ef) |
| Bu | (CH₂)₅CH₃ | (4-1-15eh) |
| Bu | (CH₂)₇CH₃ | (4-1-15ei) |
| Bu | CH₂CH(Et)Bu | (4-1-15ej) |
| Bu | (CH₂)₁₁CH₃ | (4-1-15ek) |
| Bu | (CH₂)₁₇CH₃ | (4-1-15el) |
| Bu | CH₂Ph | (4-1-15em) |
| Bu | Ph | (4-1-15en) |
| (CH₂)₅CH₃ | CH(CH₃)₂ | (4-1-15hd) |
| (CH₂)₅CH₃ | C(CH₃)₃ | (4-1-15hf) |
| (CH₂)₅CH₃ | (CH₂)₅CH₃ | (4-1-15hh) |
| (CH₂)₅CH₃ | (CH₂)₇CH₃ | (4-1-15hi) |
| (CH₂)₅CH₃ | CH₂CH(Et)Bu | (4-1-15hj) |
| (CH₂)₅CH₃ | (CH₂)₁₁CH₃ | (4-1-15hk) |
| (CH₂)₅CH₃ | (CH₂)₁₇CH₃ | (4-1-15hl) |
| (CH₂)₅CH₃ | CH₂Ph | (4-1-15hm) |
| (CH₂)₅CH₃ | Ph | (4-1-15hn) |
| (CH₂)₇CH₃ | CH(CH₃)₂ | (4-1-15hd) |
| (CH₂)₇CH₃ | C(CH₃)₃ | (4-1-15hf) |
| (CH₂)₇CH₃ | (CH₂)₇CH₃ | (4-1-15t) |
| (CH₂)₇CH₃ | CH₂CH(Et)Bu | (4-1-15ij) |
| (CH₂)₇CH₃ | (CH₂)₁₁CH₃ | (4-1-15ik) |
| (CH₂)₇CH₃ | (CH₂)₁₇CH₃ | (4-1-15il) |
| (CH₂)₇CH₃ | CH₂Ph | (4-1-15im) |
| (CH₂)₇CH₃ | Ph | (4-1-15in) |
| CH₂CH(Et)Bu | CH(CH₃)₂ | (4-1-15jd) |
| CH₂CH(Et)Bu | C(CH₃)₃ | (4-1-15jf) |

-continued

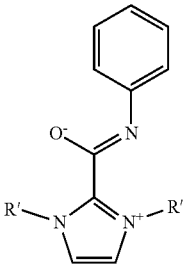

| R' | R'' | |
|---|---|---|
| CH₂CH(Et)Bu | CH₂CH(Et)Bu | (4-1-15u) |
| CH₂CH(Et)Bu | (CH₂)₁₁CH₃ | (4-1-15jk) |
| CH₂CH(Et)Bu | (CH₂)₁₇CH₃ | (4-1-15jl) |
| CH₂CH(Et)Bu | CH₂Ph | (4-1-15jm) |
| CH₂CH(Et)Bu | Ph | (4-1-15jn) |
| (CH₂)₁₁CH₃ | CH(CH₃)₂ | (4-1-15kd) |
| (CH₂)₁₁CH₃ | C(CH₃)₃ | (4-1-15kf) |
| (CH₂)₁₁CH₃ | (CH₂)₁₁CH₃ | (4-1-15kk) |
| (CH₂)₁₁CH₃ | (CH₂)₁₇CH₃ | (4-1-15kl) |
| (CH₂)₁₁CH₃ | CH₂Ph | (4-1-15km) |
| (CH₂)₁₁CH₃ | Ph | (4-1-15kn) |
| (CH₂)₁₇CH₃ | CH(CH₃)₂ | (4-1-15ld) |
| (CH₂)₁₇CH₃ | C(CH₃)₃ | (4-1-15lf) |
| (CH₂)₁₇CH₃ | (CH₂)₁₇CH₃ | (4-1-15ll) |
| (CH₂)₁₇CH₃ | CH₂Ph | (4-1-15lm) |
| (CH₂)₁₇CH₃ | Ph | (4-1-15ln) |
| CH₂Ph | CH(CH₃)₂ | (4-1-15md) |
| CH₂Ph | C(CH₃)₃ | (4-1-15mf) |
| CH₂Ph | CH₂Ph | (4-1-15v) |
| CH₂Ph | Ph | (4-1-15mn) |
| Ph | CH(CH₃)₂ | (4-1-15nd) |
| Ph | C(CH₃)₃ | (4-1-15nf) |
| Ph | Ph | (4-1-15nn) |

| R | R' | |
|---|---|---|
| CH₃ | CH₃ | (4-1-16r) |
| CH₃ | Bu | (4-1-16s) |
| CH₃ | (CH₂)₇CH₃ | (4-1-16t) |
| CH₃ | CH₂CH(Et)Bu | (4-1-16u) |
| CH₃ | CH₂Ph | (4-1-16v) |
| Bu | CH₃ | (4-1-17r) |
| Bu | Bu | (4-1-17s) |
| Bu | (CH₂)₇CH₃ | (4-1-17t) |
| Bu | CH₂CH(Et)Bu | (4-1-17u) |
| Bu | CH₂Ph | (4-1-17v) |
| (CH₂)₇CH₃ | CH₃ | (4-1-18r) |
| (CH₂)₇CH₃ | Bu | (4-1-18s) |
| (CH₂)₇CH₃ | (CH₂)₇CH₃ | (4-1-18t) |
| (CH₂)₇CH₃ | CH₂CH(Et)Bu | (4-1-18u) |
| (CH₂)₇CH₃ | CH₂Ph | (4-1-18v) |
| OCH₃ | CH₃ | (4-1-19r) |
| OCH₃ | Bu | (4-1-19s) |
| OCH₃ | (CH₂)₇CH₃ | (4-1-19t) |
| OCH₃ | CH₂CH(Et)Bu | (4-1-19u) |

-continued

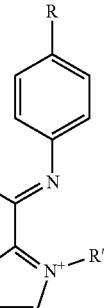

| R | R' | |
|---|---|---|
| OCH₃ | CH₂Ph | (4-1-19v) |
| OEt | CH₃ | (4-1-20r) |
| OEt | Bu | (4-1-20s) |
| OEt | (CH₂)₇CH₃ | (4-1-20t) |
| OEt | CH₂CH(Et)Bu | (4-1-20u) |
| OEt | CH₂Ph | (4-1-20v) |
| CH(CH₃)₂ | CH₃ | (4-1-21r) |
| CH(CH₃)₂ | Bu | (4-1-21s) |
| CH(CH₃)₂ | (CH₂)₇CH₃ | (4-1-21t) |
| CH(CH₃)₂ | CH₂CH(Et)Bu | (4-1-21u) |
| CH(CH₃)₂ | CH₂Ph | (4-1-21v) |
| C(CH₃)₃ | CH₃ | (4-1-22r) |
| C(CH₃)₃ | Bu | (4-1-22s) |
| C(CH₃)₃ | (CH₂)₇CH₃ | (4-1-22t) |
| C(CH₃)₃ | CH₂CH(Et)Bu | (4-1-22u) |
| C(CH₃)₃ | CH₂Ph | (4-1-22v) |
| F | CH₃ | (4-1-23r) |
| F | Bu | (4-1-23s) |
| F | (CH₂)₇CH₃ | (4-1-23t) |
| F | CH₂CH(Et)Bu | (4-1-23u) |
| F | CH₂Ph | (4-1-23v) |
| Cl | CH₃ | (4-1-24r) |
| Cl | Bu | (4-1-24s) |
| Cl | (CH₂)₇CH₃ | (4-1-24t) |
| Cl | CH₂CH(Et)Bu | (4-1-24u) |
| Cl | CH₂Ph | (4-1-24v) |
| Br | CH₃ | (4-1-25r) |
| Br | Bu | (4-1-25s) |
| Br | (CH₂)₇CH₃ | (4-1-25t) |
| Br | CH₂CH(Et)Bu | (4-1-25u) |
| Br | CH₂Ph | (4-1-25v) |

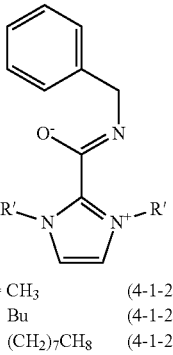 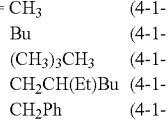

| R' = CH₃ | (4-1-26r) | R' = CH₃ | (4-1-27r) |
| Bu | (4-1-26s) | Bu | (4-1-27s) |
| (CH₃)₃CH₃ | (4-1-26t) | (CH₂)₇CH₈ | (4-1-27t) |
| CH₂CH(Et)Bu | (4-1-26u) | CH₂CH(Et)Bu | (4-1-27u) |
| CH₂Ph | (4-1-26v) | CH₂Ph | (4-1-27v) |

-continued

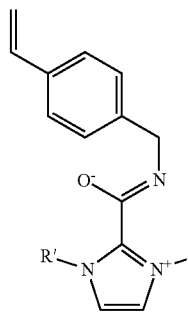

| R′ = CH₃ | (4-1-28r) |
|---|---|
| Bu | (4-1-28s) |
| (CH₂)₇CH₈ | (4-1-28t) |
| CH₂CH(Et)Bu | (4-1-28u) |
| CH₂Ph | (4-1-28v) |

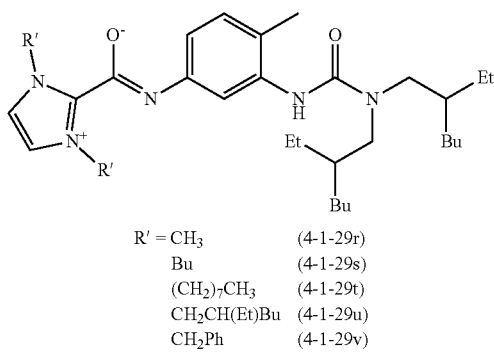

| R′ = CH₃ | (4-1-29r) |
|---|---|
| Bu | (4-1-29s) |
| (CH₂)₇CH₃ | (4-1-29t) |
| CH₂CH(Et)Bu | (4-1-29u) |
| CH₂Ph | (4-1-29v) |

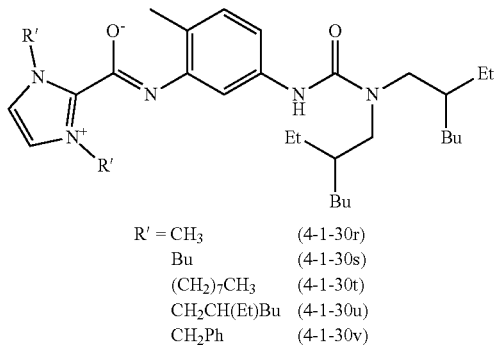

| R′ = CH₃ | (4-1-30r) |
|---|---|
| Bu | (4-1-30s) |
| (CH₂)₇CH₃ | (4-1-30t) |
| CH₂CH(Et)Bu | (4-1-30u) |
| CH₂Ph | (4-1-30v) |

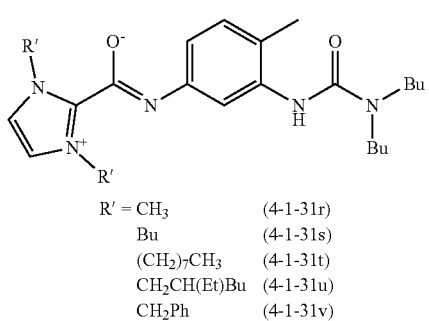

| R′ = CH₃ | (4-1-31r) |
|---|---|
| Bu | (4-1-31s) |
| (CH₂)₇CH₃ | (4-1-31t) |
| CH₂CH(Et)Bu | (4-1-31u) |
| CH₂Ph | (4-1-31v) |

-continued

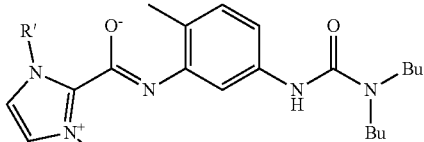

| R′ = CH₃ | (4-1-32r) |
|---|---|
| Bu | (4-1-32s) |
| (CH₂)₇CH₃ | (4-1-32t) |
| CH₂CH(Et)Bu | (4-1-32u) |
| CH₂Ph | (4-1-32v) |

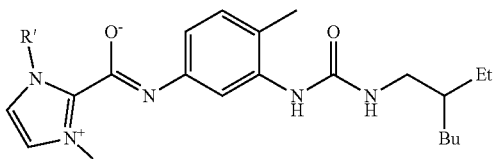

| R′ = CH₃ | (4-1-33r) |
|---|---|
| Bu | (4-1-33s) |
| (CH₂)₇CH₃ | (4-1-33t) |
| CH₂CH(Et)Bu | (4-1-33u) |
| CH₂Ph | (4-1-33v) |

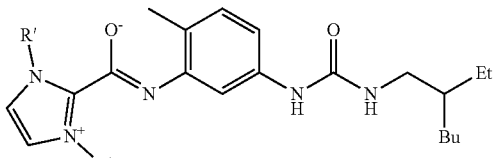

| R′ = CH₃ | (4-1-34r) |
|---|---|
| Bu | (4-1-34s) |
| (CH₂)₇CH₃ | (4-1-34t) |
| CH₂CH(Et)Bu | (4-1-34u) |
| CH₂Ph | (4-1-34v) |

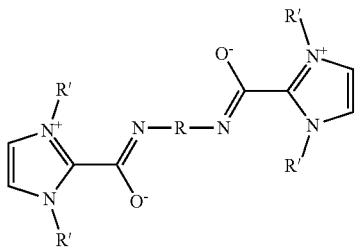

| R | R′ | |
|---|---|---|
| —CH₂CH₂— | CH₃ | (4-2-1r) |
| —CH₂CH₂— | Bu | (4-2-1s) |
| —CH₂CH₂— | (CH₂)₇CH₃ | (4-2-1t) |
| —CH₂CH₂— | CH₂CH(Et)Bu | (4-2-1u) |
| —CH₂CH₂— | CH₂Ph | (4-2-2v) |
| —CH₂(CH₂)₂CH₂— | CH₃ | (4-2-2r) |
| —CH₂(CH₂)₂CH₂— | Bu | (4-2-2s) |
| —CH₂(CH₂)₂CH₂— | (CH₂)₇CH₃ | (4-2-2t) |
| —CH₂(CH₂)₂CH₂— | CH₂CH(Et)Bu | (4-2-2u) |
| —CH₂(CH₂)₂CH₂— | CH₂Ph | (4-2-2v) |
| —CH₂(CH₂)₄CH₂— | CH₃ | (4-2-3r) |
| —CH₂(CH₂)₄CH₂— | Bu | (4-2-3s) |
| —CH₂(CH₂)₄CH₂— | (CH₂)₇CH₃ | (4-2-3t) |
| —CH₂(CH₂)₄CH₂— | CH₂CH(Et)Bu | (4-2-3u) |
| —CH₂(CH₂)₄CH₂— | CH₂Ph | (4-2-3v) |
| —CH₂(CH₂)₆CH₂— | CH₃ | (4-2-4r) |
| —CH₂(CH₂)₆CH₂— | Bu | (4-2-4s) |
| —CH₂(CH₂)₆CH₂— | (CH₂)₇CH₃ | (4-2-4t) |

43
-continued

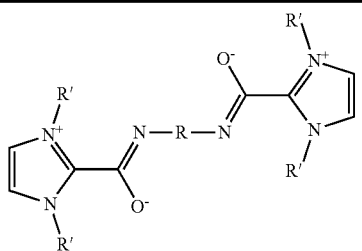

| R | R' | |
|---|---|---|
| —CH$_2$(CH$_2$)$_6$CH$_2$— | CH$_2$CH(Et)Bu | (4-2-4u) |
| —CH$_2$(CH$_2$)$_6$CH$_2$— | CH$_2$Ph | (4-2-4v) |
| —CH$_2$(CH$_2$)$_8$CH$_2$— | CH$_3$ | (4-2-5r) |
| —CH$_2$(CH$_2$)$_8$CH$_2$— | Bu | (4-2-5s) |
| —CH$_2$(CH$_2$)$_8$CH$_2$— | (CH$_2$)$_7$CH$_3$ | (4-2-5t) |
| —CH$_2$(CH$_2$)$_8$CH$_2$— | CH$_2$CH(Et)Bu | (4-2-5u) |
| —CH$_2$(CH$_2$)$_8$CH$_2$— | CH$_2$Ph | (4-2-5v) |

44
-continued

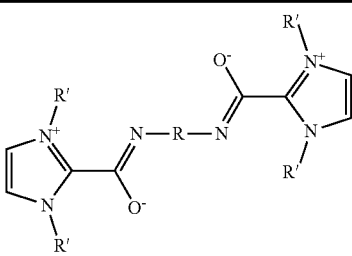

| R | R' | |
|---|---|---|
| —CH$_2$(CH$_2$)$_{10}$CH$_2$— | CH$_3$ | (4-2-6r) |
| —CH$_2$(CH$_2$)$_{10}$CH$_2$— | Bu | (4-2-6s) |
| —CH$_2$(CH$_2$)$_{10}$CH$_2$— | (CH$_2$)$_7$CH$_3$ | (4-2-6t) |
| —CH$_2$(CH$_2$)$_{10}$CH$_2$— | CH$_2$CH(Et)Bu | (4-2-6u) |
| —CH$_2$(CH$_2$)$_{10}$CH$_2$— | CH$_2$Ph | (4-2-6v) |

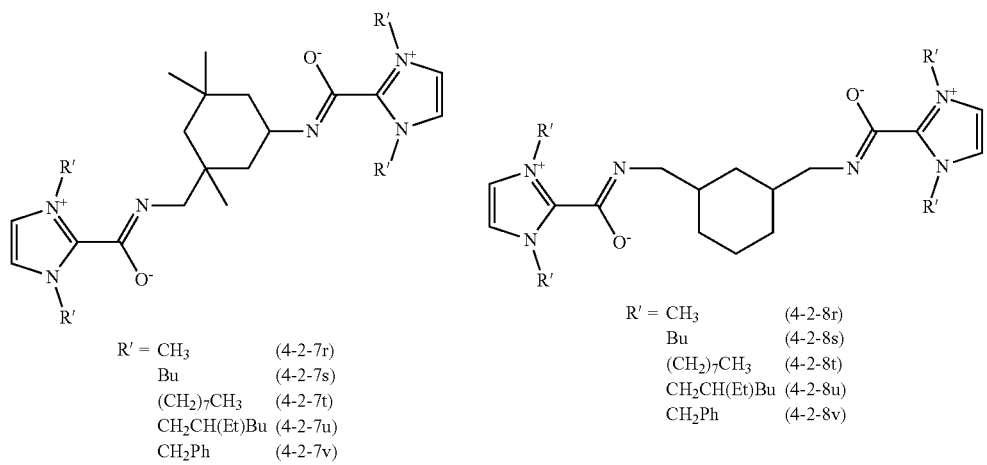

R' = CH$_3$ (4-2-7r)
Bu (4-2-7s)
(CH$_2$)$_7$CH$_3$ (4-2-7t)
CH$_2$CH(Et)Bu (4-2-7u)
CH$_2$Ph (4-2-7v)

R' = CH$_3$ (4-2-8r)
Bu (4-2-8s)
(CH$_2$)$_7$CH$_3$ (4-2-8t)
CH$_2$CH(Et)Bu (4-2-8u)
CH$_2$Ph (4-2-8v)

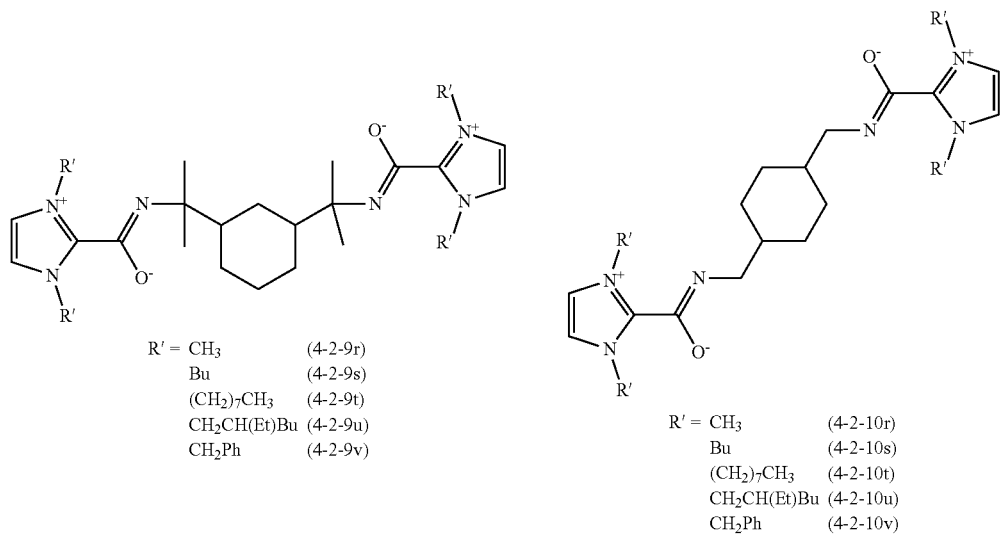

R' = CH$_3$ (4-2-9r)
Bu (4-2-9s)
(CH$_2$)$_7$CH$_3$ (4-2-9t)
CH$_2$CH(Et)Bu (4-2-9u)
CH$_2$Ph (4-2-9v)

R' = CH$_3$ (4-2-10r)
Bu (4-2-10s)
(CH$_2$)$_7$CH$_3$ (4-2-10t)
CH$_2$CH(Et)Bu (4-2-10u)
CH$_2$Ph (4-2-10v)

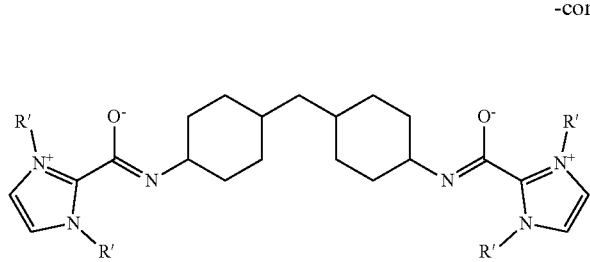
R' = CH₃ (4-2-11r)
Bu (4-2-11s)
(CH₂)₇CH₃ (4-2-11t)
CH₂CH(Et)Bu (4-2-11u)
CH₂Ph (4-2-11v)
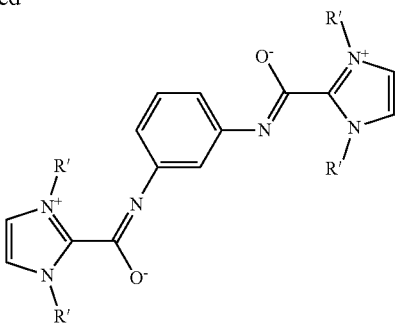
R' = CH₃ (4-2-12r)
Bu (4-2-12s)
(CH₂)₇CH₃ (4-2-12t)
CH₂CH(Et)Bu (4-2-12u)
CH₂Ph (4-2-12v)
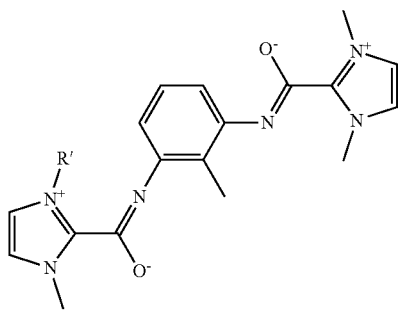
R' = CH₃ (4-2-13r)
Bu (4-2-13s)
(CH₂)₇CH₃ (4-2-13t)
CH₂CH(Et)Bu (4-2-13u)
CH₂Ph (4-2-13v)
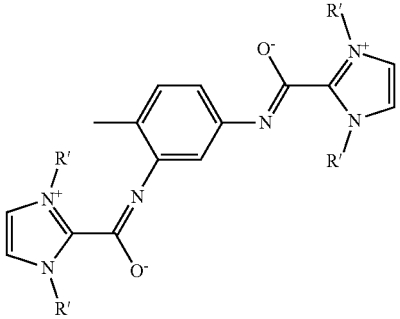
R' = CH₃ (4-2-14r)
Bu (4-2-14s)
(CH₂)₇CH₃ (4-2-14t)
CH₂CH(Et)Bu (4-2-14u)
CH₂Ph (4-2-14v)
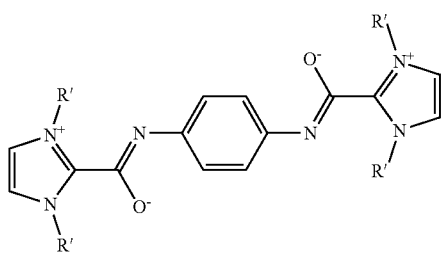
R' = CH₃ (4-2-15r)
Bu (4-2-15s)
(CH₂)₇CH₃ (4-2-15t)
CH₂CH(Et)Bu (4-2-15u)
CH₂Ph (4-2-15v)
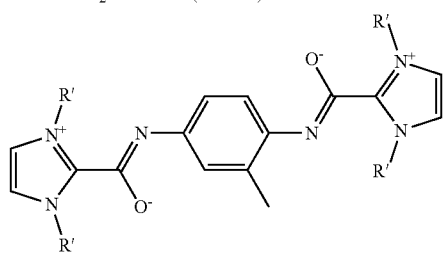
R' = CH₃ (4-2-16r)
Bu (4-2-16s)
(CH₂)₇CH₃ (4-2-16t)
CH₂CH(Et)Bu (4-2-16u)
CH₂Ph (4-2-16v)
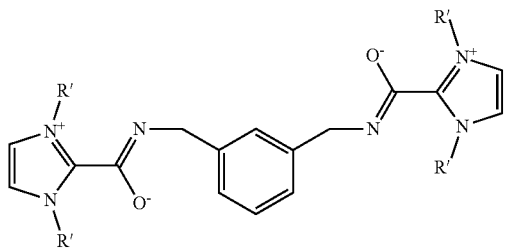
R' = CH₃ (4-2-17r)
Bu (4-2-17s)
(CH₂)₇CH₃ (4-2-17t)
CH₂CH(Et)Bu (4-2-17u)
CH₂Ph (4-2-17v)
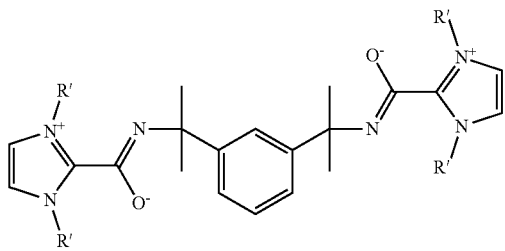
R' = CH₃ (4-2-18r)
Bu (4-2-18s)
(CH₂)₇CH₃ (4-2-18t)
CH₂CH(Et)Bu (4-2-18u)
CH₂Ph (4-2-18v)

-continued
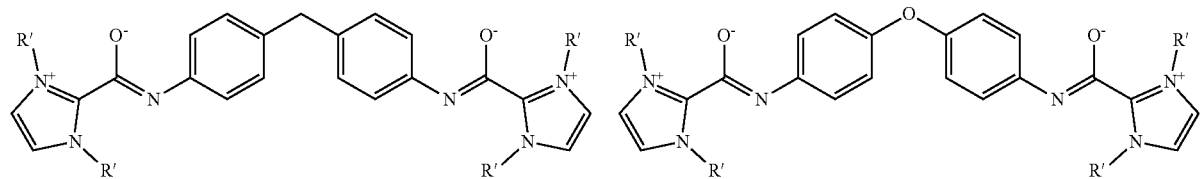
| R' = CH₃ | (4-2-19r) | | R' = CH₃ | (4-2-20r) |
| Bu | (4-2-19s) | | Bu | (4-2-20s) |
| (CH₂)₇CH₃ | (4-2-19t) | | (CH₂)₇CH₃ | (4-2-20t) |
| CH₂CH(Et)Bu | (4-2-19u) | | CH₂CH(Et)Bu | (4-2-20u) |
| CH₂Ph | (4-2-19v) | | CH₂Ph | (4-2-20v) |
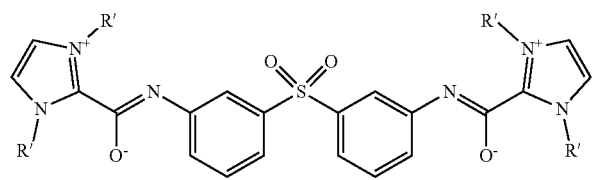
| R' = CH₃ | (4-2-21r) |
| Bu | (4-2-21s) |
| (CH₂)₇CH₃ | (4-2-21t) |
| CH₂CH(Et)Bu | (4-2-21u) |
| CH₂Ph | (4-2-21v) |
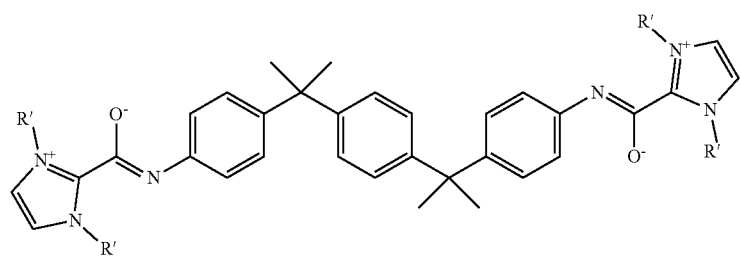
| R' = CH₃ | (4-2-22r) |
| Bu | (4-2-22s) |
| (CH₂)₇CH₃ | (4-2-22t) |
| CH₂CH(Et)Bu | (4-2-22u) |
| CH₂Ph | (4-2-22v) |
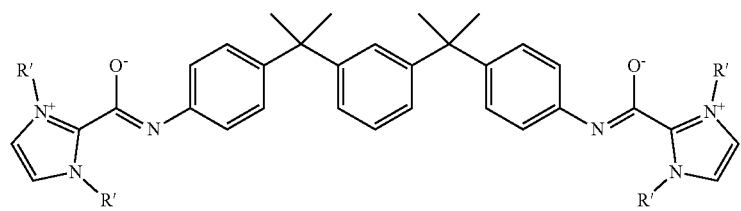
| R' = CH₃ | (4-2-23r) |
| Bu | (4-2-23s) |
| (CH₂)₇CH₃ | (4-2-23t) |
| CH₂CH(Et)Bu | (4-2-23u) |
| CH₂Ph | (4-2-23v) |

-continued
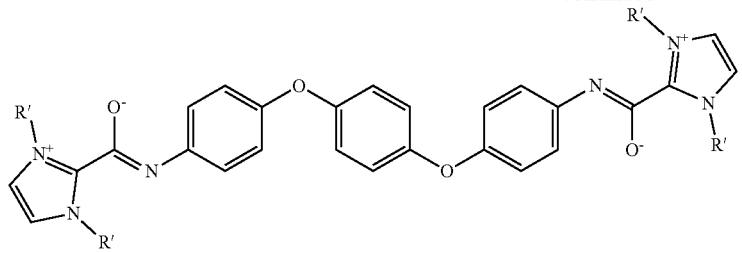
R' = CH₃    (4-2-24r)
Bu    (4-2-24s)
(CH₂)₇CH₃    (4-2-24t)
CH₂CH(Et)Bu    (4-2-24u)
CH₂Ph    (4-2-24v)
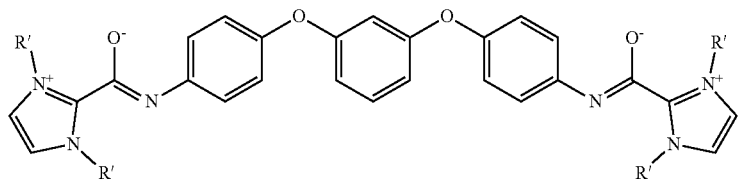
R' = CH₃    (4-2-25r)
Bu    (4-2-25s)
(CH₂)₇CH₃    (4-2-25t)
CH₂CH(Et)Bu    (4-2-25u)
CH₂Ph    (4-2-25v)
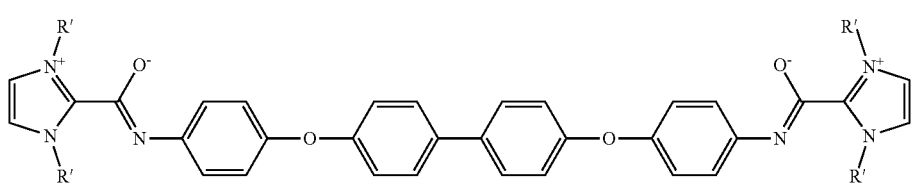
R' = CH₃    (4-2-26r)
Bu    (4-2-26s)
(CH₂)₇CH₃    (4-2-26t)
CH₂CH(Et)Bu    (4-2-26u)
CH₂Ph    (4-2-26v)
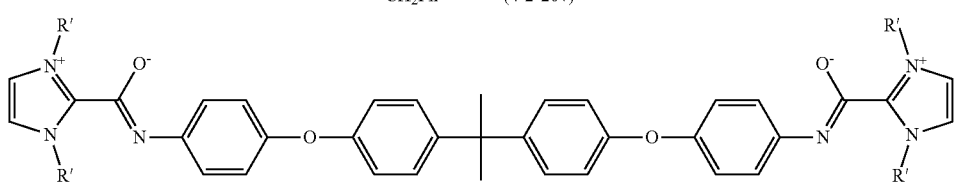
R' = CH₃    (4-2-27r)
Bu    (4-2-27s)
(CH₂)₇CH₃    (4-2-27t)
CH₂CH(Et)Bu    (4-2-27u)
CH₂Ph    (4-2-27v)
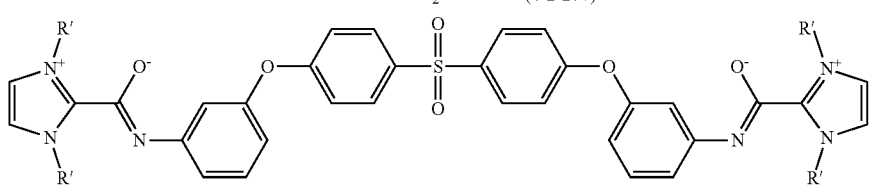
R' = CH₃    (4-2-28r)
Bu    (4-2-28s)
(CH₂)₇CH₃    (4-2-28t)
CH₂CH(Et)Bu    (4-2-28u)
CH₂Ph    (4-2-28v)

-continued
(4-3-1r)
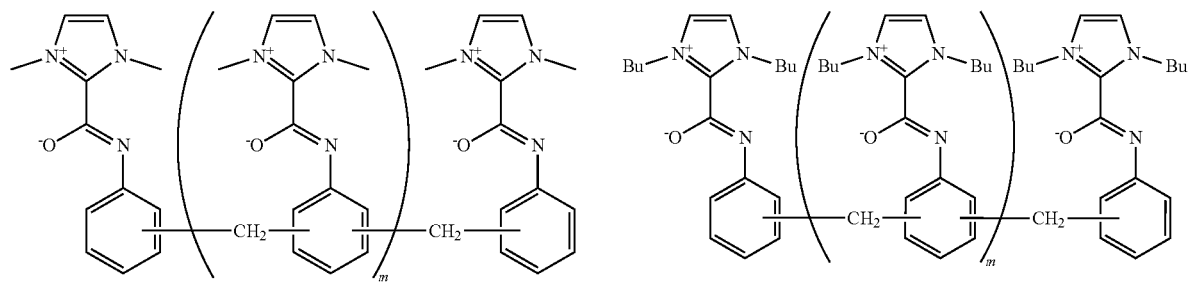
(4-3-1s)
(4-3-1t)
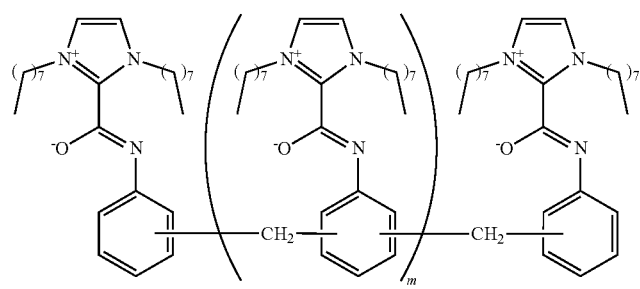
(4-3-1u)
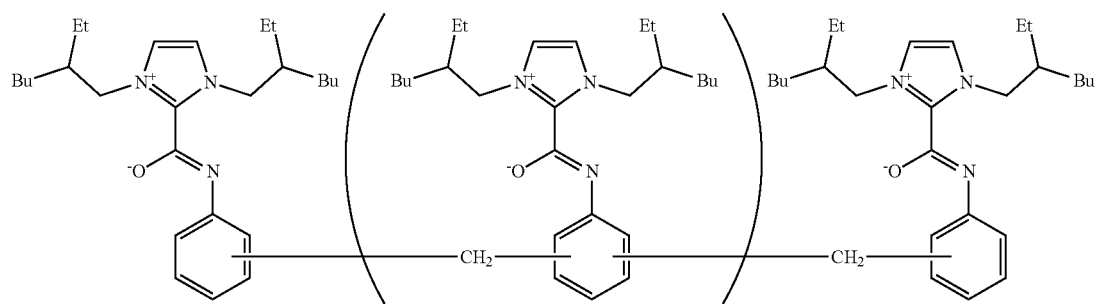
(4-3-1v)
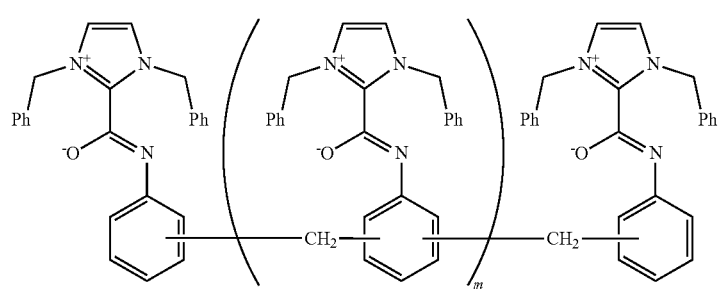

In Formulas (4-3-1r) to (4-3-1v), m is an integer of 0 to 4.

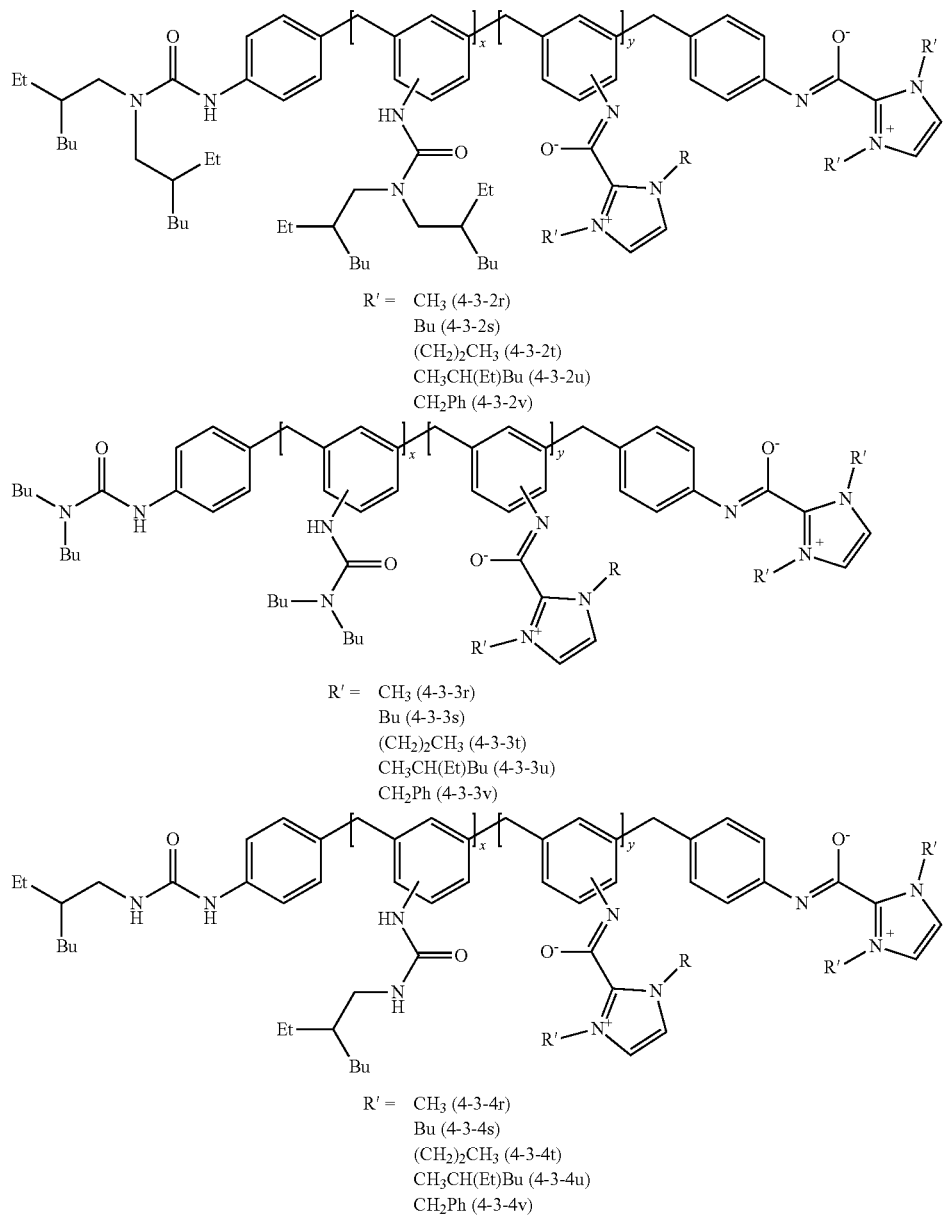

In Formulas (4-3-2r) to (4-3-2v), (4-3-3r) to (4-3-3v), and (4-3-4r) to (4-3-4v), x and y are each 0 or an integer of 1 or more.

Preferable examples of the amidate compound (4) include compounds represented by Formulas (4-1-5r), (4-1-15r), (4-1-16r), (4-1-18r), (4-1-19r), (4-1-21r), (4-1-24r), (4-1-26r), (4-1-27r), (4-1-28r), (4-1-5s), (4-1-15s), (4-1-16s), (4-1-18s), (4-1-19s), (4-1-21s), (4-1-24s), (4-1-26s), (4-1-27s), (4-1-28s), (4-1-5t), (4-1-15t), (4-1-16t), (4-1-18t), (4-1-19t), (4-1-21t), (4-1-24t), (4-1-26t), (4-1-27t), (4-1-28t), (4-1-5u), (4-1-15u), (4-1-16u), (4-1-18u), (4-1-19u), (4-1-21u), (4-1-24u), (4-1-26u), (4-1-27u), (4-1-28u), (4-1-5v), (4-1-15v), (4-1-16v), (4-1-18v), (4-1-19v), (4-1-21v), (4-1-24v), (4-1-26v), (4-1-27v), (4-1-28v), (4-2-13r), (4-2-14r), (4-2-19r), (4-2-21r), (4-2-22r), (4-2-23r), (4-2-25r), (4-2-13s), (4-2-14s), (4-2-19s), (4-2-21s), (4-2-22s), (4-2-23s), (4-2-25s), (4-2-13t), (4-2-14t), (4-2-19t), (4-2-21t), (4-2-22t), (4-2-23t), (4-2-25t), (4-2-13u), (4-2-14u), (4-2-19u), (4-2-21u), (4-2-22u), (4-2-23u), (4-2-25u), (4-2-13v), (4-2-14v), (4-2-19v), (4-2-21v), (4-2-22v), (4-2-23v), and (4-2-25v); and particularly preferably compounds represented by Formulas (4-1-15r), (4-1-15s), (4-1-15t), (4-1-15u), and (4-1-15v).

When the amidate compound (4) is an isomer, such as an enantiomer, a stereoisomer, or a regioisomer, the amidate compound (4) includes a mixture of any isomers, unless the isomer is specified. For example, when the amidate compound (4) is an enantiomer, the amidate compound (4) also includes enantiomers divided from the racemic form. These isomers can be obtained as single compounds by conventionally known separation methods (concentration, solvent extraction, column chromatography, recrystallization, etc.).

The reaction between the iminium salt (1) and the organic compound (3) is explained.

In the reaction between the iminium salt (1) and the organic compound (3), the iminium salt (1) is generally reacted in an amount of 0.8 mol or more, and preferably 1 to 3 mol, per mol of the group represented by Q contained in the organic compound (3).

The reaction temperature is not particularly limited, but is generally −10° C. or higher, preferably 0 to 200° C., and more preferably 20 to 150° C.

A solvent may or may not be used. Examples of solvents include aromatic hydrocarbon solvents, such as toluene, benzene, and xylene; aliphatic hydrocarbon solvents, such as methylcyclohexane, cyclohexane, hexane, heptane, and octane; halogenated hydrocarbon solvents, such as butyl chloride and 1,2-dichloroethane; halogenated aromatic hydrocarbon solvents, such as chlorobenzene; and the like. Preferable among these are aromatic hydrocarbon solvents and halogenated aromatic hydrocarbon solvents; and particularly preferable are toluene, xylene, and chlorobenzene. The solvents can be used as a mixture of two or more, if necessary.

The amount of solvent used is generally 50 parts by weight or less, and preferably 0.1 parts by weight or more and 35 parts by weight or less, per part by weight of the iminium salt (1).

The reaction may be performed, if necessary, in an inert gas atmosphere, such as nitrogen, argon, or helium, which do not affect the reaction.

After completion of the reaction, the amidate compound (4) can be obtained by removing the solvent by concentrating or filtering the reaction liquid, and may be purified by recrystallization, column separation, etc., if necessary.

Blocking Agent Dissociation Catalyst for Blocked Isocyanates

The amidate compound (4) can be used as a blocking agent dissociation catalyst for blocked isocyanates. The blocking agent dissociation catalyst for blocked isocyanates is a catalyst capable of promoting the reaction to dissociate a blocking agent that blocks the isocyanate groups of a blocked isocyanate and suppresses the reaction.

When the amidate compound (4) is used as a blocking agent dissociation catalyst for blocked isocyanates, in terms of improving the compatibility with a mixture of a blocked isocyanate and a compound having an isocyanate-reactive group and with polyurethane resins, the amidate compound (4) is preferably an amidate compound (4) having a nitrogen-containing organic group represented by Formula (2), wherein $R^1$ and $R^4$ are the same or different, and are each a $C_2$-$C_{30}$ hydrocarbon group that may contain a heteroatom; more preferably an amidate compound (4) having a nitrogen-containing organic group, wherein $R^1$ and $R^4$ are the same or different, and are each a $C_7$-$C_{30}$ hydrocarbon group that may contain a heteroatom; and even more preferably an amidate compound (4) having a nitrogen-containing organic group, wherein $R^1$ and $R^4$ are the same or different, and are each a $C_7$-$C_{20}$ hydrocarbon group that may contain a heteroatom.

The blocking agent dissociation catalyst for blocked isocyanates containing the amidate compound (4) (hereinafter referred to as "the blocking agent dissociation catalyst (A)") is explained.

The blocking agent dissociation catalysts (A) can be used singly or as a mixture of two or more. Further, a solvent or the like can be mixed and used, if necessary.

The solvent is not particularly limited. Examples include hydrocarbon solvents, such as benzene, toluene, xylene, cyclohexane, mineral spirit, and naphtha; ketone solvents, such as acetone, methyl ethyl ketone, and methyl isobutyl ketone; ester solvents, such as ethyl acetate, butyl acetate, and cellosolve acetate; alcohol solvents, such as methanol, ethanol, 2-propanol, butanol, 2-methoxyethanol, 2-ethoxyethanol, and 2-butoxyethanol; polyol solvents, such as ethylene glycol, propylene glycol, diethylene glycol, polyethylene glycol, and glycerol; water; and the like. These solvents may be used singly or in combination of two or more.

The blocking agent dissociation catalyst (A) for blocked isocyanates of the present invention is a catalyst that promotes the dissociation of a blocking agent from a block isocyanate, and the curing of a mixture of the blocked isocyanate and a compound having an isocyanate-reactive group.

The blocking agent dissociation catalyst (A) of the present invention can sufficiently achieve the object of the present invention, as long as it contains the amidate compound (4) as an active ingredient. If necessary, the blocking agent dissociation catalyst (A) of the present invention may contain a known blocking agent dissociation catalyst for blocked isocyanates.

The present invention also includes the following embodiments.

The amidate compound represented by Formula (4) for use as a blocking agent dissociation catalyst for blocked isocyanates.

Use of the amidate compound represented by Formula (4) as a blocking agent dissociation catalyst for blocked isocyanates.

Use of the amidate compound represented by Formula (4) for producing a blocking agent dissociation catalyst for blocked isocyanates.

The blocking agent dissociation catalyst of the present invention can be preferably used as a catalyst in a blocking agent dissociation method, for example.

In the method of the present invention, a blocked isocyanate is heated in the presence of the blocking agent dissociation catalyst for blocked isocyanates described above.

In the method of the present invention, the amount of the blocking agent dissociation catalyst (A) used is not particularly limited. The amount of the amidate compound (4) contained in the blocking agent dissociation catalyst (A) is generally 0.01 to 15 wt. %, preferably 0.05 to 10 wt. %, and more preferably 0.1 to 5 wt. %, in a thermosetting composition explained below.

The reaction temperature varies depending on the blocked isocyanate used, but is generally about 60 to 250° C., and preferably about 80 to 200° C. The reaction time is about 30 seconds to 5 hours, and preferably about 30 seconds to 2 hours.

The blocking with a blocking agent can be dissociated by the method of the present invention.

Next, the thermosetting composition of the present invention is explained.

The thermosetting composition of the present invention comprises the blocking agent dissociation catalyst (A) of the present invention described above, a blocked isocyanate, and a compound having an isocyanate-reactive group.

Examples of blocked isocyanates include compounds obtained by reacting known polyisocyanates and a known blocking agent so that the isocyanate groups in the polyisocyanates are blocked with the blocking agent. The blocked isocyanates may be used singly or as a mixture of two or more.

In the present invention, the polyisocyanate is not particularly limited, as long as it is a compound having two or more isocyanate groups. Examples of known polyisocyanates include aliphatic polyisocyanates, alicyclic polyisocyanates, aromatic polyisocyanates, aromatic aliphatic polyisocyanates, modified polyisocyanates thereof, and the like. These polyisocyanates may be used singly or as a mixture of two or more.

Examples of aliphatic polyisocyanates include 1,4-tetramethylene diisocyanate, 1,6-hexamethylene diisocyanate, 2,2,4-trimethylhexamethylene diisocyanate, 2,4,4-trimethylhexamethylene diisocyanate, lysine diisocyanate, dimer acid diisocyanate, and the like.

Examples of alicyclic polyisocyanates include 1,3-bis(isocyanatomethyl)cyclohexane, 1,4-bis(isocyanatomethyl)cyclohexane, 3-isocyanatomethyl-3,3,5-trimethylcyclohexane (isophorone diisocyanate), bis-(4-isocyanatocyclohexyl)methane, norbornane diisocyanate, and the like.

Examples of aromatic polyisocyanates include 2,4'-diphenylmethane diisocyanate, 4,4'-diphenylmethane diisocyanate, crude diphenylmethane diisocyanate, 1,4-phenylene diisocyanate, 2,4-tolylene diisocyanate, 2,6-tolylene diisocyanate, 3,3'-dimethyl-4,4'-diisocyanatobiphenyl, 3,3'-dimethyl-4,4'-diisocyanatodiphenylmethane, 1,5-naphthylene diisocyanate, and the like.

Examples of aromatic aliphatic polyisocyanates include 1,3-xylylene diisocyanate, 1,4-xylylene diisocyanate, α,α,α',α'-tetramethylxylylene diisocyanate, and the like.

Examples of modified polyisocyanates include isocyanate-terminated compounds obtained by the reaction of the above polyisocyanate compounds with compounds having an active hydrogen group, and reaction products of the polyisocyanate compounds and/or the isocyanate-terminated compounds (e.g., adduct-type polyisocyanates, and modified isocyanates obtained by allophanatization reaction, carbodiimidization reaction, uretodionization reaction, isocyanuration reaction, uretoniminization reaction, biuretization reaction, or the like).

Examples of known blocking agents include alcohols, such as methanol, ethanol, propanol, isopropanol, butanol, sec-butanol, tert-butanol, 2-ethylhexanol, and butyl cellosolve; phenols, such as phenol, cresol, and 2-hydroxypyridine; amines, such as diisopropylamine; lactams, such as ε-caprolactam, δ-valerolactam, and γ-butyrolactam; oximes, such as formaldehyde oxime, acetaldehyde oxime, acetone oxime, methyl ethyl ketoxime, and methyl isobutyl ketoxime; ketoenols, such as acetylacetone; pyrazoles, such as 1,2-pyrazole and 3,5-dimethylpyrazole; triazoles, such as triazole; and the like. Preferable among these are lactams, oximes, and pyrazoles; and particularly preferable are ε-caprolactam, methyl ethyl ketoxime, and 3,5-dimethylpyrazole.

Examples of the compound having an isocyanate-reactive group include compounds having two or more active hydrogen groups, such as polyols, polyamines, and alkanolamines. These compounds having an isocyanate-reactive group may be a mixture of two or more.

In the present invention, polyols are compounds having two or more hydroxyl groups. Examples of polyols include polyether polyols, polyester polyols, acrylic polyols, polyolefin polyols, fluorine polyols, polycarbonate polyols, polyurethane polyols, and the like. These polyols may be a mixture of two or more.

Examples of polyether polyols include active hydrogen compounds, such as aliphatic amine polyols, aromatic amine polyols, Mannich polyols, polyhydric alcohols, polyhydric phenols, and bisphenols; compounds obtained by adding alkylene oxides to these active hydrogen compounds; and the like. These polyether polyols may be a mixture of two or more.

Examples of aliphatic amine polyols include alkylenediamine-based polyols and alkanolamine-based polyols. These polyol compounds are polyfunctional polyol compounds having terminal hydroxyl groups obtained by the ring-opening addition of at least one cyclic ether, such as ethylene oxide or propylene oxide, using alkylenediamine or alkanolamine as an initiator. As the alkylenediamine, known compounds can be used without limitation. Specifically, $C_{2-8}$ alkylenediamines, such as ethylenediamine, propylenediamine, butylenediamine, hexamethylenediamine, and neopentyldiamine, are preferably used. Among these, alkylenediamines having a small number of carbon atoms are more preferably used, and polyol compounds using ethylenediamine or propylenediamine as an initiator are particularly preferably used. Examples of alkanolamines include monoethanolamine, diethanolamine, and triethanolamine. The number of functional groups of a polyol compound using alkylenediamine as an initiator is 4, and the number of functional groups of a polyol compound using alkanolamine as an initiator is 3. The number of functional groups of a mixture thereof is 3 or 4. The hydroxyl value of the aliphatic amine polyol is generally 100 to 1500 mgKOH/g, and preferably 200 to 1200 mgKOH/g. These aliphatic amine polyols may be a mixture of two or more.

Aromatic amine polyols are polyfunctional polyether polyol compounds having terminal hydroxyl groups obtained by the ring-opening addition of at least one cyclic ether, such as ethylene oxide or propylene oxide, using an aromatic diamine as an initiator. As the initiator, a known aromatic diamine can be used without limitation. Specific examples include 2,4-toluenediamine, 2,6-toluenediamine, diethyltoluenediamine, 4,4'-diaminodiphenylmethane, p-phenylenediamine, o-phenylenediamine, naphthalenediamine, and the like. Among these, toluenediamine (2,4-toluenediamine, 2,6-toluenediamine, or a mixture thereof) is particularly preferably used. The number of functional groups of the aromatic amine polyol is 4, and the hydroxyl value is generally 100 to 1500 mgKOH/g, and preferably 200 to 1200 mgKOH/g. These aromatic amine polyols may be a mixture of two or more.

Mannich polyols are active hydrogen compounds having a hydroxyl value of 200 to 700 mgKOH/g and 2 to 4 functional groups and obtained by the Mannich reaction of phenol and/or an alkyl-substituted derivative thereof, formaldehyde, and alkanolamine, or polyol compounds having a hydroxyl value of 200 to 700 mgKOH/g and 2 to 4 functional groups and obtained by the ring-opening addition polymerization of the active hydrogen compounds with at least one of ethylene oxide and propylene oxide. These Mannich polyols may be a mixture of two or more.

Examples of polyhydric alcohols include dihydric alcohols (e.g., ethylene glycol, propylene glycol, 1,4-butanediol, 1,6-hexanediol, diethylene glycol, triethylene glycol, dipropylene glycol, and neopentyl glycol), trihydric or higher alcohols (e.g., glycerol, trimethylolpropane, pentaerythritol, methylglucoside, sorbitol, and sucrose), and the like. These polyhydric alcohols may be a mixture of two or more.

Examples of polyhydric phenols include pyrogallol, hydroquinone, and the like. These polyhydric phenols may be a mixture of two or more.

Examples of bisphenols include bisphenol A, bisphenol S, bisphenol F, low-condensates of phenols and formaldehyde, and the like. These bisphenols may be a mixture of two or more.

Examples of polyester polyols include polyester polyols obtained by the condensation reaction of a single or a mixture of dibasic acids selected from the group of carboxylic acids, such as succinic acid, adipic acid, sebacic acid, dimer acid, maleic anhydride, phthalic anhydride, isophthalic acid, and terephthalic acid, with a single or a mixture of polyhydric alcohols selected from the group of ethylene glycol, propylene glycol, diethylene glycol, neopentyl glycol, trimethylolpropane, glycerol, etc.; and polycaprolactones obtained by the ring-opening polymerization of ε-caprolactone using a polyhydric alcohol. These polyester polyols may be a mixture of two or more.

Acrylic polyols are compounds obtained by copolymerizing a single or a mixture of ethylenically unsaturated bond-containing monomers having a hydroxyl group with a single or a mixture of other ethylenically unsaturated bond-containing monomers copolymerizable therewith. Examples of the ethylenically unsaturated bond-containing monomer having a hydroxyl group include hydroxyethyl acrylate, hydroxypropyl acrylate, hydroxybutyl acrylate, hydroxyethyl methacrylate, hydroxypropyl methacrylate, hydroxybutyl methacrylate, and the like; and preferably hydroxyethyl acrylate and hydroxyethyl methacrylate. These acrylic polyols may be a mixture of two or more.

Examples of the other ethylenically unsaturated bond-containing monomers copolymerizable with the ethylenically unsaturated bond-containing monomer having a hydroxyl group include acrylates, such as methyl acrylate, ethyl acrylate, propyl acrylate, isopropyl acrylate, butyl acrylate, isobutyl acrylate, hexyl acrylate, cyclohexyl acrylate, 2-ethylhexyl acrylate, lauryl acrylate, benzyl acrylate, and phenyl acrylate; methacrylates, such as methyl methacrylate, ethyl methacrylate, propyl methacrylate, isopropyl methacrylate, n-butyl methacrylate, isobutyl methacrylate, hexyl methacrylate, cyclohexyl methacrylate, 2-ethylhexyl methacrylate, lauryl methacrylate, benzyl methacrylate, and phenyl methacrylate; unsaturated carboxylic acids, such as acrylic acid, methacrylic acid, maleic acid, and itaconic acid; unsaturated amides, such as acrylamide, methacrylamide, N,N-methylenebisacrylamide, diacetone acrylamide, diacetone methacrylamide, maleic acid amide, and maleimide; vinyl monomers, such as glycidyl methacrylate, styrene, vinyl toluene, vinyl acetate, acrylonitrile, and dibutyl fumarate; vinyl monomers having a hydrolyzable silyl group, such as vinyltrimethoxysilane, vinylmethyldimethoxysilane, and γ-(meth)acryloxypropyltrimethoxysilane; and the like.

Examples of polyolefin polyols include polybutadiene having two or more hydroxyl groups, hydrogenated polybutadiene, polyisoprene, hydrogenated polyisoprene, and the like. These polyolefin polyols may be a mixture of two or more.

Fluorine polyols are polyols containing fluorine in the molecule. Examples include copolymers of fluoroolefin, cyclovinyl ether, hydroxyalkyl vinyl ether, and vinyl monocarboxylate. These fluorine polyols may be a mixture of two or more.

Examples of polycarbonate polyols include those obtained by condensation polymerization of low-molecular-weight carbonate compounds, such as dialkyl carbonates (e.g., dimethyl carbonate), alkylene carbonates (e.g., ethylene carbonate), and diaryl carbonates (e.g., diphenyl carbonate), with low-molecular-weight polyols used in the polyester polyols described above. These polycarbonate polyols may be a mixture of two or more.

Polyurethane polyols can be obtained by a conventional method, for example, by reacting polyols and polyisocyanates. Examples of carboxyl group-free polyols include ethylene glycol and propylene glycol as low-molecular-weight polyols, and acrylic polyol, polyester polyol, and polyether polyol as high-molecular-weight polyols. These polyurethane polyols may be a mixture of two or more.

In the present invention, polyamines are compounds having two or more amino groups. Examples of polyamines include low-molecular-weight polyamines, high-molecular-weight polyamines, alkanolamines, and the like. These polyamines may be a mixture of two or more.

Examples of low-molecular-weight polyamines include aromatic amines, such as 4,4'-diphenylmethanediamine; araliphatic amines, such as 1,3- or 1,4-xylylenediamine and mixtures thereof; alicyclic amines, such as 3-aminomethyl-3,5,5-trimethylcyclohexylamine, 1,3-bis(aminomethyl)cyclohexane, and 1,4-cyclohexanediamine; aliphatic amines, such as ethylenediamine, 1,3-propanediamine, 1,4-butanediamine, 1,6-hexamethylenediamine, hydrazine, diethylenetriamine, triethylenetetramine, and tetraethylenepentamine; and the like. These low-molecular-weight polyamines may be a mixture of two or more.

Examples of high-molecular-weight polyamines include polyoxyalkylene diamine (weight average molecular weight: 400 to 4000), polyoxyalkylene triamine (weight average molecular weight: 400 to 5000), and the like. These high-molecular-weight polyamines may be a mixture of two or more.

Examples of alkanolamines include monoethanolamine, diethanolamine, N-(2-aminoethyl)ethanolamine, N-(2-hydroxypropyl)ethylenediamine, monopropanolamine, monoisopropanolamine, dipropanolamine, diisopropanolamine, ethylene glycol bis(3-aminopropyl)ether, neopentanolamine, methylethanolamine, and the like.

In the thermosetting composition of the present invention, the mixing ratio of the blocked isocyanate and the compound having an isocyanate-reactive group is determined by the required physical properties, and is not particularly limited. The mixing ratio is generally within the following range: [effective isocyanate groups (mol) in the blocked isocyanate]/[active hydrogen groups (mol) in the compound having an isocyanate-reactive group]=0.2 to 3. The effective isocyanate groups in the blocked isocyanate refer to isocyanate groups that are regenerated when the blocking agent is dissociated from the blocked isocyanate.

In the thermosetting composition of the present invention, the amount of the blocking agent dissociation catalyst (A) of the present invention used is not particularly limited. The amount of the amidate compound (4) contained in the blocking agent dissociation catalyst (A) is generally 0.01 to 15 wt. %, preferably 0.05 to 10 wt. %, and more preferably 0.1 to 5 wt. %, in the thermosetting composition.

In the thermosetting composition of the present invention, known catalysts for polyurethane production, additives, pigments, solvents, and the like that are commonly used in this technical field can be used, if necessary.

Known catalysts for polyurethane production are not particularly limited. Examples include tin compounds, such as dibutyltin dilaurate, dibutyltin di-2-ethylhexanate, dioctyltin dilaurate, dibutyltin diacetate, dibutyltin dioxide, dioctyltin dioxide, tin acetylacetonate, tin acetate, tin octylate, and tin laurate; bismuth compounds, such as bismuth octylate, bismuth naphthenate, and bismuth acetylacetonate; titanium compounds, such as tetra-n-butyl titanate, tetraisopropyl titanate, and titanium terephthalate; tertiary amine compounds, such as triethylamine, N,N,N',N'-tetramethylethylenediamine, N,N,N',N'-tetramethylpropylenediamine, N,N,N',N'',N'''-pentamethyldiethylenetriamine, N,N,N',N'', N''-pentamethyldipropylenetriamine, N,N,N',N',N'-tetramethylguanidine, 1,3,5-tris(N,N-dimethylaminopropyl)hexahydro-S-triazine, 1,4-diazabicyclo[2.2.2]octane (DABCO), 1,8-diazabicyclo[5.4.0]undecene-7, triethylenediamine, N,N,N',N'-tetramethylhexamethylenediamine, N-methyl-N'-(2-dimethylaminoethyl)piperazine, N,N'-dimethylpiperazine, dimethylcyclohexylamine, N-methylmorpholine, N-ethylmorpholine, bis(2-dimethylaminoethyl)ether, 1-methylimidazole, 1,2-dimethylimidazole, 1-isobutyl-2-methylimidazole, and 1-dimethylaminopropylimidazole; and quaternary ammonium salt compounds, such as tetraalkylammonium halides (e.g., tetramethylammonium chloride), tetraalkylammonium hydroxides (e.g., tetramethylammonium hydroxide salts), tetraalkylammonium organic acid salts (e.g., tetramethylammonium-2-ethylhexanoate, 2-hydroxypropyl trimethylammonium formate, and 2-hydroxypropyl trimethylammonium-2-ethylhexanoate).

Additives are not particularly limited. Examples include hindered amine-based, benzotriazole-based, and benzophenone-based UV absorbers; perchlorate-based and hydroxylamine-based coloration inhibitors; hindered phenol-based, phosphorus-based, sulfur-based, and hydrazide-based antioxidants; tin-based, zinc-based, and amine-based urethanization catalysts; leveling agents, rheology control agents, pigment dispersants, and the like.

Pigments are not particularly limited. Examples include organic pigments, such as quinacridone-based, azo-based, and phthalocyanine-based pigments; inorganic pigments, such as titanium oxide, barium sulfate, calcium carbonate, and silica; and other pigments, such as carbon-based pigments, metal foil pigments, and rust-preventive pigments.

Solvents are not particularly limited. Examples include hydrocarbons, such as benzene, toluene, xylene, cyclohexane, mineral spirit, and naphtha; ketones, such as acetone, methyl ethyl ketone, and methyl isobutyl ketone; esters, such as ethyl acetate, butyl acetate, and cellosolve acetate; alcohols, such as methanol, ethanol, 2-propanol, butanol, 2-methoxyethanol, 2-ethoxyethanol, and 2-butoxyethanol; polyhydric alcohols, such as ethylene glycol, propylene glycol, diethylene glycol, polyethylene glycol, and glycerol; water; and the like. These solvents may be used singly or in combination of two cr more.

When storage at high temperatures is assumed, the thermosetting composition of the present invention may be divided into a blocked isocyanate and a compound having an isocyanate-reactive group to form two-part thermosetting compositions, and when used, the two-part thermosetting compositions may be mixed to be used as the thermosetting composition of the present invention. In such a case, the blocking agent dissociation catalyst (A) can be added and used when the two-part thermosetting compositions are mixed, or the compound having an isocyanate-reactive group and the blocking agent dissociation catalyst (A) can be mixed in advance.

The thermosetting composition of the present invention can be used as top and intermediate coat paints for automobiles, anti-chipping paints, electrodeposition paints, paints for automotive parts, paints for automotive repair, paints for pre-coated metal and rust-proof steel plates for metal products, such as home appliances and office equipment, paints for building materials, paints for plastics, powder paints, adhesives, adhesion-imparting agents, sealing agents, and the like.

Next, the method for curing the thermosetting composition of the present invention is explained.

In the method of the present invention, a mixture of a blocked isocyanate and a compound having an isocyanate-reactive group is heated in the presence of the blocking agent dissociation catalyst for blocked isocyanates described above.

The reaction temperature varies depending on the blocked isocyanate used, but is generally about 60 to 250° C., and preferably about 80 to 200° C. The reaction time is about 30 seconds to 5 hours, and preferably about 1 minute to 30 minutes.

EXAMPLES

The present invention is described in detail below, based on Examples; however, the present invention is not limited thereto. In the Production Examples, Bruker AV400 was used for $^1$H-NMR measurement, which was performed at 400 MHz.

Baking of Thermosetting Composition

A thermosetting composition was applied to an aluminum plate (Paltech, A5052P), followed by baking on a hot plate at 140° C. for 30 minutes.

Evaluation of Compatibility

The coating film that underwent the baking mentioned above was cooled to room temperature. Then, the coating film appearance was evaluated by confirming whether it was clouded or transparent by visual observation.

Evaluation of Solvent Resistance

The coating film that underwent the baking mentioned above was cooled to room temperature; afterward, the coating film was rubbed back and forth 10 times with absorbent cotton soaked with 4-methyl-2-pentanone. The solvent resistance was evaluated by observing whether the coating film was dissolved and the aluminum plate, which is an article to be coated, was exposed.

Production Example 1: Synthesis of 1,3-dioctylimidazolium acetate ([DOI][OAc])

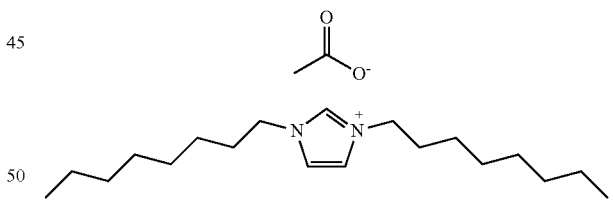

77.5 g (0.60 mol) of octylamine was placed in a 300-mL four-necked reactor purged with nitrogen, and the reaction liquid was cooled to 10° C. or less. Subsequently, a mixture of 22.9 g of 40% formaldehyde aqueous solution (formaldehyde pure content: 0.30 mol) and 27.0 g (0.45 mol) of acetic acid was added dropwise over 2 hours, followed by stirring at 0° C. for 30 minutes. The mixture was then returned to room temperature, and 43.5 g of 40% glyoxal aqueous solution (glyoxal pure content: 0.30 mol) was added. The resulting mixture was stirred at room temperature for 20 hours. After stirring the mixture, the resulting reaction mixture was washed three times with 50 g of heptane, and the resulting aqueous layer was concentrated under reduced pressure to give 108.4 g of a compound ([DOI][OAc]) represented by the above Formula. The ¹H-NMR analysis results of the compound represented by the above Formula are shown below.

¹H-NMR (DMSO-d6) δ (ppm)=9.32 (s, 1H), 7.80 (s, 2H), 4.17 (t, J=9.6 Hz, 4H), 1.78 (m, 4H), 1.63 (s, 3H), 1.23 (m, 20H), 0.85 (t, J=6.4 Hz, 6H)

Production Example 2: Synthesis of 1,3-bis(2-ethylhexyl)imidazolium acetate ([D2EHI][OAc])

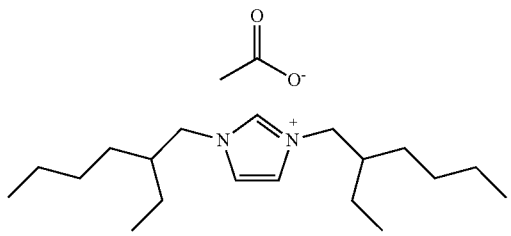

77.5 g (0.60 mol) of 2-ethylhexylamine was placed in a 300-mL four-necked reactor purged with nitrogen, and the reaction liquid was cooled to 10° C. or less. Subsequently, a mixture of 22.8 g (formaldehyde pure content: 0.30 mol) of 40% formaldehyde aqueous solution and 27.0 g (0.45 mol) of acetic acid was added dropwise over 2 hours, followed by stirring at 0° C. for 30 minutes. The mixture was then returned to room temperature, and 43.5 g of 40% glyoxal aqueous solution (glyoxal pure content: 0.30 mol) was added. The resulting mixture was stirred at room temperature for 20 hours. After stirring the mixture, the resulting reaction mixture was washed three times with 50 g of heptane, and the resulting aqueous layer was concentrated under reduced pressure to give 98.2 g of a compound ([D2EHI][OAc]) represented by the above Formula. The ¹H-NMR analysis results of the compound represented by the above Formula are shown below.

¹H-NMR (DMSO-d6) δ (ppm)=9.35 (s, 1H), 7.82 (s, 2H), 4.15 (d, J=7.2 Hz, 4H), 1.84 (m, 2H), 1.71 (s, 3H), 1.25 (m, 16H), 0.87 (t, J=7.2 Hz, 12H)

Production Example 3: Synthesis of 1,3-dibenzylimidazolium acetate ([DBnI][OAc])

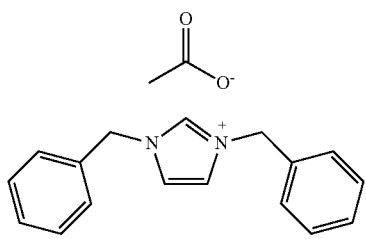

32.1 g (0.30 mol) of benzylamine was placed in a 300-mL four-necked reactor purged with nitrogen, and the reaction liquid was cooled to 10° C. or less. Subsequently, a mixture of 11.4 g (formaldehyde pure content: 0.15 mol) of 40% formaldehyde aqueous solution and 13.5 g (0.22 mol) of acetic acid was added dropwise over 2 hours, followed by stirring at 0° C. for 30 minutes. The mixture was then returned to room temperature, and 21.8 g of 40% glyoxal aqueous solution (glyoxal pure content: 0.15 mol), 28 g of methanol, and 28 g of toluene were added. The resulting mixture was stirred at room temperature for 20 hours. After stirring, the resulting reaction mixture was washed with 25 g of heptane for 3 times, and the resulting aqueous layer was concentrated under reduced pressure to give 45.3 g of a compound ([DBnI][OAc]) represented by the above Formula. The ¹H-NMR analysis results of the compound represented by the above Formula are shown below.

¹H-NMR (DMSO-d6) δ (ppm)=9.48 (s, 1H), 7.83 (s, 2H), 7.43 (m, 10H), 5.43 (s, 4H), 1.77 (s, 3H)

Production Example 4: Synthesis of 1,3-dibutylimidazolium acetate ([DBI][OAc])

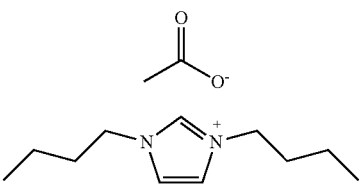

40.0 g (0.55 mol) of butyl amine was placed in a 300-mL four-necked reactor purged with nitrogen, and the reaction liquid was cooled to 10° C. or less. Subsequently, a mixture of 20.8 g (formaldehyde pure content: 0.27 mol) of 40% formaldehyde aqueous solution and 24.6 g (0.41 mol) of acetic acid was added dropwise over 2 hours, followed by stirring at 0° C. for 30 minutes. The mixture was then returned to room temperature, and 39.6 g of 40% glyoxal aqueous solution (glyoxal pure content: 0.27 mol) was added. The resulting mixture was stirred at room temperature for 20 hours. After stirring the mixture, the resulting reaction mixture was washed three times with 50 g of heptane, and the resulting aqueous layer was concentrated under reduced pressure to give 75.8 g of a compound ([DBI][OAc]) represented by the above Formula. The ¹H-NMR analysis results of the compound represented by the above Formula are shown below.

¹H-NMR (DMSO-d6) δ (ppm)=9.53 (s, 1H), 7.82 (s, 2H), 4.19 (t, J=6.8 Hz, 4H), 1.81 (m, 4H), 1.68 (s, 3H), 1.29 (m, 4H), 0.91 (t, J=7.2 Hz, 6H)

Production Example 5: Synthesis of 1,3-dioctylimidazolium formate ([DOI][HCO2])

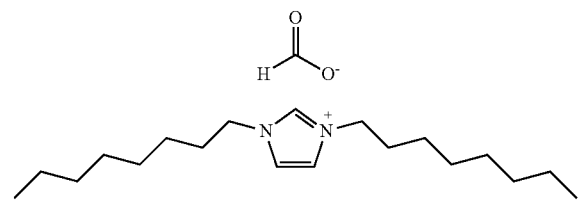

4.5 g (0.03 mol) of octylamine was placed in a 300-mL four-necked reactor purged with nitrogen, and the reaction liquid was cooled to 10° C. or less. Subsequently, a mixture of 1.3 g (formaldehyde pure content: 0.02 mol) of 40% formaldehyde aqueous solution and 1.2 g (0.03 mol) of acetic acid was added dropwise, followed by stirring at 0° C. for 30 minutes. The mixture was then returned to room temperature, and 2.5 g of 40% glyoxal aqueous solution (glyoxal pure content: 0.02 mol) was added. The resulting mixture was stirred at room temperature for 20 hours. After stirring the mixture, the resulting reaction mixture was washed three times with 50 g of heptane, and the resulting aqueous layer was concentrated under reduced pressure to give 6.4 g of the compound ([DOI][HCO2]) represented by the above Formula. The $^1$H-NMR analysis results of the compound represented by the above Formula are shown below.

$^1$H-NMR (DMSO-d6) δ (ppm)=9.28 (s, 1H), 8.43 (s, 1H), 7.81 (s, 2H), 4.16 (t, J=7.2 Hz, 4H), 1.82-1.76 (m, 4H), 1.24 (m, 20H), 0.85 (t, J=7.2 Hz, 6H)

Manufacturing Example 1: Synthesis of 1,3-dioctylimidazolium-2-N-phenylamidate (DOIm_PI)

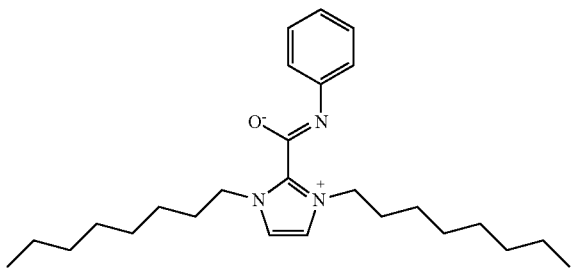

10.0 g (0.03 mol) of [DOI][OAc] obtained in Production Example 1, 50.0 g of chlorobenzene, and 3.0 g of molecular sieve 4A were placed, and allowed to stand for 16 hours under nitrogen. The molecular sieve 4A was then removed by filtration, and the resulting solution was placed in a 200-mL three-necked reactor purged with nitrogen. 15.4 g (0.10 mol) of methyl N-phenylcarbamate was added thereto, followed by stirring at 130° C. for 4 hours. After stirring, the resulting reaction mixture was concentrated under reduced pressure to give 24.0 g of a brown solid. The resulting brown liquid was isolated using an alumina column to give a compound (DOIm_PI) represented by the above Formula. The $^1$H-NMR analysis results of the compound represented by the above Formula are shown below.

$^1$H-NMR (DMSO-d6) δ (ppm)=7.60 (s, 2H), 7.41 (d, J=8.4 Hz, 2H), 7.12 (d, J=8.4 Hz, 2H), 6.79 (t, J=8.4 Hz, 1H), 4.48 (t, J=7.2 Hz, 4H), 1.79 (m, 4H), 1.28 (m, 20H), 0.87 (t, J=7.2 Hz, 6H)

Manufacturing Example 2: Synthesis of 1,3-bis(2-ethylhexyl) imidazolium-2-N-phenylamidate (D2EHIm_PI)

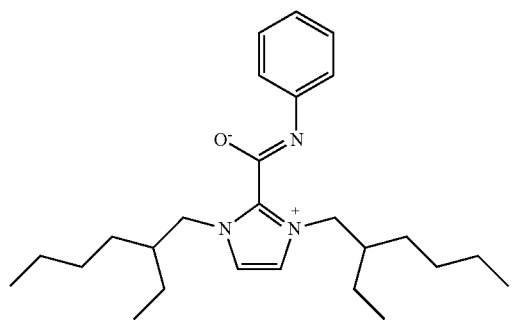

10.0 g (0.03 mol) of [D2HI][OAc] obtained in Production Example 2, 50.0 g of chlorobenzene, and 3.0 g of molecular sieve 4A were placed, and allowed to stand for 16 hours under nitrogen. The molecular sieve 4A was then removed by filtration, and the resulting solution was placed in a 200-mL three-necked reactor purged with nitrogen. 11.8 g (0.08 mol) of methyl N-phenylcarbamate was added thereto, followed by stirring at 130° C. for 4 hours. After stirring, 2.0 g of NaOH, 25.0 g of MeOH, and 50.0 g of water were added to the resulting reaction mixture, and the organic layer was extracted. Then, 50.0 g of water was added to the obtained organic layer, and an extraction operation was performed again. The resulting organic layer was then concentrated under reduced pressure to give 19.5 g of brown liquid. The resulting brown liquid was isolated using an alumina column to give a compound represented by the above Formula (D2EHIm_PI). The H-NMR analysis results of the compound represented by the above Formula are shown below.

$^1$H-NMR (DMSO-d6) δ (ppm)=7.59 (s, 2H), 7.39 (d, J=8.4 Hz, 2H), 7.12 (t, J=8.4 Hz, 2H), 6.76 (t, J=8.4 Hz, 1H), 4.44 (t, J=6.8 Hz, 4H), 1.86 (m, 2H), 1.25 (m, 16H), 0.82 (m, 12H)

Manufacturing Example 3: Synthesis of 1,3-dibenzylimidazolium-2-N-phenylamidate (DBnIm_PI)

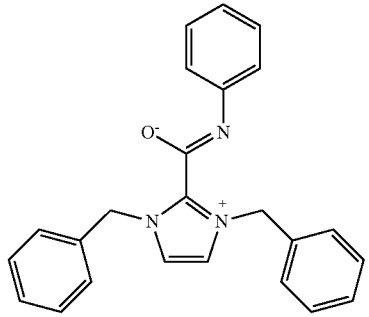

10.0 g (0.03 mol) of [DBnI][OAc] obtained in Production Example 3, 50.0 g of chlorobenzene, and 3.0 g of molecular sieve 4A were placed, and allowed to stand for 16 hours under nitrogen. The molecular sieve 4A was then removed by filtration, and the resulting solution was placed in a 200-mL three-necked reactor purged with nitrogen. 11.8 g (0.08 mol) of methyl N-phenylcarbamate was added thereto, followed by stirring at 130° C. for 4 hours. After stirring, the resulting reaction mixture was concentrated under reduced pressure to give 21.0 g of a brown liquid. The resulting brown liquid was isolated using an alumina column to give a compound represented by the above Formula (DBnIm_PI). The $^1$H-NMR analysis results of the compound represented by the above Formula are shown below.

$^1$H-NMR (DMSO-d6) δ (ppm)=7.65 (s, 2H), 7.43 (m, 12H), 7.12 (d, J=8.4 Hz, 2H), 6.83 (t, J=8.4 Hz, 1H), 5.83 (s, 4H)

Manufacturing Example 4: Synthesis of
1,3-dibutylimidazolium-2-N-phenylamidate
(DBIm_PI)

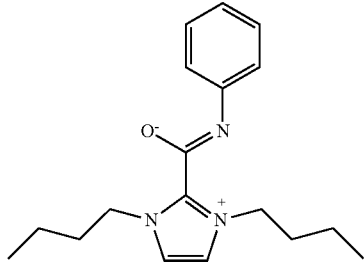

10.0 g (0.04 mol) of [DBI][QAc] obtained in Production Example 4, 50.0 g of chlorobenzene, and 0.3 g of molecular sieve 4A were placed, and allowed to stand for 16 hours under nitrogen. The molecular sieve 4A was then removed by filtration, and the resulting solution was placed in a 200-mL three-necked reactor purged with nitrogen. 11.8 g (0.08 mol) of methyl N-phenylcarbamate was added thereto, followed by stirring at 130° C. for 4 hours. After stirring, the resulting reaction mixture was concentrated under reduced pressure to give 20.0 g of a brown liquid. The resulting brown liquid was isolated using an alumina column to give a compound represented by the above Formula (DBIm_PI). The $^1$H-NMR analysis results of the compound represented by the above Formula are shown below.

$^1$H-NMR (DMSO-d6) δ (ppm)=7.60 (s, 2H), 7.42 (d, J=8.4 Hz, 2H), 7.14 (d, J=7.6 Hz, 2H), 6.80 (t, J=7.6 Hz, 1H), 4.48 (t, J=7.6 Hz, 4H), 1.80 (m, 4H), 1.30 (m, 4H), 0.91 (t, J=7.6 Hz, 6H)

Manufacturing Example 5: Synthesis of DOIm_PI 0.5 g (3.2 mmol) of [DOI][HCO2] obtained in Production Example 5, 5.3 g of chlorobenzene, and 0.5 g of molecular sieve 4A were placed, and allowed to stand for 16 hours under nitrogen. The molecular sieve 4A was then removed by filtration, and the resulting solution was placed in a 15-mL test tube purged with nitrogen. 1.1 g (6.9 mmol) of methyl N-phenylcarbamate was added thereto, followed by stirring at 130° C. for 4 hours. After stirring, the resulting reaction mixture was concentrated under reduced pressure, and the resulting brown liquid was isolated using an alumina column to give DOIm_PI.

Manufacturing Example 6: Synthesis of
1-ethyl-3-methylimidazolium-2-N-phenylamidate
(EMIm_PI)

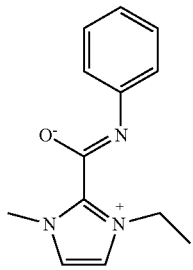

0.9 g (5.3 mmol) of 1-ethyl-3-methylimidazolium acetate produced by Tokyo Chemical Industry Co. Ltd., 3.0 g (25.2 mmol) of phenylisocyanate, and 5.1 g of chlorobenzene were placed in a 15-mL test tube, followed by stirring at 20° C. for 20 minutes. After stirring, the resulting reaction mixture was concentrated under reduced pressure, thereby giving 0.9 g of brown liquid. The resulting brown liquid was isolated using an alumina column to give a compound (EMIm_PI) represented by the above Formula. The $^1$H-NMR analysis results of the compound represented by the above Formula are shown below.

$^1$H-NMR (DMSO-d6) δ (ppm)=7.61 (s, 1H), 7.57 (s, 1H), 7.46 (d, J=7.6 Hz, 2H), 7.27 (t, J=7.6 Hz, 2H), 6.78 (t, J=7.6 Hz, 1H), 4.52-4.43 (m, 2H), 3.99 (s, 3H), 1.39 (t, J=7.2 Hz, 3H)

Manufacturing Example 7: Synthesis of EMIm_PI 0.8 g (3.2 mmol) of 1-ethyl-3-methylimidazolium lactate produced by TOKYO CHEMICAL INDUSTRY CO., LTD., 1.1 g (9.5 mmol) of phenyl isocyanate, and 3.3 g of chlorobenzene were placed, followed by stirring at 20° C. for 20 minutes. After stirring, the resulting reaction mixture was concentrated under reduced pressure to give 1.9 g of a brown liquid. The resulting brown liquid was isolated using an alumina column to give EMIm_PI.

Reference Production Example 1: Synthesis of
1-methyl-3-octylimidazolium-2-N-phenylamidate
(OMIm_PI)

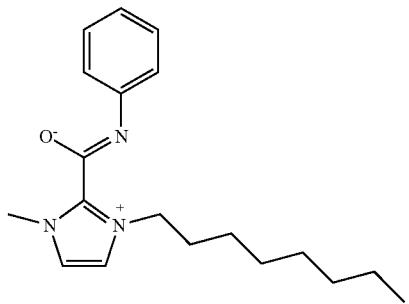

93.1 g (0.5 mol) of 1-octylimidazole, 93.0 g (1.0 mol) of dimethyl carbonate, and 93.1 g of methanol were placed in a 500-mL autoclave purged with nitrogen, followed by stirring at 135° C. for 24 hours. The resulting reaction mixture was cooled below the boiling point of the solvent, followed by concentration under reduced pressure. The resulting solid was washed three times with 150 mL of hexane, and dried to give 133.2 g of 1-methyl-3-octylimidazolium-2-carboxylate. Subsequently, 50.0 g (210 mmol) of the aforementioned 1-methyl-3-octylimidazolium-2-carboxylate and 500 mL of toluene were placed into a 200-mL three-necked flask purged with nitrogen, followed by heating at 110° C. 25.1 g (211 mmol) of phenyl isocyanate was added dropwise thereto over 2 hours, followed by stirring for 1 hour. The resulting reaction mixture was cooled to 25° C., concentrated under reduced pressure, and recrystallized by adding 150.5 g of butyl acetate, thereby giving 26.5 g of a compound (OMIm_PI) represented by the above Formula. The $^1$H-NMR analysis results of the compound represented by the above Formula are shown below.

$^1$H-NMR (CD$_3$OD) δ (ppm)=7.51 (s, 1H), 7.45-7.33 (m, 6H), 4.37 (t, J=7.4 Hz, 2H), 3.97 (s, 3H), 1.91-1.86 (m, 2H), 1.35-1.27 (m, 10H), 0.88 (t, J=6.8 Hz, 3H)

Example 1

1.85 g of polyester polyol (produced by TOYOBO Co., Ltd., Byron GK-68HA, hydroxyl value: 12.8 mgKOH/g), 0.15 g of blocked isocyanate (produced by Asahi Kasei Corporation, Duranate TPA-B80E, effective NCO: 12.4% by weight), and 0.04 g of the DOIm_PI obtained in Manufacturing Example 1 were mixed in the composition shown in Table 1, thereby giving a thermosetting composition. After the obtained thermosetting composition was baked, the compatibility and the solvent resistance were evaluated. The results are shown in Table 1.

Example 2

A thermosetting composition was obtained in the same manner as in Example 1, except that the D2EHIm_PI obtained in Manufacturing Example 2 was used in place of the DOIm_PI obtained in Production Example 1. After the obtained thermosetting composition was baked, the compatibility and the solvent resistance were evaluated. The results are shown in Table 1.

Example 3

A thermosetting composition was obtained in the same manner as in Example 1, except that the DBnIm_PI obtained in Manufacturing Example 3 was used in place of the DOIm_PI obtained in Production Example 1. After the obtained thermosetting composition was baked, the compatibility and the solvent resistance were evaluated. The results are shown in Table 1.

Example 4

A thermosetting composition was obtained in the same manner as in Example 1, except that the DBIm_PI obtained in Manufacturing Example 4 was used in place of the DOIm_PI obtained in Production Example 1. After the obtained thermosetting composition was baked, the compatibility and the solvent resistance were evaluated. The results are shown in Table 1.

Comparative Example 1: Evaluation of Thermosetting Composition Containing a Known Catalyst A thermosetting composition was obtained in the same manner as in Example 1, except that dibutyltin dilaurate (DBTDL) was used in place of the DOIm_PI obtained in Production Example 1. After the obtained thermosetting composition was baked, the compatibility and the solvent resistance were evaluated. The results are shown in Table 1.

Reference Example 1: Evaluation of Thermosetting Composition Containing 1-methyl-3-octylimidazolium-2-N-phenylamidate (OMIm_PI)

A thermosetting composition was obtained in the same manner as in Example 1, except that the 1-methyl-3-octyl-imidazolium-2-N-phenylamidate (OMIm_PI) obtained in Reference Production Example 1 was used in place of the DOIm_PI obtained in Production Example 1. After the obtained thermosetting composition was baked, the compatibility and the solvent resistance were evaluated. The results are shown in Table 1.

In Table 1, compatibility "A" indicates that the coating film has no clouding, and compatibility "C" indicates that the coating film has clouding. Solvent resistance "A" indicates that an aluminum plate, which was a coated material, was not exposed at all, and solvent resistance "C" indicates that the aluminum plate was exposed.

TABLE 1

|  | Polyester polyol | Blocked isocyanate | Catalyst | Compatibility | Solvent resistance |
|---|---|---|---|---|---|
| Example 1 | 1.85 g | 0.15 g | DOIm_PI 0.04 g | A | A |
| Example 2 | 1.85 g | 0.15 g | D2EHIm_PI 0.04 g | A | A |
| Example 3 | 1.85 g | 0.15 g | DBnIm_PI 0.04 g | A | A |
| Example 4 | 1.85 g | 0.15 g | DBIm_PI 0.04 g | A | A |
| Comparative Example 1 | 1.85 g | 0.15 g | DBTL 0.04 g | A | C |
| Reference Example 1 | 1.85 g | 0.15 g | OMIm-PI 0.04 g | C | A |

As is clear from a comparison between Examples 1 to 4 and Reference Example 2 in Table 1, the coating films each containing DOIm_PI, D2EHIm_PI, DBnIm_PI PI, or DBIm_PI, which is the amidate compound (4) of the present invention in which R$^1$ and R$^4$ of the nitrogen-containing organic group represented by Formula (2) have 2 to 30 carbon atoms, in particular 2 to 20 carbon atoms, had no clouding. In contrast, the coating film containing OMIm_PI, which is the amidate compound (4) in which R$^1$ of the nitrogen-containing organic group represented by Formula (2) has one carbon atom, had clouding. As described above, the amidate compound (4) of the present invention, in which R$^1$ and R$^4$ of the nitrogen-containing organic group represented by Formula (2) have 2 to 30 carbon atoms, was found to be superior in view of improving compatibility with a mixture of a blocked isocyanate and a compound having an isocyanate-reactive group, and a urethane resin.

As is clear from a comparison between Examples 1 to 4 and Reference Example 1 in Table 1, the coating film containing the amidate compound (4) of the present invention, in which $R^1$ and $R^4$ of the nitrogen-containing organic group represented by Formula (2) have 2 to 30 carbon atoms, had excellent solvent resistance and excellent catalytic activity, compared with a coating film containing a known catalyst.

The invention claimed is:

1. A method for producing an amidate compound represented by Formula (4), comprising reacting an iminium salt represented by the following Formula (1) and an organic compound represented by the following Formula (3):

Formula (1):

 (1)

wherein $G^-$ is an anion, and D is a nitrogen-containing organic group represented by Formula (2):

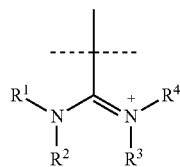 (2)

wherein $R^1$, $R^2$, $R^3$, and $R^4$ are the same or different, and are each a hydrocarbon group that may contain a heteroatom; and some or all of $R^1$, $R^2$, $R^3$, and $R^4$ may be bonded together to form a ring structure;

Formula (3):

 (3)

wherein A is a substituted or unsubstituted hydrocarbon group, n is an integer of 1 or more, Q is an —NCO group or an —NHCO$_2$R$^7$ group, and $R^7$ is a substituted or unsubstituted hydrocarbon group;

Formula (4):

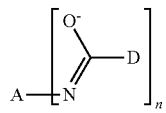 (4)

wherein A, D, and n are as defined above.

2. The method for producing an amidate compound according to claim 1, wherein the nitrogen-containing organic group represented by Formula (2) is a nitrogen-containing organic group represented by the following Formula (2-1), (2-2), or (2-3):

Formula (2-1):

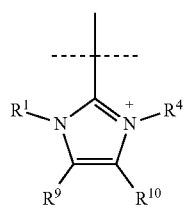 (2-1)

wherein $R^1$ and $R^4$ are as defined in claim 1, and $R^9$ and $R^{10}$ are the same or different, and are each a hydrogen atom or a $C_1$-$C_6$ hydrocarbon group that may contain a heteroatom;

Formula (2-2):

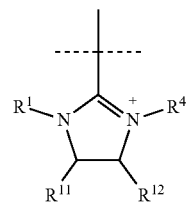 (2-2)

wherein $R^1$ and $R^4$ are as defined above, and $R^{11}$ and $R^{12}$ are the same or different, and are each a hydrogen atom or a $C_1$-$C_6$ hydrocarbon group that may contain a heteroatom; or Formula (2-3):

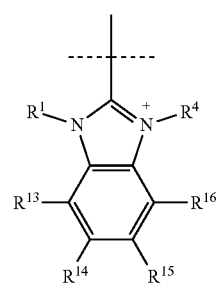 (2-3)

wherein $R^1$ and $R^4$ are as defined above, and $R^{13}$, $R^{14}$, $R^{15}$, and $R^{16}$ are the same or different, and are each a hydrogen atom or a $C_1$-$C_6$ hydrocarbon group that may contain a heteroatom.

3. The method for producing an amidate compound according to claim 1, wherein the organic compound represented by Formula (3) is represented by the following Formula (3-1), (3-2), or (3-3):

Formula (3-1):

 (3-1)

wherein Q is as defined in claim 1, and $R^5$ is a substituted or unsubstituted hydrocarbon group;

Formula (3-2):

 (3-2)

wherein Q is as defined above, and $R^6$ is a substituted or unsubstituted hydrocarbon group; or Formula (3-3):

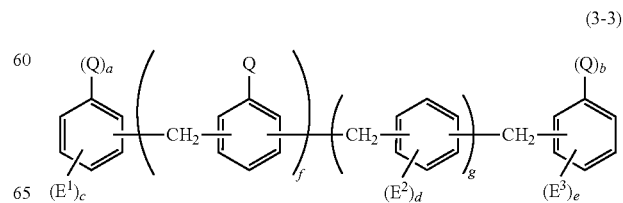 (3-3)

wherein Q is as defined above; $E^1$, $E^2$, and $E^3$ are each independently a substituted or unsubstituted hydrocarbon group, a halogen atom, an alkylamino group, a dialkylamino group, an alkoxy group, an aryloxy group, a nitro group, a cyano group, a sulfonyl group, an (alkylamino) carbonylamino group, a (dialkylamino) carbonylamino group, or an isocyanate group; f and g are each independently an integer of 0 to 4; a and b are 0 or 1; and c, d, and e are each independently an integer of 0 to 4; provided that when f is 0, at least one of a or bis 1.

4. The method for producing an amidate compound according to claim 1, wherein Q is an —$NHCO_2R^7$ group.

5. The method for producing an amidate compound according to claim 1, wherein $G^-$ is a carboxylate ion represented by the following Formula (5):

Formula (5):

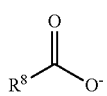

(5)

wherein $R^8$ is a hydrogen atom, a hydroxyl group, an alkoxy group, an fluoroalkyl group, or a hydrocarbon group that may contain a heteroatom.

6. The method for producing an amidate compound according to claim 1, wherein A is an unsubstituted hydrocarbon group or a hydrocarbon group having at least one substituent selected from the group consisting of a halogen atom, an alkylamino group, a dialkylamino group, an alkoxy group, an aryloxy group, a nitro group, a cyano group, a sulfonyl group, an (alkylamino) carbonylamino group, a (dialkylamino) carbonylamino group, and an isocyanate group.

7. The method for producing an amidate compound according to claim 1, wherein n is an integer of 1 to 6.

8. An amidate compound represented by the following Formula (4-1), (4-2), or (4-3):

Formula (4-1):

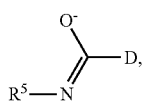

(4-1)

wherein $R^5$ is a phenyl group, and D is a nitrogen-containing organic group represented by the following Formula (2-1) or (2-3);

Formula (4-2):

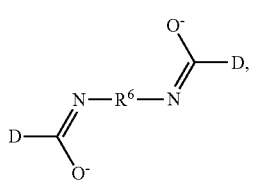

(4-2)

wherein $R^6$ is a phenylene group, and D is a nitrogen-containing organic group represented by the following Formula (2-1), (2-2), or (2-3);

Formula (4-3):

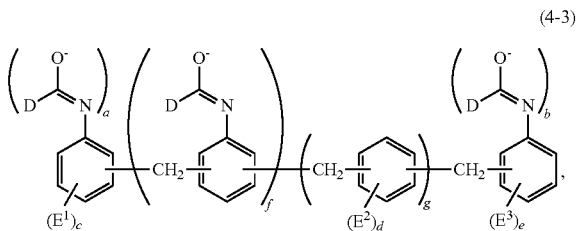

(4-3)

wherein D is a nitrogen-containing organic group represented by the following Formula (2-1), (2-2), or (2-3); $E^1$, $E^2$, and $E^3$ are each independently a substituted or unsubstituted hydrocarbon group, a halogen atom, an alkylamino group, a dialkylamino group, an alkoxy group, an aryloxy group, a nitro group, a cyano group, a sulfonyl group, an (alkylamino) carbonylamino group, a (dialkylamino) carbonylamino group, or an isocyanate group; f and g are each independently an integer of 0 to 4; a and b are 0 or 1; and c, d, and e are each independently an integer of 0 to 4;

provided that when f is 0, at least one of a or b is 1;

Formula (2-1):

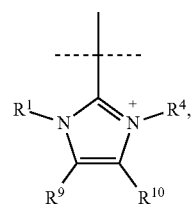

(2-1)

wherein $R^1$ and $R^4$ are the same or different, and are each a $C_2$-$C_{30}$ hydrocarbon group, and $R^9$ and $R^{10}$ are hydrogen atoms;

Formula (2-2):

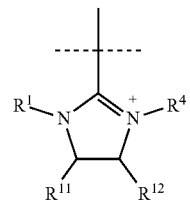

(2-2)

wherein $R^1$ and $R^4$ are the same or different, and are each a $C_2$-$C_{30}$ hydrocarbon group, and $R^{11}$ and $R^{12}$ are hydrogen atoms;

Formula (2-3):

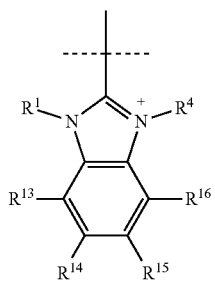

(2-3)

wherein $R^1$ and $R^4$ are the same or different, and are each a $C_2$-$C_{30}$ hydrocarbon group, and $R^{13}$, $R^{14}$, $R^{15}$, and $R^{16}$ are hydrogen atoms;

provided that 1,3-bis(2,6-diisopropylphenyl) imidazolium-2-N-phenylamidate is excluded.

9. A blocking agent dissociation catalyst for blocked isocyanates comprising an amidate compound represented by the following Formula (4-1), (4-2), or (4-3) Formula (4-1):

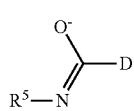

(4-1)

wherein $R^5$ is a phenyl group, and D is a nitrogen-containing organic group represented by the following Formula (2-1) or (2-3);

Formula (4-2):

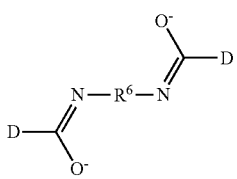

(4-2)

wherein $R^6$ is a phenylene group, and D is a nitrogen-containing organic group represented by the following Formula (2-1), (2-2), or (2-3);

Formula (4-3):

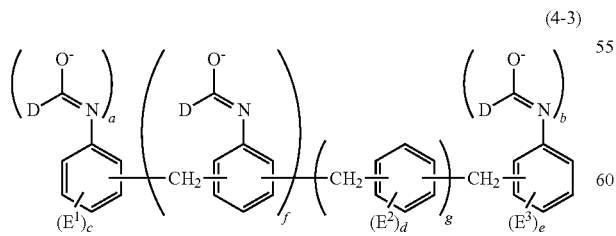

(4-3)

wherein D is a nitrogen-containing organic group represented by the following Formula (2-1), (2-2), or (2-3);

$E^1$, $E^2$, and $E^3$ are each independently a substituted or unsubstituted hydrocarbon group, a halogen atom, an alkylamino group, a dialkylamino group, an alkoxy group, an aryloxy group, a nitro group, a cyano group, a sulfonyl group, an (alkylamino) carbonylamino group, a (dialkylamino) carbonylamino group, or an isocyanate group; f and g are each independently an integer of 0 to 4; a and b are 0 or 1; and c, d, and e are each independently an integer of 0 to 4; provided that when f is 0, at least one of a or b is 1;

Formula (2-1):

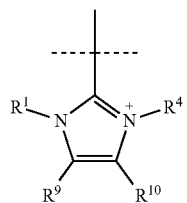

(2-1)

wherein $R^1$ and $R^4$ are the same or different, and are each a $C_2$-$C_{30}$ hydrocarbon group; and $R^9$ and $R^{10}$ are the same, and are hydrogen atoms;

Formula (2-2):

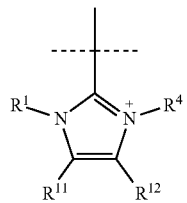

(2-2)

wherein $R^1$ and $R^4$ are the same or different, and are each a $C_2$-$C_{30}$ hydrocarbon group; and $R^{11}$ and $R^{12}$ are the same, and are hydrogen atoms; or Formula (2-3):

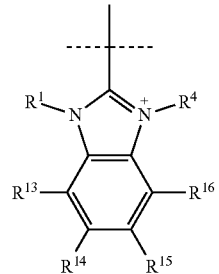

(2-3)

wherein $R^1$ and $R^4$ are the same or different, and are each a $C_2$-$C_{30}$ hydrocarbon group; and $R^{13}$, $R^{14}$, $R^{15}$, and $R^{16}$ are the same, and are hydrogen atoms.

10. A thermosetting composition comprising the blocking agent dissociation catalyst for blocked isocyanates according to claim 9, a blocked isocyanate, and a compound having an isocyanate-reactive group.

* * * * *